(12) United States Patent
Prince et al.

(10) Patent No.: US 9,546,184 B2
(45) Date of Patent: Jan. 17, 2017

(54) ALKYLOXY SUBSTITUTED THIAZOLOQUINOLINES AND THIAZOLONAPHTHYRIDINES

(71) Applicant: 3M INNOVATIVE PROPERTIES COMPANY, Saint Paul, MN (US)

(72) Inventors: Ryan B. Prince, Saint Paul, MN (US); Bryon A. Merrill, River Falls, WI (US); Philip D. Heppner, Forest Lake, MN (US); Tushar A. Kshirsagar, Woodbury, MN (US); Joshua R. Wurst, North Saint Paul, MN (US); Karl J. Manske, Roseville, MN (US); Michael J. Rice, Oakdale, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/732,815

(22) Filed: Jun. 8, 2015

(65) Prior Publication Data
US 2015/0266901 A1 Sep. 24, 2015

Related U.S. Application Data

(63) Continuation of application No. 11/884,052, filed on Aug. 13, 2008, now abandoned.

(51) Int. Cl.
*C07D 513/04* (2006.01)
*C07D 519/00* (2006.01)

(52) U.S. Cl.
CPC ........... *C07D 513/04* (2013.01); *C07D 519/00* (2013.01)

(58) Field of Classification Search
CPC combination set(s) only.
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |

(Continued)

FOREIGN PATENT DOCUMENTS

| | | |
|---|---|---|
| EP | 0 394 026 | 10/1990 |
| EP | 1 104 764 | 6/2001 |

(Continued)

OTHER PUBLICATIONS

Vilcek, J. "The cytokines: an overview" in The Cytokine Handbook 4th Edition vol. 1 Academic: 2004 New York, pp. 3-14.*
Mbow et. al. Mini-Reviews in Medicinal Chemistry, 2006, 6, 527-531.*
Muller and Kräusslich in "Antiviral Strategies" Handbook of Experimental Pharmacology vol. 189 Chapter 1, pp. 1-24.*
Koeneman et al. "TOPical Imiquimod treatment of high-grade Cervical intraepithelial neoplasia (Topic trial): study protocol for a randomized controlled trial" BMC Cancer (2016) 16:132, 1-7.*
McKendry "Atypical presentations of genital herpes simplex virus in HIV-1 and HIV-2 effectively treated by imiquimod" International Journal of STD & AIDS 2015, vol. 26(6) 441-443.*
Ströher et. al. "Progress towards the treatment of Ebola haemorrhagic fever" Expert Opinion in Investigational Drugs 2006 15, 1523-1535.*
Simone, Oncology: Introduction, Cecil Textbook of Medicine, 20th Edition, 1996 vol. 1, pp. 1004-1010.*

(Continued)

*Primary Examiner* — David K O'Dell
(74) *Attorney, Agent, or Firm* — 3M Innovative Properties Company; Eric E. Silverman

(57) ABSTRACT

Thiazoloquinolines and thiazolonaphthyridines with an alkoxy substituent at the 6, 7, 8, or 9-position, pharmaceutical compositions containing the compounds, intermediates, methods of making and methods of use of these compounds as immunomodulators, for inducing cytokine biosynthesis in animals and in the treatment of diseases including viral and neoplastic diseases are disclosed.

21 Claims, No Drawings

(56) References Cited

U.S. PATENT DOCUMENTS

| | | |
|---|---|---|
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Stratham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,993,659 B2 | 8/2011 | Noelle et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Stratham et al. |
| 2007/0155767 A1 | 7/2007 | Radmer et al. |
| 2007/0166384 A1 | 7/2007 | Zarraga et al. |
| 2007/0167479 A1 | 7/2007 | Busch et al. |
| 2007/0208052 A1 | 9/2007 | Prince et al. |
| 2007/0213355 A1 | 9/2007 | Capraro et al. |

(56) References Cited

U.S. PATENT DOCUMENTS

| | | |
|---|---|---|
| 2007/0213356 A1 | 9/2007 | Merrill et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0287725 A1 | 12/2007 | Moser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0275077 A1 | 11/2008 | Skwierczynski et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |

FOREIGN PATENT DOCUMENTS

| | | |
|---|---|---|
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/003064 | 1/2005 |
| WO | WO 2005/020999 | 3/2005 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Howington "Treatment of Stage I and II Non-small Cell Lung Cancer Diagnosis and Management of Lung Cancer, 3rd ed: American College of Chest Physicians Evidence-Based Clinical Practice Guidelines" CHEST 2013; 143(5)(Suppl):e278S-e313S.*

Socinski "Treatment of Stage IV Non-small Cell Lung Cancer Diagnosis and Management of Lung Cancer, 3rd ed: American College of Chest Physicians Evidence-Based Clinical Practice Guideline" CHEST 2013; 143(5)(Suppl):e341S-e368S.*

Jett Treatment of Small Cell Lung Cancer Diagnosis and Management of Lung Cancer, 3rd ed: American College of Chest Physicians Evidence-Based Clinical Practice Guidelines CHEST 2013; 143(5)(Suppl):e400S-e419S.*

Damia "Contemporary pre-clinical development of anticancer agents—What are the optimal preclinical models?" European Journal of Cancer 2009, 45, 2768-2781.*

Sharma "Cell line-based platforms to evaluate the therapeutic efficacy of candidate anticancer agents" Nature Reviews Cancer Apr. 2010, vol. 10, 241-253.*

Ocana, A. "Preclinical development of molecular targeted agents for cancer" Nat. Rev. Clin. Oncol. 2011, 8, 200-209.*

Ledford "US cancer institute overhauls cell lines" Nature Feb. 25, 2016 vol. 530 p. 391.*

Johnson, et. al. "Relationships between drug activity in NCI preclinical in vitro and in vivo models and early clinical trials." British Journal of Cancer 2001, 84, 1424-1431.*

Imiquimod—National Cancer Institute Online: "http://www.cancer.gov/about-cancer/treatment/drugs/imiquimod" accessed Apr. 4, 2016.*

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul., 78, 1983.

Testerman et al., "Cytokine Induction by the Immunomodulators Imiquimod and S-27609." *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", (1976). *Chem. Abs.* 85, 94362.

Berenyi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-αSuppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

Torrence and DeClercq, "Inducers and Induction of Interferons", *Pharmac Ther*, 2, pp. 1-88 (1977).

Beutler et al., *Crit Care Med.*, 1993, 21 (10 Suppl), S423-35.

Brassard et al., *J. Leukocyte Biology*, 71, 565-581 (2002).

Rothel et al., *Immunol Cell Biol.*, 1998, 76(2), 167-72.

Sambhi et al., *Proc Natl Acad Sci USA*, 1991, 88(9), 4025-9.

Wedlock et al., *Immunol Cell Biol.* 1999, 77(1), 28-33.

* cited by examiner

ALKYLOXY SUBSTITUTED THIAZOLOQUINOLINES AND THIAZOLONAPHTHYRIDINES

CROSS REFERENCE TO RELATED APPLICATIONS

This application is a continuation of U.S. application Ser. No. 11/884,052, filed Aug. 13, 2008, now pending, which is a national stage filing under 35 U.S.C. 371 of PCT/US2006/004391, filed Aug. 9, 2007, which claims priority to U.S. Provisional Application Ser. No. 60/651,585, filed Feb. 9, 2005, and U.S. Provisional Application Ser. No. 60/733,036, filed Nov. 3, 2005, the disclosures of which are incorporated by reference in their entirety herein.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

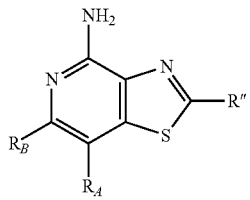

I wherein $R_A$, $R_B$, and R" are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection or disease and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a", "an", "the", "at least one", and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through VII:

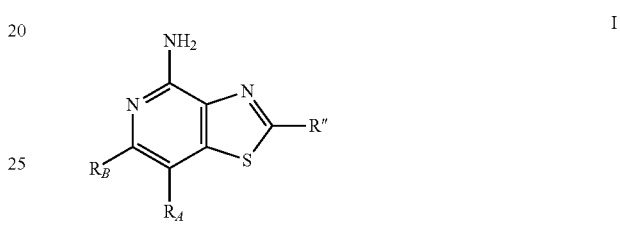

I

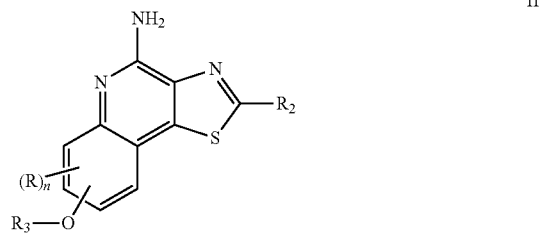

II

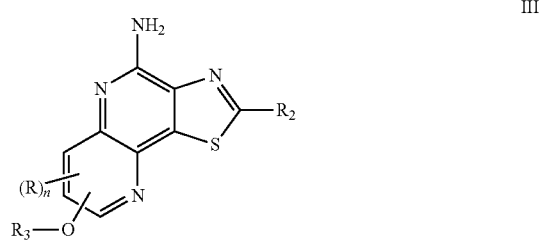

III

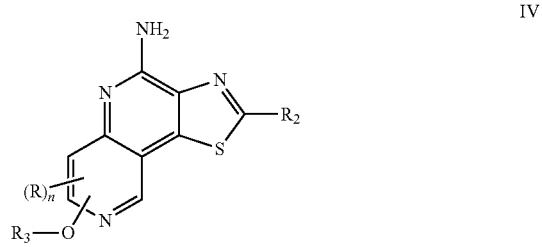

IV

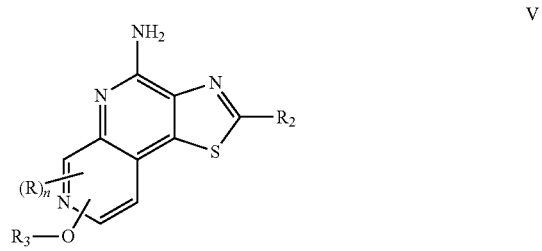

V

-continued

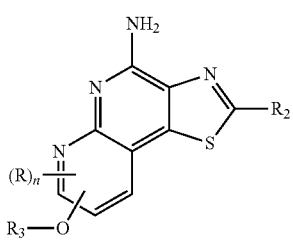

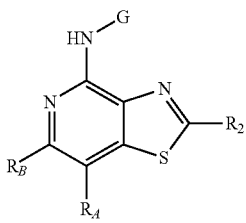

as well as intermediates of the following Formulas X through XIII:

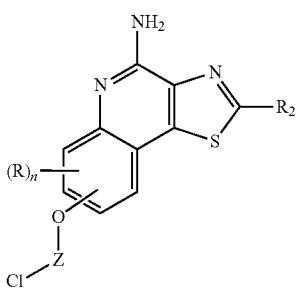

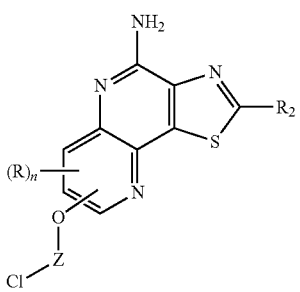

wherein $R_A$, $R_B$, R", R, $R_2$, $R_3$, n, G, and Z are as defined below.

In one embodiment, the present invention provides a compound of Formula I:

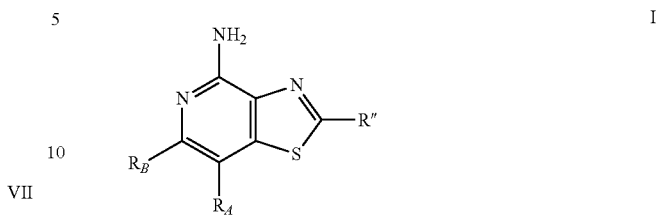

wherein:

$R_A$ and $R_B$ taken together form a fused benzene ring or fused pyridine ring wherein the benzene ring or pyridine ring is substituted by one —O—$R_3$ group, or substituted by one —O—$R_3$ group and one R group;

$R_3$ is selected from the group consisting of:
—Z—Y—$R_4$,
—Z—Y—X—Y—$R_4$,
—Z—Y—X—Y—X—Y—$R_4$,
—Z—$R_5$,
—Z-Het,
—Z-Het'-$R_4$, and
—Z-Het'-Y—$R_4$;

R is selected from the group consisting of alkyl, alkoxy, hydroxy, halogen, and trifluoromethyl;

R" is hydrogen or a non-interfering substituent;

Z is selected from the group consisting of alkylene, alkenylene, and alkynylene, wherein alkylene, alkenylene, and alkynylene can be optionally interrupted with one or more —O— groups;

Y is selected from the group consisting of:
—S(O)$_{0-2}$—,
—S(O)$_2$—N($R_8$)—,
—C($R_6$)—,
—C($R_6$)—O—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—CH(—N(—O—$R_8$)-Q-$R_4$)—,

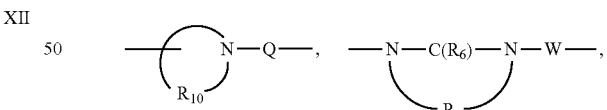

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

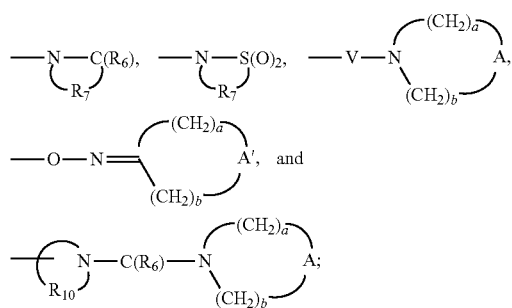

$R_6$ is selected from the group consisting of =O and =S;
$R_7$ is $C_{2-7}$ alkylene;
$R_8$ is selected from the group consisting of hydrogen, alkyl, hydroxyalkylenyl, alkoxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —CH$_2$—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
with the proviso that Z can also be a bond when:
$R_3$ is —Z-Het, —Z-Het'-R$_4$, or —Z-Het-Y—R$_4$, and Z is attached to an atom other than N in Het or Het; or $R_3$ is —Z—Y—R$_4$, —Z—Y—X—Y—R$_4$, or —Z—Y—X—Y—X—Y—R$_4$, and the Y group bonded to Z is —S(O)$_2$—, —S(O)$_2$—N(R$_8$)—, —C(R$_6$)—, —C(R$_6$)—O—, —C(R$_6$)—N(R$_8$)—,

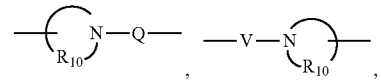

wherein V is —C(R$_6$)— or —S(O)$_2$—, or

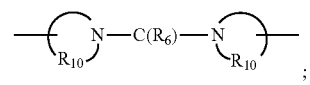

or
$R_3$ is —Z—R$_5$, and R$_5$ is

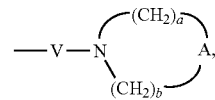

wherein V is —C(R$_6$)— or —S(O)$_2$—,
or

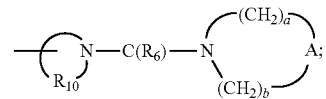

and
with the further proviso that Y can also be —O— when:
Y is bonded to R$_4$, and R$_4$ is selected from the group consisting of hydrogen, aryl, and heteroaryl, wherein aryl and heteroaryl can be unsubstituted or substituted by one or more substituents; or
Y is bonded to Z and X, and X is arylene or heteroarylene;
or a pharmaceutically acceptable salt thereof.

In one embodiment, the present invention provides a compound of Formula II:

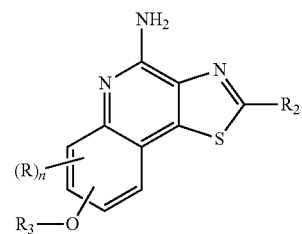

II wherein:
$R_3$ is selected from the group consisting of:
—Z—Y—R$_4$,
—Z—Y—X—Y—X—Y—R$_4$,
—Z—R$_5$,
—Z-Het,
—Z-Het'-R$_4$, and
—Z-Het'-Y—R$_4$;

R is selected from the group consisting of alkyl, alkoxy, hydroxy, halogen, and trifluoromethyl;

n is 0 or 1;

$R_2$ is selected from the group consisting of:
—$R_4$,
—X—Y'—$R_4$, and
—X—$R_5$';

Z is selected from the group consisting of alkylene, alkenylene, and alkynylene, wherein alkylene, alkenylene, and alkynylene can be optionally interrupted with one or more —O— groups;

Y is selected from the group consisting of:
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,
—O—$N(R_8)$-Q-,
—O—N=$C(R_4)$—,
—C(=N—O—$R_8$)—,
—CH(—N(—O—$R_8$)-Q-$R_4$)—,

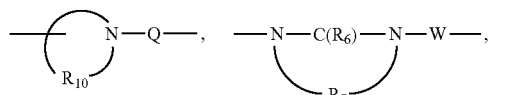

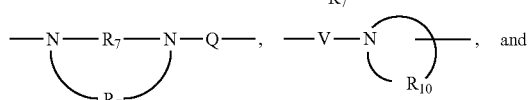

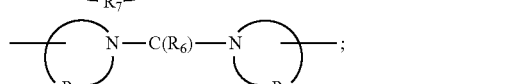

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y' is selected from the group consisting of:
—O—,
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,

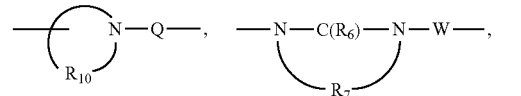

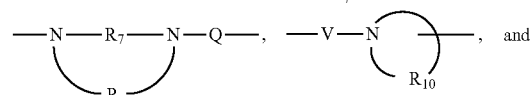

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

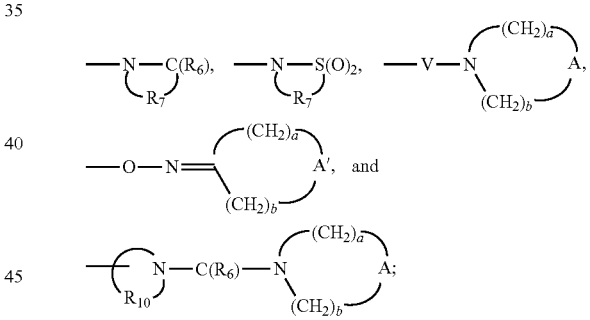

$R_5$' is selected from the group consisting of:

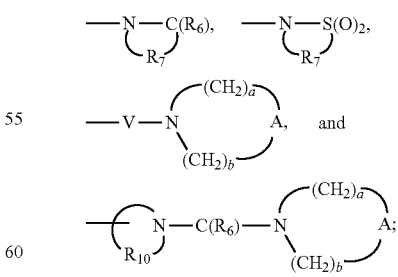

$R_6$ is selected from the group consisting of =O and =S;

$R_7$ is $C_{2-7}$ alkylene;

$R_8$ is selected from the group consisting of hydrogen, alkyl, hydroxyalkylenyl, alkoxyalkylenyl, arylalkylenyl, and heteroarylalkylenyl;

R$_9$ is selected from the group consisting of hydrogen and alkyl;

R$_{10}$ is C$_{3-8}$ alkylene;

A is selected from the group consisting of —O—, —CH$_2$—, —C(O)—, —S(O)$_{0-2}$—, and —N(R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when:
R$_3$ is —Z-Het, —Z-Het'-R$_4$, or —Z—Het'-Y—R$_4$, and Z is attached to an atom other than N in Het or Het'; or
R$_3$ is —Z—Y—X—Y—R$_4$, or —Z—Y—X—Y—X—Y—R$_4$, and the Y group bonded to Z is —S(O)$_2$—, —S(O)$_2$—N(R$_8$)—, —C(R$_6$)—, —C(R$_6$)—O—, —C(R$_6$)—N(R$_8$)—,

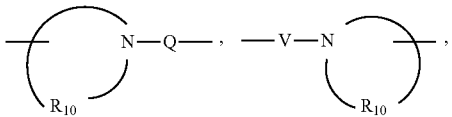

wherein V is —C(R$_6$)— or —S(O)$_2$—, or

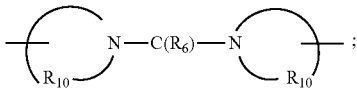

or
R$_3$ is —Z—R$_5$, and R$_5$ is

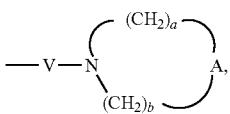

wherein V is —C(R$_6$)— or —S(O)$_2$—, or

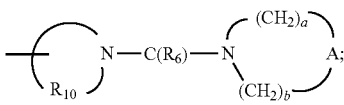

and
with the further proviso that Y can also be —O— when:
Y is bonded to R$_4$, and R$_4$ is selected from the group consisting of hydrogen, aryl, and heteroaryl, wherein aryl and heteroaryl can be unsubstituted or substituted by one or more substituents; or
Y is bonded to Z and X, and X is arylene or heteroarylene;
or a pharmaceutically acceptable salt thereof.

In one embodiment, the present invention provides a compound selected from the group consisting Formulas III, IV, V, and VI:

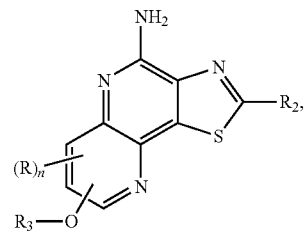

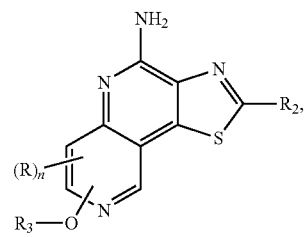

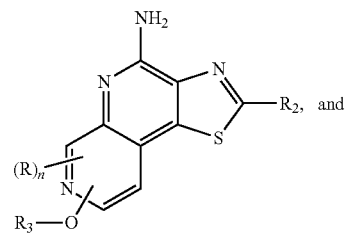

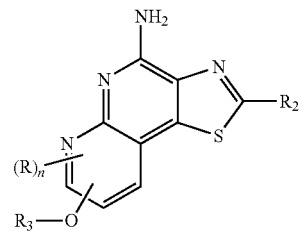

wherein:
R$_3$ is selected from the group consisting of:
—Z—Y—R$_4$,
—Z—Y—X—Y—R$_4$,
—Z—Y—X—Y—X—Y—R$_4$,
—Z—R$_5$,
—Z-Het,
—Z-Het'-R$_4$, and
—Z-Het'-Y—R$_4$;

R is selected from the group consisting of alkyl, alkoxy, hydroxy, halogen, and trifluoromethyl;

n is 0 or 1;

R$_2$ is selected from the group consisting of:
—R$_4$,
—X—R$_4$,
—X—Y'—R$_4$, and
—X—R$_5$';

Z is selected from the group consisting of alkylene, alkenylene, and alkynylene, wherein alkylene, alkenylene, and alkynylene can be optionally interrupted with one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N=C(R$_4$)—,
—C(=N—O—R$_8$)—,
—CH(—N(—O—R$_8$)-Q-R$_4$)—,

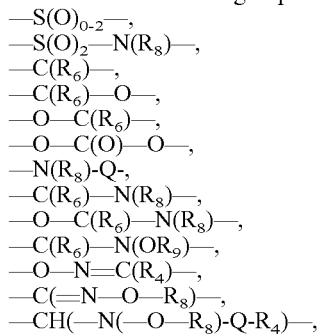

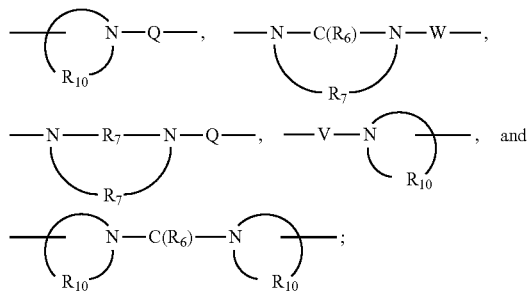

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

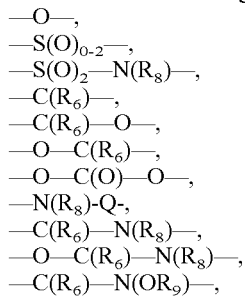

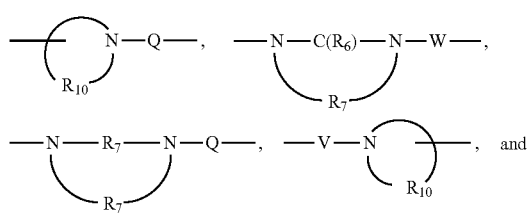

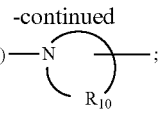

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

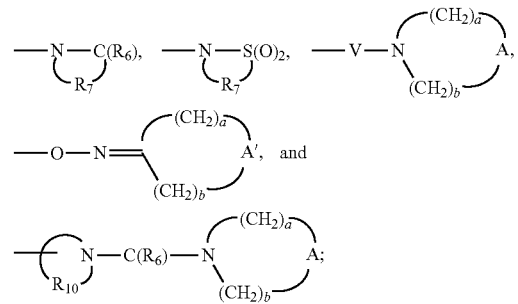

R$_5$' is selected from the group consisting of:

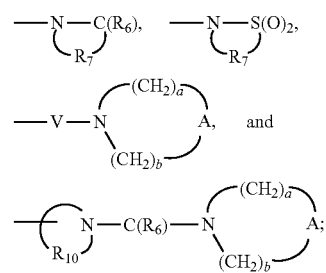

R$_6$ is selected from the group consisting of =O and =S;
R$_7$ is C$_{2-7}$ alkylene;
R$_8$ is selected from the group consisting of hydrogen, alkyl, hydroxyalkylenyl, alkoxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —CH$_2$—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when:
R$_3$ is —Z-Het, —Z-Het'-R$_4$, or —Z-Het'-Y—R$_4$, and Z is attached to an atom other than N in Het or Het'; or
R$_3$ is —Z—Y—R$_4$, —Z—Y—X—Y—R$_4$, or —Z—Y—X—Y—X—Y—R$_4$, and the Y group bonded to Z is —S(O)$_2$—, —S(O)$_2$—N(R$_8$)—, —C(R$_6$)—, —C(R$_6$)—O—, —C(R$_6$)—N(R$_8$)—,

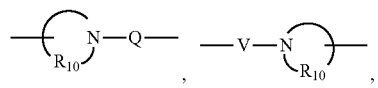

wherein V is —C(R$_6$)— or —S(O)$_2$—, or

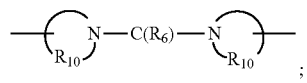

or
R$_3$ is —Z—R$_5$, and R$_5$ is

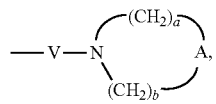

wherein V is —C(R$_6$)— or —S(O)$_2$—, or

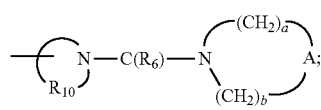

and
with the further proviso that Y can also be —O— when:
Y is bonded to R$_4$, and R$_4$ is selected from the group consisting of hydrogen, aryl, and heteroaryl, wherein aryl and heteroaryl can be unsubstituted or substituted by one or more substituents; or
Y is bonded to Z and X, and X is arylene or heteroarylene;
or a pharmaceutically acceptable salt thereof.

In one embodiment, the present invention provides a compound (which is a prodrug) of Formula VII:

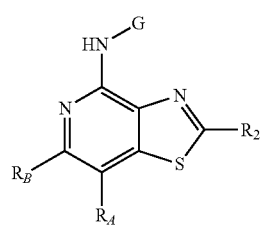

VII wherein:
R$_A$ and R$_B$ taken together form a fused benzene ring or fused pyridine ring wherein the benzene ring or pyridine ring is substituted by one —O—R$_3$ group, or substituted by one —O—R$_3$ group and one R group;
R$_3$ is selected from the group consisting of:
—Z—Y—R$_4$,
—Z—Y—X—Y—R$_4$,
—Z—Y—X—Y—X—Y—R$_4$,
—Z—R$_5$,
—Z-Het,
—Z-Het'-R$_4$, and
—Z-Het'-Y—R$_4$;
R is selected from the group consisting of alkyl, alkoxy, hydroxy, halogen, and trifluoromethyl;
G is selected from the group consisting of:
—C(O)—R',
α-aminoacyl,
α-aminoacyl-α-aminoacyl,
—C(O)—O—R',
—C(O)—N(R''')R',
—C(=NY$_1$)—R',
—CH(OH)—C(O)—OY$_1$,
—CH(OC$_{1-4}$ alkyl)Y$_0$,
—CH$_2$Y$_2$, and
—CH(CH$_3$)Y$_2$;
R' and R''' are independently selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R''' can also be hydrogen;
α-aminoacyl is an α-aminoacyl group derived from an amino acid selected from the group consisting of racemic, D-, and L-amino acids;
Y$_1$ is selected from the group consisting of hydrogen, C$_{1-6}$ alkyl, and benzyl;
Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl;
Y$_2$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;
R$_2$ is selected from the group consisting of:
—R$_4$,
—X—R$_4$,
—X—Y'—R$_4$, and
—X—R$_5$';
Z is selected from the group consisting of alkylene, alkenylene, and alkynylene, wherein alkylene, alkenylene, and alkynylene can be optionally interrupted with one or more —O— groups;
Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—, —C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

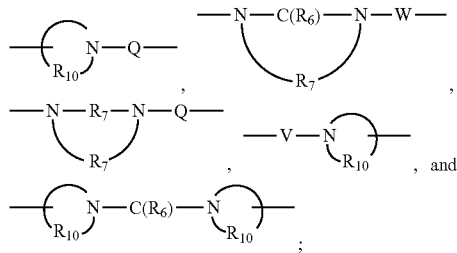

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

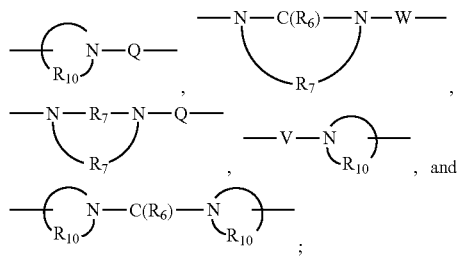

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and het-erocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

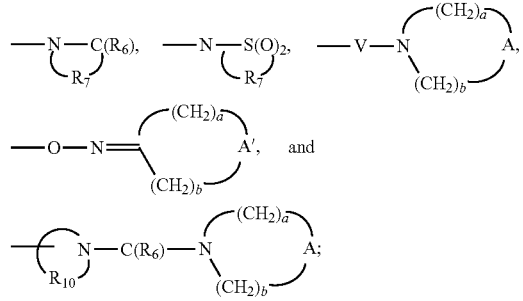

R$_5$' is selected from the group consisting of:

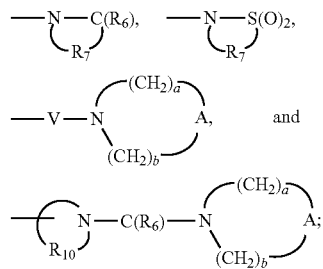

R$_6$ is selected from the group consisting of =O and =S;
R$_7$ is C$_{2-7}$ alkylene;
R$_8$ is selected from the group consisting of hydrogen, alkyl, hydroxyalkylenyl, alkoxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —CH$_2$—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
with the proviso that Z can also be a bond when:
R$_3$ is —Z-Het, —Z-Het'-R$_4$, or —Z-Het'-Y—R$_4$, and Z is attached to an atom other than N in Het or Het'; or
R$_3$ is —Z—Y—X—Y—R$_4$, or —Z—Y—X—Y—X—Y—R$_4$, and the Y group bonded to Z is —S(O)$_2$—, —S(O)$_2$—N(R$_8$)—, —C(R$_6$)—, —C(R$_6$)—O—, —C(R$_6$)—N(R$_8$)—,

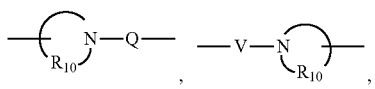

wherein V is —C(R₆)— or —S(O)₂—, or

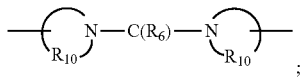

or

R₃ is —Z—R₅, and R₅ is

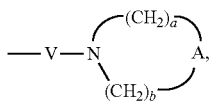

wherein V is —C(R₆)— or —S(O)₂—, or

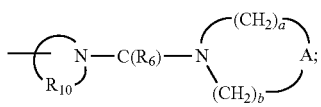

and with the further proviso that Y can also be —O— when:
Y is bonded to R₄, and R₄ is selected from the group consisting of hydrogen, aryl, and heteroaryl, wherein aryl and heteroaryl can be unsubstituted or substituted by one or more substituents; or
Y is bonded to Z and X, and X is arylene or heteroarylene;
or a pharmaceutically acceptable salt thereof.

In one embodiment, the present invention provides an intermediate compound of Formula X, which is also an IRM:

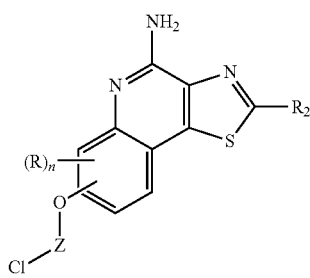

X wherein:
R is selected from the group consisting of alkyl, alkoxy, hydroxy, halogen, and trifluoromethyl;
n is 0 or 1;
R₂ is selected from the group consisting of:
—R₄,
—X—R₄,
—X—Y'—R₄, and
—X—R₅';

Z is selected from the group consisting of alkylene, alkenylene, and alkynylene, wherein alkylene, alkenylene, and alkynylene can be optionally interrupted with one or more —O— groups;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y' is selected from the group consisting of:
—O—,
—S(O)₀₋₂—,
—S(O)₂—N(R₈)—,
—C(R₆)—,
—C(R₆)—O—,
—O—C(R₆)—,
—O—C(O)—O—,
—N(R₈)-Q-,
—C(R₆)—N(R₈)—,
—O—C(R₆)—N(R₈)—,
—C(R₆)—N(OR₉)—,

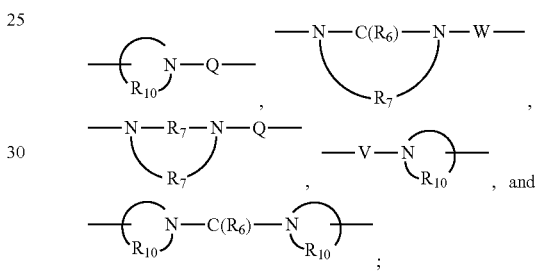

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R₅' is selected from the group consisting of:

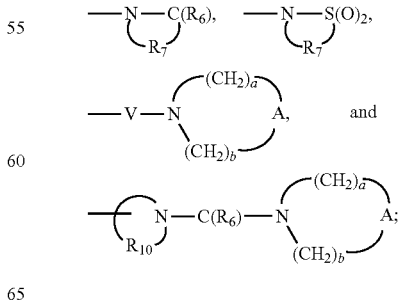

R₆ is selected from the group consisting of =O and =S;
R₇ is C₂₋₇ alkylene;

$R_8$ is selected from the group consisting of hydrogen, alkyl, hydroxyalkylenyl, alkoxyalkylenyl, arylalkylenyl, and heteroarylalkylenyl;

$R_9$ is selected from the group consisting of hydrogen and alkyl;

$R_{10}$ is $C_{3-8}$ alkylene;

A is selected from the group consisting of —O—, —CH$_2$—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7; or a pharmaceutically acceptable salt thereof.

In one embodiment, the present invention provides an intermediate compound of Formula XI, which is also an IRM:

wherein:

R is selected from the group consisting of alkyl, alkoxy, hydroxy, halogen, and trifluoromethyl;

n is 0 or 1;

$R_2$ is selected from the group consisting of:
—$R_4$,
—X—$R_4$,
—X—Y'—$R_4$, and
—X—$R_5$';

Z is selected from the group consisting of alkylene, alkenylene, and alkynylene, wherein alkylene, alkenylene, and alkynylene can be optionally interrupted with one or more —O— groups;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y' is selected from the group consisting of:
—O—,
—S(O)$_{0-2}$—,
—S(O)$_2$—N(R$_8$)—;
—C(R$_6$)—,
—C(R$_6$)—O—,
—O—C(R$_6$)—,
—O—C(O)—O—,
—N(R$_8$)-Q-,
—C(R$_6$)—N(R$_8$)—;
—O—C(R$_6$)—N(R$_8$)—,
—C(R$_6$)—N(OR$_9$)—, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$' is selected from the group consisting of:

$R_6$ is selected from the group consisting of =O and =S;

$R_7$ is $C_{2-7}$ alkylene;

$R_8$ is selected from the group consisting of hydrogen, alkyl, hydroxyalkylenyl, alkoxyalkylenyl, arylalkylenyl, and heteroarylalkylenyl;

$R_9$ is selected from the group consisting of hydrogen and alkyl;

$R_{10}$ is $C_{3-8}$ alkylene;

A is selected from the group consisting of —O—, —CH$_2$—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7; or a pharmaceutically acceptable salt thereof.

In one embodiment, the present invention provides an intermediate compound of Formula XII:

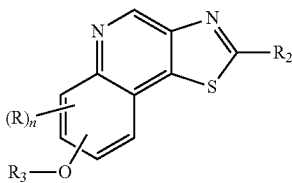

XII wherein:
R₃ is selected from the group consisting of:
—Z—Y—X—Y—R₄,
—Z—Y—X—Y—X—Y—R₄,
—Z—R₅,
—Z-Het,
—Z-Het'-R₄, and
—Z-Het'-Y—R₄;

R is selected from the group consisting of alkyl, alkoxy, hydroxy, halogen, and trifluoromethyl;

n is 0 or 1;

R₂ is selected from the group consisting of:
—R₄,
—X—R₄,
—X—Y'—R₄, and
—X—R₅';

Z is selected from the group consisting of alkylene, alkenylene, and alkynylene, wherein alkylene, alkenylene, and alkynylene can be optionally interrupted with one or more —O— groups;

Y is selected from the group consisting of:
—S(O)₀₋₂—,
—S(O)₂—N(R₈)—,
—C(R₆)—,
—C(R₆)—O—,
—O—C(R₆)—,
—O—C(O)—O—,
—N(R₈)-Q-,
—C(R₆)—N(R₈)—,
—O—C(R₆)—N(R₈)—,
—C(R₆)—N(OR₉)—,
—O—N(R₈)-Q-,
—O—N=C(R₄)—,
—C(=N—O—R₈)—,
—CH(—N(—O—R₈)-Q-R₄)—,

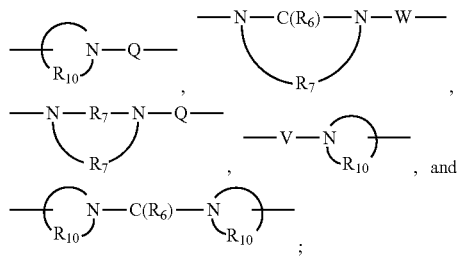

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y' is selected from the group consisting of:
—O—,
—S(O)₀₋₂—,
—S(O)₂—N(R₈)—,
—C(R₆)—,
—C(R₆)—O—,
—O—C(R₆)—,
—O—C(O)—O—,
—N(R₈)-Q-,
—C(R₆)—N(R₈)—,
—O—C(R₆)—N(R₈)—,
—C(R₆)—N(OR₉)—,

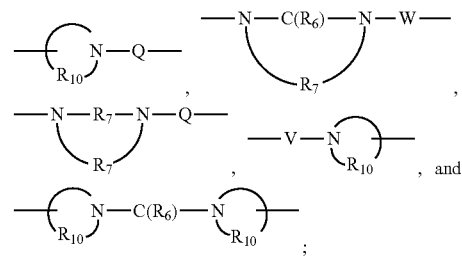

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

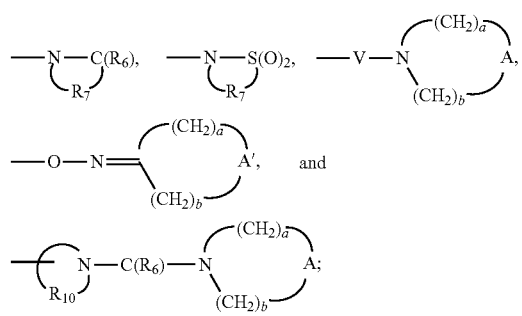

$R_5'$ is selected from the group consisting of:

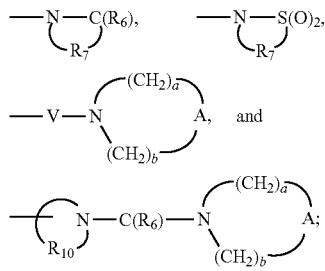

$R_6$ is selected from the group consisting of =O and =S;
$R_7$ is $C_{2-7}$ alkylene;
$R_8$ is selected from the group consisting of hydrogen, alkyl, hydroxyalkylenyl, alkoxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —CH$_2$—, —C(O)—, —S(O)$_{0-2}$—, and —N(R—$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7; with the proviso that Z can also be a bond when:
  $R_3$ is —Z-Het, —Z-Het'-R$_4$, or —Z-Het'-Y—R$_4$, and Z is attached to an atom other than N in Het or Het'; or
  $R_3$ is —Z—Y—X—Y—R$_4$, or —Z—Y—X—Y—X—Y—R$_4$, and the Y group bonded to Z is —S(O)$_2$—, —S(O)$_2$—N(R$_8$)—, —C(R$_6$)—, —C(R$_6$)—O—, —C(R$_6$)—N(R$_8$)—,

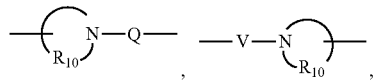

wherein V is —C(R$_6$)— or —S(O)$_2$—, or

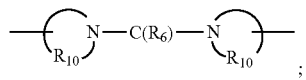

or
$R_3$ is —Z—R$_5$, and R$_5$ is

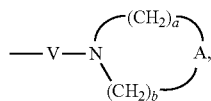

wherein V is —C(R$_6$)— or —S(O)$_2$—, or

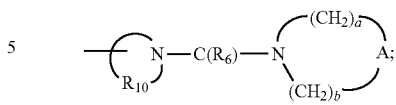

and
with the further proviso that Y can also be —O— when:
  Y is bonded to R$_4$, and R$_4$ is selected from the group consisting of hydrogen, aryl, and heteroaryl, wherein aryl and heteroaryl can be unsubstituted or substituted by one or more substituents; or
  Y is bonded to Z and X, and X is arylene or heteroarylene;
or a pharmaceutically acceptable salt thereof.

In one embodiment, the present invention provides an intermediate compound of Formula XIII:

XIII wherein:
$R_3$ is selected from the group consisting of:
  —Z—Y—R$_4$,
  —Z—Y—X—Y—R$_4$,
  —Z—R$_5$,
  —Z-Het,
  —Z-Het'-R$_4$, and
  —Z—Het'-Y—R$_4$;
R is selected from the group consisting of alkyl, alkoxy, hydroxy, halogen, and trifluoromethyl;
n is 0 or 1;
$R_2$ is selected from the group consisting of:
  —R$_4$,
  —X—Y'—R$_4$, and
  —X—R$_5'$;
Z is selected from the group consisting of alkylene, alkenylene, and alkynylene, wherein alkylene, alkenylene, and alkynylene can be optionally interrupted with one or more —O— groups;
Y is selected from the group consisting of:
  —S(O)$_{0-2}$—,
  —S(O)$_2$—N(R$_8$)—,
  —C(R$_6$)—,
  —C(R$_6$)—O—,
  —O—C(R$_6$)—,
  —O—C(O)—O—,
  —N(R$_8$)-Q-,
  —C(R$_6$)—N(R$_8$)—,
  —O—C(R$_6$)—N(R$_8$)—,
  —C(R$_6$)—N(OR$_9$)—,
  —O—N(R$_8$)-Q-,
  —O—N=C(R$_4$)—,
  —C(=N—O—R$_8$)—,
  —CH(—N(—O—R$_8$)-Q-R$_4$)—,

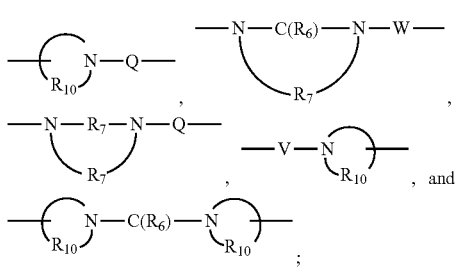

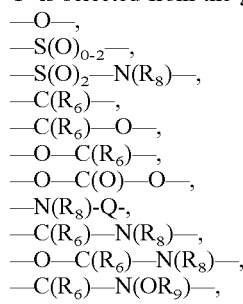

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

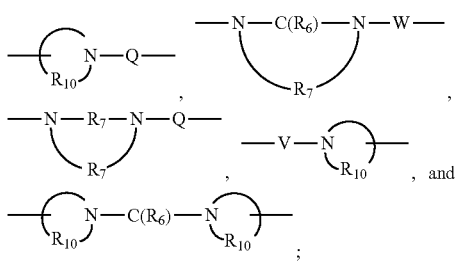

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

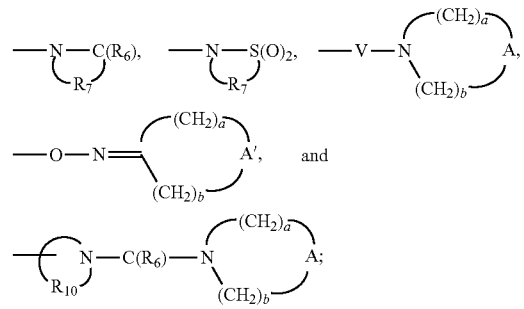

R$_5$' is selected from the group consisting of:

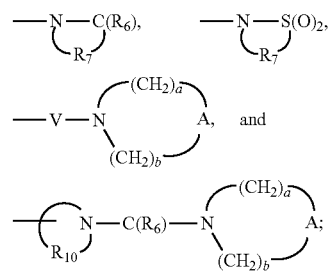

R$_6$ is selected from the group consisting of =O and =S;

R$_7$ is C$_{2-7}$ alkylene;

R$_8$ is selected from the group consisting of hydrogen, alkyl, hydroxyalkylenyl, alkoxyalkylenyl, arylalkylenyl, and heteroarylalkylenyl;

R$_9$ is selected from the group consisting of hydrogen and alkyl;

R$_{10}$ is C$_{3-8}$ alkylene;

A is selected from the group consisting of —O—, —CH$_2$—, —C(O)—, —S(O)$_{0-2}$—, and —N(R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when:

R$_3$ is —Z-Het, —Z-Het'-R$_4$, or —Z-Het'-Y—R$_4$, and Z is attached to an atom other than N in Het or Het'; or R$_3$ is —Z—Y—R$_4$, —Z—Y—X—Y—R$_4$, or —Z—Y—X—Y—X—Y—R$_4$, and the Y group bonded to Z is —S(O)$_2$—, —S(O)$_2$—N(R$_8$)—, —C(R$_6$)—, —C(R$_6$)—O—, —C(R$_6$)—N(R$_8$)—,

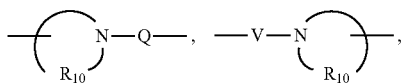

wherein V is —C(R$_6$)— or —S(O)$_2$—, or

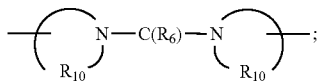

or

R$_3$ is —Z—R$_5$, and R$_5$ is

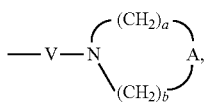

wherein V is —C(R$_6$)— or —S(O)$_2$—, or

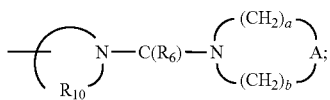

and
with the further proviso that Y can also be —O— when:
Y is bonded to R$_4$, and R$_4$ is selected from the group consisting of hydrogen, aryl, and heteroaryl, wherein aryl and heteroaryl can be unsubstituted or substituted by one or more substituents; or
Y is bonded to Z and X, and X is arylene or heteroarylene;
or a pharmaceutically acceptable salt thereof.

Herein, "non-interfering" means that the ability of the compound or salt, which includes a non-interfering substituent, to modulate the biosynthesis of one or more cytokines is not destroyed by the non-interfering substituent. Illustrative non-interfering R" groups include those described above for R$_2$.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo [3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene," and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R$_8$)—C(R$_6$)—N(R$_8$)— each R$_8$ group is independently selected. In another example, when an R$_2$ and an R$_3$ group both contain an $R_4$ group, each $R_4$ group is independently selected. In a further example, when more than one Y group is present and each Y group contains one or more $R_8$ groups, then each Y group is independently selected, and each $R_8$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Z, X, Y, Y', $R_A$, $R_B$, R, $R_2$, $R_3$, Q, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formulas I and VII, particularly embodiments of Formula I, $R_A$ and $R_B$ are taken together to form a fused benzene ring wherein the benzene ring is substituted by one —O—$R_3$ group, or substituted by one —O—$R_3$ group and one R group. In certain of these embodiments, the fused benzene ring is substituted by one —O—$R_3$ group.

For certain embodiments of Formulas I and VII, particularly embodiments of Formula I, $R_A$ and $R_B$ are taken together to form a fused pyridine ring wherein the pyridine ring is substituted by one —O—$R_3$ group, or substituted by one —O—$R_3$ group and one R group. In certain of these embodiments, the fused pyridine ring is substituted by one —O—$R_3$ group.

For certain embodiments, the compound selected from the group consisting of Formulas III, IV, V, and VI, or a pharmaceutically acceptable salt thereof is the compound of Formula III:

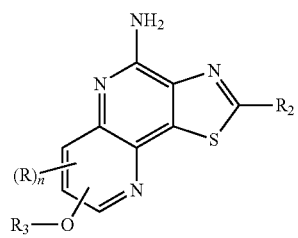

III or a pharmaceutically acceptable salt thereof.

For certain embodiments, n is 0 in the above embodiments of Formulas II, III, IV, V, and VI.

For certain embodiments, R is selected from the group consisting of alkyl, alkoxy, hydroxy, halogen, and trifluoromethyl.

For certain embodiments, R" is hydrogen or a non-interfering substituent.

For certain embodiments, R" is a non-interfering substituent.

For certain embodiments, R" is $R_2$; wherein $R_2$ is selected from the group consisting of —$R_4$, —X—$R_4$, —X—Y'—$R_4$, and —X—$R_5$'.

For certain embodiments, $R_2$ is selected from the group consisting of —$R_4$, —X—$R_4$, —X—Y'—$R_4$, and —X—$R_5$'.

For certain embodiments, including any one of the above embodiments wherein $R_2$ is present, $R_2$ is selected from the group consisting of hydrogen, alkyl, alkoxyalkylenyl, and hydroxyalkylenyl. For certain embodiments, $R_2$ is selected from the group consisting of hydrogen, alkyl, and alkoxyalkylenyl. For certain embodiments, $R_2$ is selected from the group consisting of alkyl and alkoxyalkylenyl. For certain embodiments, $R_2$ is selected from the group consisting of hydrogen, methyl, ethyl, propyl, butyl, ethoxymethyl, methoxymethyl, 2-methoxyethyl, hydroxymethyl, and 2-hydroxyethyl. For certain embodiments, $R_2$ is selected from the group consisting of methyl, ethyl, n-propyl, n-butyl, ethoxymethyl, methoxymethyl, and 2-methoxyethyl.

For certain embodiments, particularly embodiments of Formula X, n is 0 and $R_2$ is selected from the group consisting of hydrogen, alkyl, alkoxyalkylenyl, and hydroxyalkylenyl.

For certain embodiments, $R_3$ is selected from the group consisting of —Z—Y—$R_4$, —Z—Y—X—Y—$R_4$, —Z—Y—X—Y—X—Y—$R_4$, —Z—$R_5$, —Z-Het, —Z-Het'-$R_4$, and —Z-Het'-Y—$R_4$.

For certain embodiments, including any one of the above embodiments, $R_3$ is —Z—Y—$R_4$ or —Z—Y—X—Y—$R_4$. In certain of these embodiments, Y is —N($R_8$)-Q-,

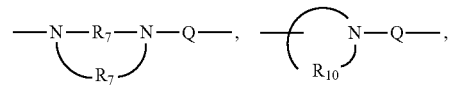

or —C(O)—; wherein Q is selected from the group consisting of a bond, —C(O)—, —C(O)—O—, —S(O)$_2$—, —C($R_6$)—N($R_8$)—, and —S(O)$_2$—N($R_8$)—; $R_6$ is selected from the group consisting of =O or =S; $R_7$ is $C_{2-3}$ alkylene; $R_8$ is selected from the group consisting of hydrogen, $C_{1-4}$ alkyl, and $C_{1-4}$ alkoxy$C_{1-4}$ alkylenyl; $R_{10}$ is $C_{3-6}$ alkylene; and $R_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, halogen, and aryl; wherein aryl, heteroaryl, and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents. In certain other of these embodiments, Y is —N($R_8$)-Q- or

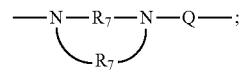

wherein Q is selected from the group consisting of a bond, —C(O)—, —C(O)—O—, —S(O)$_2$—, and —C(R$_6$)—N(R$_8$)—; R$_6$ is selected from the group consisting of =O or =S; R$_7$ is C$_{2-3}$ alkylene; R$_8$ is selected from the group consisting of hydrogen, C$_{1-4}$ alkyl, and C$_{1-4}$ alkoxyC$_{1-4}$ alkylenyl; and R$_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, and aryl; wherein aryl and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents. In certain of these embodiments, Y is —N(R$_8$)-Q-. In certain of these embodiments, Q is —C(O)—. In certain of these embodiments, Q is —S(O)$_2$—. In certain of these embodiments, Q is —C(R$_6$)—N(R$_8$)—. In certain of these embodiments, R$_4$ is C$_{1-4}$ alkyl and R$_8$ is hydrogen. In certain other of these embodiments, R$_4$ is phenyl that is unsubstituted or substituted by methoxy and R$_8$ is hydrogen. In certain embodiments, Q is a bond. In certain of these embodiments, R$_4$ is heterocyclyl that is unsubstituted or substituted by one or more alkyl groups, and R$_8$ is C$_{1-4}$ alkyl. In certain of these embodiments, R$_4$ is 1-methylpiperidin-4-yl and R$_8$ is methyl. In certain embodiments, R$_3$ is —Z—Y—R$_4$, wherein Y is —O— and R$_4$ is phenyl that is unsubstituted or substituted by one or more substituents selected from the group consisting of alkyl, halogen, cyano, alkoxy, nitro, and haloalkyl. In certain other embodiments, R$_3$ is —Z—Y—X—Y$_c$—R$_4$, wherein Y is —O—, X is phenylene, and Y$_c$—R$_4$ is selected from the group consisting of —C(O)-alkyl, —C(O)—O-alkyl, —S-alkyl, —NH—C(O)-alkyl, —C(O)—NH$_2$, and —S(O)$_2$—NH$_2$.

For certain embodiments, including any one of the above embodiments not excluding this definition, R$_3$ is —Z—R$_5$. In certain of these embodiments, R$_5$ is selected from the group consisting of:

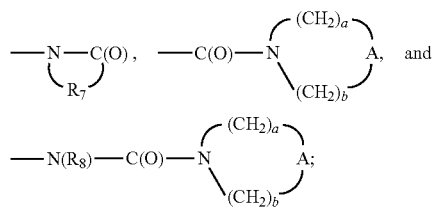

wherein A is —O—, —CH$_2$—, or —S(O)$_2$—; R$_7$ is C$_{2-4}$ alkylene; R$_8$ is hydrogen or C$_{1-4}$ alkyl; and a and b are each independently 1, 2, or 3. In certain embodiments, R$_5$ is

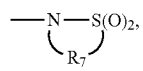

wherein R$_7$ is C$_{2-4}$ alkylene.

For certain embodiments, including any one of the above embodiments not excluding this definition, R$_3$ is —Z-Het or —Z-Het'-R$_4$. In certain of these embodiments, Het and Het' are, respectively, selected from the group consisting of the monovalent and divalent forms of tetrahydropyranyl, tetrahydrofuranyl, 1,3-dioxolanyl, azetidinyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substituents. For certain of these embodiments, Het and Het' are, respectively, selected from the group consisting of the monovalent and divalent forms of pyrrolidinyl, piperidinyl, and morpholinyl, each of which is unsubstituted or substituted by one or more substituents. For certain of these embodiments, Het is unsubstituted. For certain of these embodiments, Het' is unsubstituted. For certain of these embodiments, Het is substituted by one or more substituents selected from the group consisting of alkyl, hydroxy, hydroxyalkyl, hydroxyalkyleneoxyalkylenyl, and dialkylamino. For certain of these embodiments, R$_4$ is heterocyclyl. For certain of these embodiments, R$_4$ is selected from the group consisting of pyrrolidinyl and piperidinyl.

For certain embodiments, including any one of the above embodiments not excluding this definition, R$_3$ is —Z-Het'-Y—R$_4$. In certain of these embodiments, Het' is selected from the group consisting of the divalent form of tetrahydropyranyl, tetrahydrofuranyl, 1,3-dioxolanyl, pyrrolidinyl, piperidinyl, morpholinyl, thiomorpholinyl, thiazolidinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl. In certain of these embodiments, —Y—R$_4$ is selected from the group consisting of —C(O)-alkyl, —C(O)—O—H, —C(O)—O-alkyl, —C(O)—NH$_2$—, —C(O)—NH-alkyl, and —NH—C(O)-alkyl.

For certain embodiments, R$_3$ includes a substituted or unsubstituted thiazolo[4,5-c]quinolinyl group or a substituted or unsubstituted thiazolo[4,5-c]naphthyridinyl group and a connecting group such that the compound is a dimer. In certain of these embodiments, R$_3$ is —Z—Y$_a$—X—Y$_b$—R$_4$ wherein Y$_a$ is —N(R$_8$)-Q-, Y$_b$ is —O—, and R$_4$ is thiazolo[4,5-c]quinolinyl or thiazolo[4,5-c]naphthyridinyl. In certain of these embodiments, Q is —C(R$_6$)—N(R$_8$)—. In certain of these embodiments, the thiazolo[4,5-c]quinolinyl or thiazolo[4,5-c]naphthyridinyl group is substituted by alkyl and amino.

For certain embodiments, including any one of the above embodiments, Z is alkylene optionally interrupted with one or more —O— groups. In certain of these embodiments, Z is selected from the group consisting of C$_{1-6}$ alkylene and —CH$_2$CH$_2$—O—CH$_2$CH$_2$—.

For certain embodiments, including any one of the above embodiments permitted by the proviso for Formulas I through VII, more particularly for Formulas I through VI, and which do not exclude this definition, Z is a bond.

For certain embodiments, including any of the above embodiments, —O—R$_3$ is at the 7-position. For other embodiments, —O—R$_3$ is at the 8-position.

For certain embodiments, R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of alkyl, aryl, arylalkylenyl, alkylheteroarylenyl, heteroarylalkylenyl, heteroaryl, and heterocyclyl. For certain of these embodiments, alkyl is unsubstituted or substituted by one or more substituents selected from the group consisting of hydroxy, alkoxy, and aryl. For certain other of these embodiments, alkyl is unsubstituted or substituted by one or more substituents selected from the group consisting of hydroxy, alkoxy, halogen, and aryl. For certain of these embodiments, aryl and arylalkylenyl are unsubstituted or substituted by one or more substituents selected from the group consisting of alkyl, halogen, cyano, dialkylamino, and alkoxy. For certain of these embodiments, aryl, heteroaryl, and arylalkylenyl are unsubstituted or substituted by one or more substituents selected from the group consisting of alkyl, halogen, cyano, dialkylamino, and alkoxy. For certain of these embodiments, heterocyclyl is unsubstituted or substituted by one or more alkyl substituents.

For certain embodiments, $R_4$ is hydrogen or alkyl.

For certain embodiments, $R_4$ is alkyl.

For certain embodiments, $R_4$ is $C_{1-4}$ alkyl.

For certain embodiments, $R_4$ is heterocyclyl. For certain of these embodiments, $R_4$ is selected from the group consisting of pyrrolidinyl and piperidinyl.

For certain embodiments, $R_4$ is heterocyclyl that is unsubstituted or substituted by one or more alkyl groups. For certain of these embodiments, $R_4$ is 1-methylpiperidin-4-yl.

For certain embodiments, $R_4$ is phenyl that is unsubstituted or substituted by methoxy.

For certain embodiments, $R_4$ is heteroaryl.

For certain embodiments, $R_4$ is phenyl that is unsubstituted or substituted by one or more substituents selected from the group consisting of alkyl, halogen, cyano, alkoxy, nitro, and haloalkyl.

For certain embodiments, $R_5$ is selected from the group consisting of:

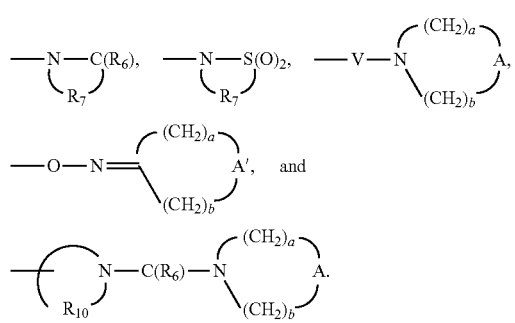

For certain embodiments, $R_5$ is selected from the group consisting of:

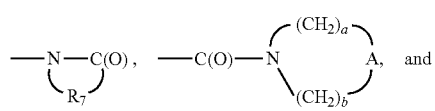

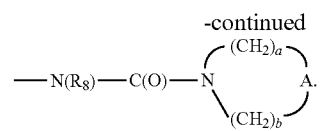

In certain of these embodiments A is —O—, —CH$_2$—, or —S(O)$_2$—; $R_7$ is $C_{2-4}$ alkylene; $R_8$ is hydrogen or $C_{1-4}$ alkyl; and a and b are each independently 1, 2, or 3. In certain of these embodiments a and b are each 2.

For certain embodiments, $R_5$ is

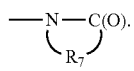

In certain of these embodiments, $R_7$ is $C_{2-4}$ alkylene. For certain embodiments, $R_5$ is

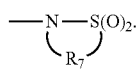

In certain of these embodiments, $R_7$ is $C_{2-4}$ alkylene.

For certain embodiments, $R_5'$ is selected from the group consisting of:

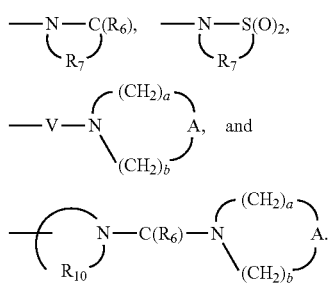

For certain embodiments, $R_6$ is selected from the group consisting of =O and =S.

For certain embodiments, $R_6$ is =O. For certain embodiments, $R_6$ is =S.

For certain embodiments, $R_7$ is $C_{2-7}$ alkylene.

For certain embodiments, $R_7$ is $C_{2-4}$ alkylene.

For certain embodiments, $R_7$ is $C_{2-3}$ alkylene. Preferably, in a ring of formula

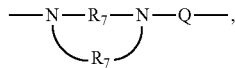

$R_7$ is $C_{2-3}$ alkylene.

For certain embodiments, $R_8$ is selected from the group consisting of hydrogen, alkyl, hydroxyalkylenyl, alkoxyalkylenyl, arylalkylenyl, and heteroarylalkylenyl.

For certain embodiments, $R_8$ is selected from the group consisting of hydrogen, $C_{1-4}$ alkyl, and $C_{1-4}$ alkoxy$C_{1-4}$ alkylenyl.

For certain embodiments, $R_8$ is hydrogen or $C_{1-4}$ alkyl.

For certain embodiments, $R_8$ is hydrogen.

For certain embodiments, $R_8$ is $C_{1-4}$ alkyl. For certain embodiments, $R_8$ is methyl.

For certain embodiments, $R_9$ is selected from the group consisting of hydrogen and alkyl.

For certain embodiments, $R_{10}$ is $C_{3-8}$ alkylene.
For certain embodiments, $R_{10}$ is $C_{4-6}$ alkylene.
For certain embodiments, $R_{10}$ is $C_{3-6}$ alkylene.
For certain embodiments, A is selected from the group consisting of —O—, —CH$_2$—, —C(O)—, —S(O)$_{0-2}$—, and —N(R$_4$)—.

For certain embodiments, A is —O—, —CH$_2$—, or —S(O)$_2$—.

For certain embodiments, A is —O— or —S(O)$_2$—.
For certain embodiments, A is —O—.
For certain embodiments, A' is selected from the group consisting of —O—, —S(O)$_{0-2}$—, —N(-Q-R$_4$)—, and —CH$_2$—.

In certain embodiments, A' is selected from the group consisting of —CH$_2$—, —S(O)$_2$—, and —O—.
In certain embodiments, A' is —CH$_2$—.
In certain embodiments, A' is —O—.
In certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—.

In certain embodiments, Q is selected from the group consisting of a bond, —C(O)—, —C(O)—O—, —S(O)$_2$—, —C(R$_6$)—N(R$_8$)—, and —S(O)$_2$—N(R$_8$)—.

In certain embodiments, Q is selected from the group consisting of a bond, —C(O)—, —C(O)—O—, —S(O)$_2$—, and —C(R$_6$)—N(R$_8$)—.

In certain embodiments, Q is —C(O)—.
In certain embodiments, Q is —S(O)$_2$—.
In certain embodiments, Q is —C(R$_6$)—N(R$_8$)—.
In certain embodiments, Q is a bond.
In certain embodiments, V is selected from the group consisting of —C(R$_6$)—, —O—C(R$_6$)—, —N(R$_8$)—C(R$_6$)—, and —S(O)$_2$—.

In certain embodiments, V is selected from the group consisting of —C(O)— and —N(R$_8$)—C(O)—.

In certain embodiments, W is selected from the group consisting of a bond, —C(O)—, and —S(O)$_2$—.

In certain embodiments, W is a bond or —C(O)—.
In certain embodiments, W is a bond.
In certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups. For certain embodiments, X is phenylene. For certain embodiments, X is alkylene.

In certain embodiments, Y is selected from the group consisting of —O—, —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—, —CH(—N(—O—R$_8$)-Q-R$_4$)—,

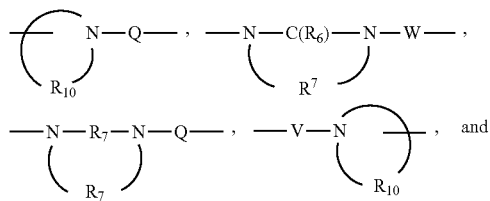

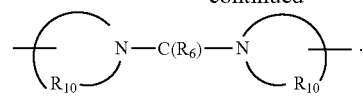

In certain embodiments, Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—, —CH(—N(—O—R$_8$)-Q-R$_4$)—,

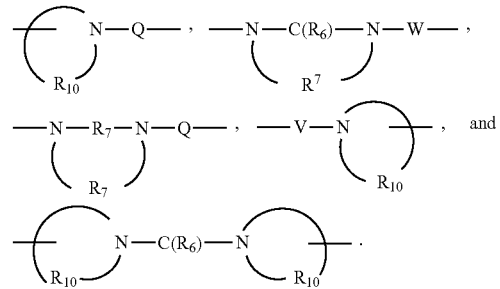

In certain of these embodiments, Y can also be —O—. For example, Y can also be —O— when Y is bonded to R$_4$, and R$_4$ is selected from the group consisting of hydrogen, aryl, and heteroaryl, wherein aryl and heteroaryl can be unsubstituted or substituted by one or more substituents. For these embodiments, the one or more substituents are independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, and (dialkylamino) alkyleneoxy. In another example, Y can also be —O— when Y is bonded to Z and X, and X is arylene or heteroarylene.

In certain embodiments, Y is —N(R$_8$)-Q-,

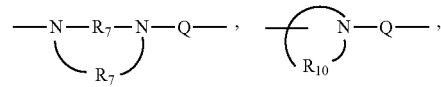

or —C(O)—. In certain of these embodiments, Q is selected from the group consisting of a bond, —C(O)—, —C(O)—O—, —S(O)$_2$—, —C(R$_6$)—N(R$_8$)—, and —S(O)$_2$—N(R$_8$)—; R$_6$ is selected from the group consisting of =O or =S; R$_7$ is C$_{2-3}$ alkylene; R$_8$ is selected from the group consisting of hydrogen, C$_{1-4}$ alkyl, and C$_{1-4}$ alkoxyC$_{1-4}$ alkylenyl; R$_{10}$ is C$_{3-6}$ alkylene; and R$_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, halogen, and aryl; wherein aryl, heteroaryl, and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents.

In certain embodiments, Y is —N(R$_8$)-Q- or

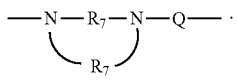

In certain of these embodiments, Q is selected from the group consisting of a bond, —C(O)—, —C(O)—O—, —S(O)$_2$—, and —C(R$_6$)—N(R$_8$)—; R$_6$ is selected from the group consisting of =O or =S; R$_7$ is C$_{2-3}$ alkylene; R$_8$ is selected from the group consisting of hydrogen, C$_{1-4}$ alkyl, and C$_{1-4}$ alkoxyC$_{1-4}$ alkylenyl; and R$_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, and aryl; wherein aryl and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents.

In certain embodiments, Y is —N(R$_8$)-Q-.

In certain embodiments, Y is selected from the group consisting of —C(O)—, —C(O)—O—, —C(O)—NH—, and —NH—C(O)—.

In certain embodiments, Y is —O—.

In certain embodiments, Y is selected from the group consisting of —C(O)—, —C(O)—O—, —S—, —NH—C(O)—, —C(O)—NH—, and —S(O)$_2$—NH—.

In certain embodiments, Y' is selected from the group consisting of —O—, —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

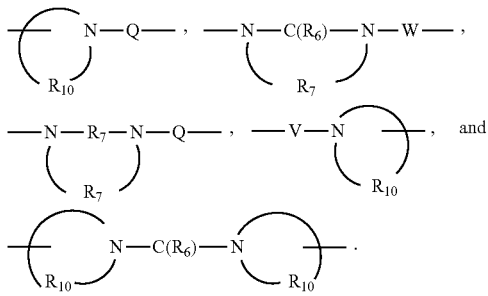

In certain embodiments, Z is selected from the group consisting of alkylene, alkenylene, and alkynylene, wherein alkylene, alkenylene, and alkynylene can be optionally interrupted with one or more —O— groups.

In certain embodiments, Z is alkylene optionally interrupted with one or more —O— groups.

In certain embodiments, Z is selected from the group consisting of C$_{1-6}$ alkylene and —CH$_2$CH$_2$—O—CH$_2$CH$_2$—. In certain of these embodiments, Z is selected from the group consisting of C$_{2-6}$ alkylene and —CH$_2$CH$_2$—O—CH$_2$CH$_2$—.

In certain embodiments, Z is a bond. For example, Z can be a bond when: R$_3$ is —Z-Het, —Z-Het'-R$_4$, or —Z-Het'-Y—R$_4$, and Z is attached to an atom other than N in Het or Het'; or R$_3$ is —Z—Y—R$_4$, —Z—Y—X—Y—R$_4$, or —Z—Y—X—Y—X—Y—R$_4$, and the Y group bonded to Z is —S(O)$_2$—, —S(O)$_2$—N(R$_8$)—, —C(R$_6$)—, —C(R$_6$)—O—, —C(R$_6$)—N(R$_8$)—,

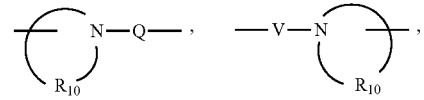

wherein V is —C(R$_6$)— or —S(O)$_2$—, or

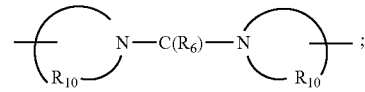

or
R$_3$ is —Z—R$_5$, and R$_5$ is

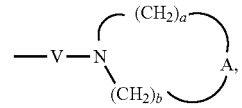

wherein V is —C(R$_6$)— or —S(O)$_2$—, or

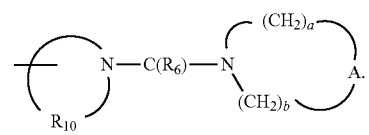

In certain embodiments, Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

In certain embodiments, Het is selected from the group consisting of tetrahydropyranyl, tetrahydrofuranyl, 1,3-dioxolanyl, azetidinyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substituents. For these embodiments, the one or more substituents are independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

In certain embodiments, Het is selected from the group consisting of pyrrolidinyl, piperidinyl, and morpholinyl, each of which is unsubstituted or substituted by one or more substituents. For these embodiments, the one or more substituents are independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

In certain embodiments, Het is substituted by one or more substituents selected from the group consisting of alkyl, hydroxyl, hydroxyalkyl, hydroxyalkyleneoxyalkylenyl, and dialkylamino.

In certain embodiments, Het is unsubstituted.

In certain embodiments, Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo.

In certain embodiments, Het' is selected from the group consisting of the divalent forms of tetrahydropyranyl, tetrahydrofuranyl, 1,3-dioxolanyl, azetidinyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substituents. For these embodiments, the one or more substituents are independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

In certain embodiments, Het' is selected from the group consisting of the divalent forms of tetrahydropyranyl, tetrahydrofuranyl, 1,3-dioxolanyl, pyrrolidinyl, piperidinyl, morpholinyl, thiomorpholinyl, thiazolidinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl, each of which is unsubstituted or substituted by one or more substituents. For these embodiments, the one or more substituents are independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

In certain embodiments, Het' is selected from the group consisting of the divalent forms of pyrrolidinyl, piperidinyl, and morpholinyl, each of which is unsubstituted or substituted by one or more substituents. For these embodiments, the one or more substituents are independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

In certain embodiments, Het' is unsubstituted (except by —$R_4$ or —Y—$R_4$).

In certain embodiments, a and b are independently integers from 1 to 6 with the proviso that a+b is ≤7.

In certain embodiments, a and b are each independently 1, 2, or 3.

In certain embodiments, a and b are each 2.

In certain embodiments, n is 0 or 1.

In certain embodiments, n is 0.

For certain embodiments of the compounds of Formulas I, II, III, IV, V, or VI, the —$NH_2$ group can be replaced by an —NH-G group, as shown in the compound of Formula VII, to form prodrugs. In such embodiments, G is selected from the group consisting of —C(O)—R', α-aminoacyl, α-aminoacyl-α-aminoacyl, —C(O)—O—R', —C(O)—N(R''')R', —C(=$NY_1$)—R', —CH(OH)—C(O)—$OY_1$, —CH($OC_{1-4}$ alkyl)$Y_0$, —$CH_2Y_2$, and —CH($CH_3$)$Y_2$. For these embodiments, R' and R''' are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$ with the proviso that R''' can also be hydrogen; α-aminoacyl is an α-aminoacyl group derived from an amino acid selected from the group consisting of racemic, D-, and L-amino acids; $Y_1$ is selected from the group consisting of hydrogen, $C_{1-6}$ alkyl, and benzyl; $Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and $Y_2$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, the present invention provides a pharmaceutical composition comprising a therapeutically effective amount of a compound or salt of any one of the above embodiments of Formulas I, II, III, IV, V, VI, VII, X, and XI and a pharmaceutically acceptable carrier.

For certain embodiments, the present invention provides a method of inducing cytokine biosynthesis in an animal comprising administering an effective amount of a compound or salt of any one of the above embodiments of Formulas I, II, III, IV, V, VI, VII, X, and XI, or a pharmaceutical composition comprising an effective amount of a compound or salt of any one of the above embodiments of Formulas I, II, III, IV, V, VI, VII, X, and XI to the animal.

For certain embodiments, the present invention provides a method of treating a viral disease in an animal comprising administering a therapeutically effective amount of a compound or salt of any one of the above embodiments of Formulas I, II, III, IV, V, VI, VII, X, and XI, or a pharmaceutical composition comprising a therapeutically effective amount of a compound or salt of any one of the above embodiments of Formulas I, II, III, IV, V, VI, VII, X, and XI to the animal.

For certain embodiments, the present invention provides a method of treating a neoplastic disease in an animal comprising administering a therapeutically effective amount of a compound or salt of any one of the above embodiments of Formulas I, II, III, IV, V, VI, VII, X, and XI, or a pharmaceutical composition comprising a therapeutically effective amount of a compound or salt of any one of the above embodiments of Formulas I, II, III, IV, V, VI, VII, X, and XI to the animal.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g. prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

For illustrative purposes, the reaction schemes depicted below provide potertial routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention or pharmaceutically acceptable salts thereof, as well as various intermediates related thereto. Such techniques may include, for example, all types of chromatography (high performance liquid chromatography (HPLC), column chromatography using common absorbents such as silica gel, and thin layer chromatography, recrystallization, and differential (i.e., liquid-liquid) extraction techniques.

Compounds of the invention can be prepared according to Reaction Scheme I, where R, $R_2$, $R_3$, and n are as defined above. In step (1) of Reaction Scheme I, a benzyloxyaniline of Formula XV is treated with the condensation product generated from 2,2-dimethyl-1,3-dioxane-4,6-dione (Meldrum's acid) and triethyl orthoformate to provide an imine of Formula XVI. The reaction can be conveniently carried out by adding a solution of a benzyloxyaniline of Formula XV to a heated mixture of Meldrum's acid and triethyl orthoformate and heating the reaction at an elevated temperature such as 45° C.

In step (2) of Reaction Scheme I, an imine of Formula XVI undergoes thermolysis and cyclization to provide a benzyloxyquinolin-4-ol of Formula XVII. The reaction can be conveniently carried out in a medium such as DOWTHERM A heat transfer fluid at a temperature in the range of 200° C. to 250° C.

In step (3) of Reaction Scheme I, the benzyloxyquinolin-4-ol of Formula XVII is nitrated under conventional nitration conditions to provide a benzyloxy-3-nitroquinolin-4-ol of Formula XVIII. The reaction can be conveniently carried out by adding nitric acid to the benzyloxyquinolin-4-ol of Formula XVII in a suitable solvent such as propionic acid and heating the mixture at an elevated temperature such as 125° C.

In step (4) of Reaction Scheme I, a benzyloxy-3-nitroquinolin-4-ol of Formula XVIII is reduced to provide a 3-amino-benzyloxyquinolin-4-ol of Formula XIX or a salt thereof, such as the hydrochloride salt thereof. The reaction can be carried out by hydrogenation using a heterogeneous hydrogenation catalyst such as platinum on carbon. The hydrogenation is conveniently carried out in a Parr apparatus in a suitable solvent such as N,N-dimethylformamide (DMF). The reaction can be carried out at room temperature.

In step (5) of Reaction Scheme I, a 3-amino benzyloxyquinolin-4-ol of Formula XIX is reacted with a carboxylic acid or an equivalent thereof to provide a compound of Formula XX. Suitable equivalents to carboxylic acid include acid anhydrides and acid chlorides. The selection of the carboxylic acid equivalent is determined by the desired substituent at $R_2$. For example, the use of butyryl chloride provides a compound in which $R_2$ is a propyl group; the use of ethoxyacetyl chloride provides a compound in which $R_2$ is an ethoxymethyl group. The reaction can be conveniently carried out by adding the acid chloride to a solution of a 3-aminobenzyloxyquinolin-4-ol of Formula XIX in a suitable solvent such as dichloromethane or acetonitrile in the presence of a tertiary amine such as triethylamine, pyridine, or 4-dimethylaminopyridine (DMAP) to afford an amide. The reaction can be carried out at or below room temperature. The amide of Formula XX can optionally be isolated and purified.

In step (6) of Reaction Scheme I, an amide of Formula XX is reacted with phosphorus pentasulfide to provide a benzyloxy[1,3]thiazolo[4,5-c]quinoline of Formula XXI. The reaction can be carried out by adding phosphorus pentasulfide to a solution or suspension of a compound of Formula XX in a suitable solvent such as pyridine and heating the resulting mixture at an elevated temperature, for example, the reflux temperature of the solvent.

In step (7) of Reaction Scheme I, a benzyloxy[1,3]thiazolo[4,5-c]quinoline of Formula XXI is oxidized to provide a benzyloxy[1,3]thiazolo[4,5-c]quinoline-5N-oxide of Formula XXII using a conventional oxidizing agent capable of forming N-oxides. The reaction can be conveniently carried out by adding 3-chloroperoxybenzoic acid to a solution of a compound of Formula XXI in a solvent such as dichloromethane or chloroform. The reaction can be carried out at room temperature.

In step (8) of Reaction Scheme I, a benzyloxy[1,3]thiazolo[4,5-c]quinoline-5N-oxide of Formula XXII is aminated to provide a benzyloxy[1,3]thiazolo[4,5-c]quinolin-4-amine of Formula XXIII. Step (8) can be carried out by the activation of an N-oxide of Formula XXII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction can be conveniently carried out by adding ammonium hydroxide followed by p-toluenesulfonyl chloride to a solution of the N-oxide of Formula XXII in a suitable solvent such as 1,2-dichloroethane at elevated temperature, for example 65° C. The reaction may also be carried out by adding ammonium hydroxide and p-toluenesulfonyl chloride to the reaction mixture from step (7) without isolating the N-oxide of Formula XXII.

Alternatively step (8) can be carried out by the reaction of a benzyloxy[1,3]thiazolo[4,5-c]quinoline-5N-oxide of Formula XXII with trichloroacetyl isocyanate followed by hydrolysis of the resulting intermediate to provide a benzyloxy[1,3]thiazolo[4,5-c]quinolin-4-amine of Formula XXIII. The reaction can be conveniently carried out in two steps by (i) adding trichloroacetyl isocyanate to a solution of the N-oxide of Formula XXII in a solvent such as dichloromethane and stirring at room temperature to provide an isolable amide intermediate. In step (ii), a solution of the intermediate in methanol is treated with a base such as sodium methoxide or ammonium hydroxide at room temperature.

In step (9) of Reaction Scheme I, the benzyl group of a benzyloxy[1,3]thiazolo[4,5-c]quinolin-4-amine of Formula XXIII is cleaved to provide a [1,3]thiazolo[4,5-c]quinolinol of Formula XXIV. The cleavage is conveniently carried out with an acid such as hydrogen bromide in a suitable solvent such as acetic acid at an elevated temperature, such as 65° C. Alternatively, the cleavage may be carried out on a Parr apparatus under hydrogenolysis conditions using a suitable heterogeneous catalyst such as palladium on carbon in a solvent such as ethanol.

In step (10) of Reaction Scheme I, a [1,3]thiazolo[4,5-c]quinolinol of Formula XXIV is converted to an ether-substituted [1,3]thiazolo[4,5-c]quinolin-4-amine of Formula II using a Williamson-type ether synthesis. The reaction is effected by treating a [1,3]thiazolo[4,5-c]quinolinol of Formula XXIV with an alkyl halide of Formula Halide-$R_3$ in the presence of a base. The reaction can be conveniently carried out by combining the alkyl halide with a [1,3]thiazolo[4,5-c]quinolinol of Formula XXIV in a solvent such as DMF in the presence of a suitable base such as cesium carbonate. The reaction can be carried out at ambient temperature or at an elevated temperature, for example 60° C. to 85° C. Alternatively, the reaction can be carried out by treating a solution of a [1,3]thiazolo[4,5-c]quinolinol of Formula XXIV in a solvent such as DMF with sodium hydride and then adding a reagent of Formula Halide-$R_3$.

Numerous reagents of Formulas Halide-Z—Y—$R_4$ and Halide-Z-Het, wherein Z, Y, $R_4$, and Het are as defined above, are commercially available. These include, for example, bromo-substituted ketones such as 2-bromoacetophenone and 2-bromo-1-(3-thienyl)-1-ethanone, bromo-substituted esters such as ethyl bromoacetate, and bromoalkyl-substituted heterocycles such as 2-(bromomethyl)tetrahydro-2H-pyran. Other reagents of Formulas Halide-Z—Y—$R_4$, Halide-Z—$R_5$, Halide-Z—Y—X—Y—$R_4$, and Halide-Z-Het, wherein Z, Y, X, $R_4$, $R_5$, and Het are as defined above, can be prepared using conventional synthetic methods; for example, a bromo-substituted acid halide of Formula ClC(O)—Z—Br or BrC(O)—Z—Br can be treated with a secondary amine in a suitable solvent such as dichloromethane to provide a variety of bromo-substituted amides of Formula Br—Z—C(O)—N($R_8$)—$R_4$,

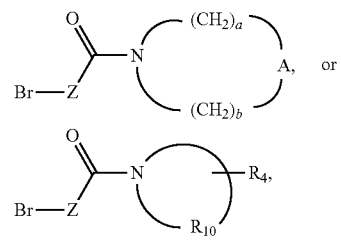

wherein $R_8$, $R_{10}$, A, a, and b are as defined above. The reaction can be run at a sub-ambient temperature such as –25° C.

Dimers of Formula II, wherein $R_3$ is —Z—O—$R_4$, wherein Z is selected from the group consisting of alkylene, alkenylene, and alkynylene wherein alkylene, alkenylene, and alkynylene can be optionally interrupted with one or more —O— groups, and $R_4$ is a [1,3]thiazolo[4,5-c]quinoline optionally substituted as defined in $R_4$ above, can be prepared in step (10) of Reaction Scheme I if half an equivalent of a dialkyl halide of Formula Halide-Z—Halide is used, and the reaction can be carried out according to the conditions described above.

Step (10) of Reaction Scheme I can alternatively be carried out by treating a [1,3]thiazolo[4,5-c]quinolinol of Formula XXIV with an alcohol of Formula HO—$R_3$ under Mitsunobu reaction conditions. Numerous alcohols of Formulas HO—Z—Y—$R_4$, HO—Z—$R_5$, and HO—Z-Het are commercially available, such as, for example, 1-(2-hydroxyethyl)pyrrolidin-2-one, 1-(3-hydroxypropyl)pyrrolidin-2-one, 3-(methylthio)propan-1-ol, and 3-hydroxytetrahydrofuran; other alcohols of Formula HO—$R_3$ can be prepared using conventional synthetic methods. The reaction can be conveniently carried out by out by adding triphenylphosphine and an alcohol of Formula HO—$R_3$ to a solution of a [1,3]thiazolo[4,5-c]quinolinol of Formula XXIV in a suitable solvent such as tetrahydrofuran and then slowly adding diisopropyl azodicarboxylate or diethyl azodicarboxylate. The reaction can be carried out at or below room temperature, for example, at 0° C.

Reaction Scheme I

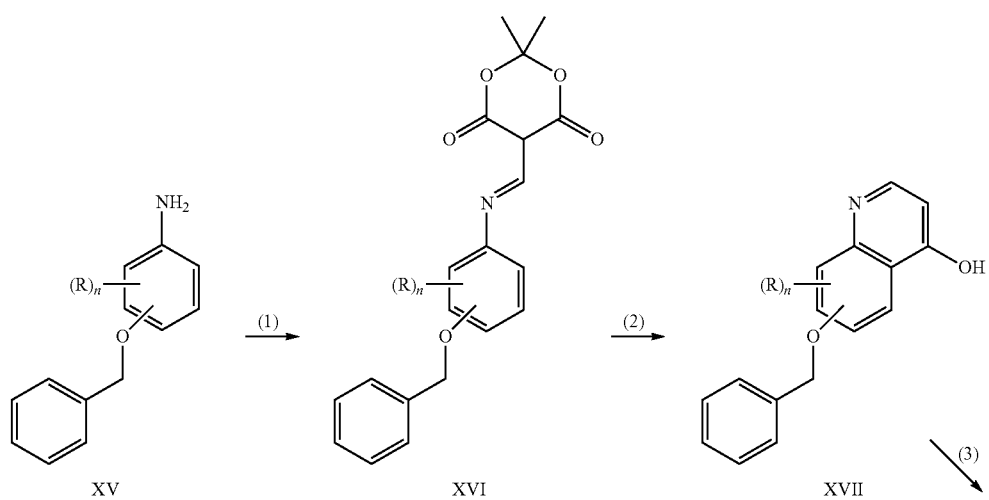

-continued

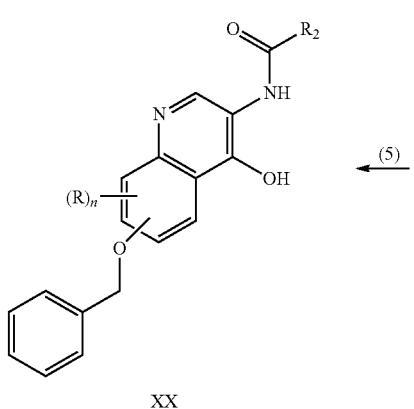
XX

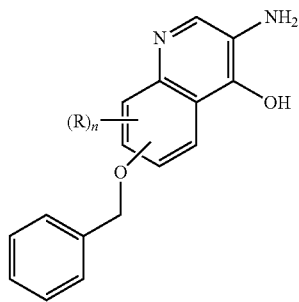
XIX

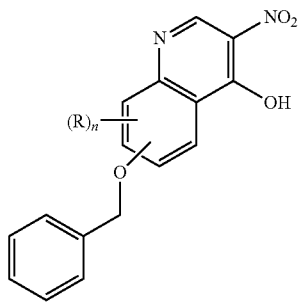
XVIII

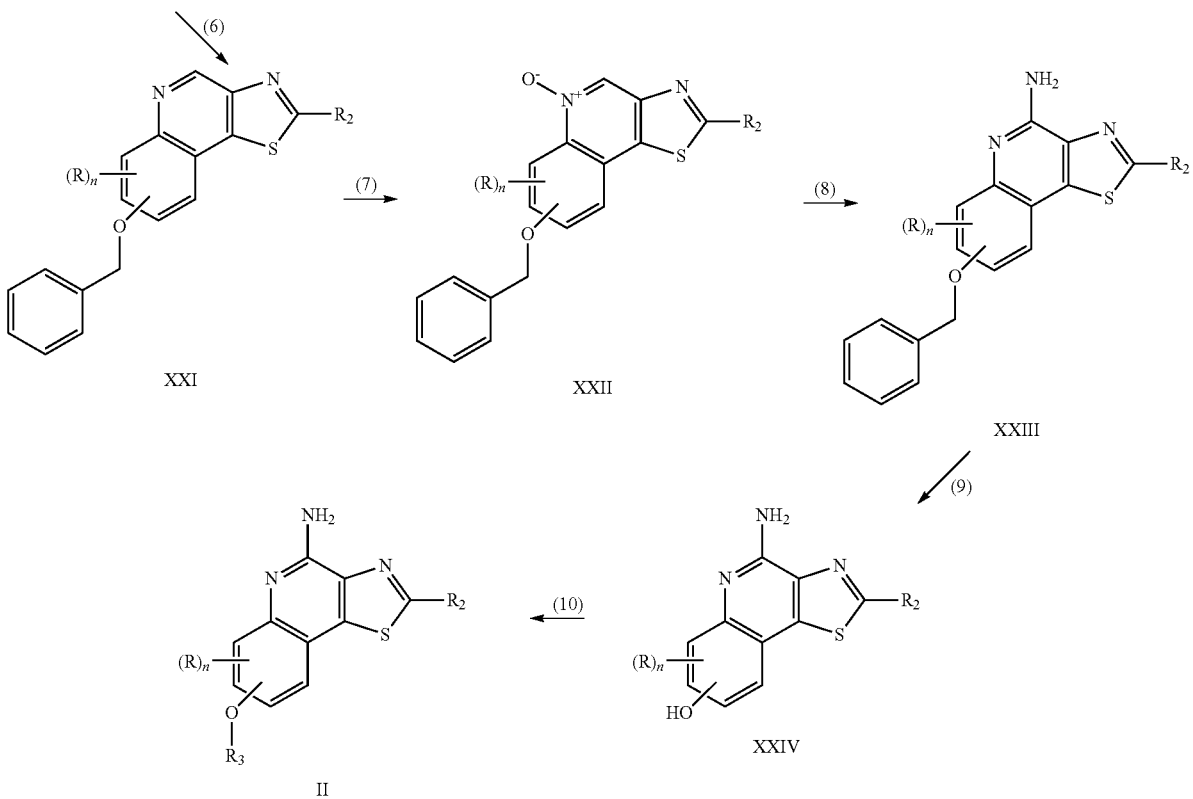
XXI          XXII          XXIII

XXIV

II

Compounds of the invention can be prepared according to Reaction Scheme II, where R, $R_2$, $R_3$, and n are as defined above. In step (1) of Reaction Scheme II, the benzyl group of a benzyloxy[1,3]thiazolo[4,5-c]quinoline of Formula XXI is cleaved to provide a [1,3]thiazolo[4,5-c]quinolinol of Formula XXV. The reaction can be carried out as described in step (9) of Reaction Scheme I.

In step (2) of Reaction Scheme II, a [1,3]thiazolo[4,5-c]quinolinol of Formula XXV is converted to an ether-substituted [1,3]thiazolo[4,5-c]quinoline of Formula XII. The reaction can be carried out using one of the methods described in step (10) of Reaction Scheme I.

In steps (3) and (4) of Reaction Scheme II, an ether-substituted [1,3]thiazolo[4,5-c]quinoline of Formula XII is oxidized to afford a [1,3]thiazolo[4,5-c]quinoline-5N-oxide of Formula XXVI, which is aminated to provide a [1,3]thiazolo[4,5-c]quinolin-4-amine of Formula II. Steps (3) and (4) can be carried out as described in steps (7) and (8), respectively, of Reaction Scheme I.

Synthetic transformations can be made at $R_2$ in compounds of Formulas XXI, XXIII, XXIV, XXV, XII, or II, shown in Reaction Scheme I or II, if, for example, the carboxylic acid or equivalent thereof used in step (5) of Reaction Scheme I contains a protected hydroxy or amino group. Some acid chlorides of this type, for example acetoxyacetyl chloride, are commercially available. Others can be prepared by known synthetic methods. A protected hydroxy or amino group thus installed at $R_2$ can then be deprotected by a variety of methods well-known to one of skill in the art. For example, an acetate group, installed by using acetoxyacetyl chloride as the carboxylic acid equivalent in step (5) of Reaction Scheme I, is readily hydrolyzed under basic conditions to provide a hydroxy group. The resulting hydroxy group can then be oxidized to an aldehyde or carboxylic acid or converted to a leaving group such as, for example, a chloro group using thionyl chloride or a trifluoromethanesulfonate group using trifluoromethanesulfonic anhydride. The resulting leaving group can then be displaced by a variety of nucleophiles. Sodium azide can be used as the nucleophile to install an azide group, which can then be reduced to an amino group using heterogeneous hydrogenation conditions. The amino group can then be converted to an amide, sulfonamide, sulfamide, or urea using one of the many methods described below in step (7) of Reaction Scheme IV. A leaving group at $R_2$, such as a chloro or trifluoromethanesulfonate group, can also be displaced with a secondary amine, a substituted phenol, or a mercaptan under the conditions described below in step (2) of Reaction Scheme VI to provide a variety of compounds. For other examples of the installation of a variety of $R_2$ groups, see U.S. Pat. No. 6,110,929 (Gerster et al.).

A hydroxyalkylenyl group can also be introduced at $R_2$ by the demethylation of a methoxyalkylenyl group, which can group. In another example, an $R_3$ group in a compound of Formula II may be —Z—Y—$R_4$, wherein Y is —C(O)—. A ketone of this formula can then be converted to an oxime by adding an aqueous solution of a hydroxylamine salt of formula $NH_2OR_8 \cdot HCl$ to a solution of the ketone in a suitable solvent such as methanol or ethanol and then adding a base such as sodium hydroxide and heating at an elevated temperature to provide a compound of the invention, wherein $R_3$ is —Z—Y—$R_4$ where Y is —C(=N—$OR_8$)—, and $R_4$ and $R_8$ are as defined above. The oxime so prepared may be reduced with sodium cyanoborohydride in a mixture of ethanol or methanol in acetic acid to provide a hydroxylamine, which may be treated with one of numerous acid chlorides, sulfonyl chloride, isocyanates, carbamoyl chloride, or sulfamoyl chlorides using one of the methods described in step (7) of Reaction Scheme IV below to provide a compound of the invention wherein $R_3$ is —Z—Y—$R_4$ where Y is —CH(—N—($OR_8$)-Q-$R_4$)—, and Q, $R_4$, and $R_8$ are as defined above.

Reaction Scheme II

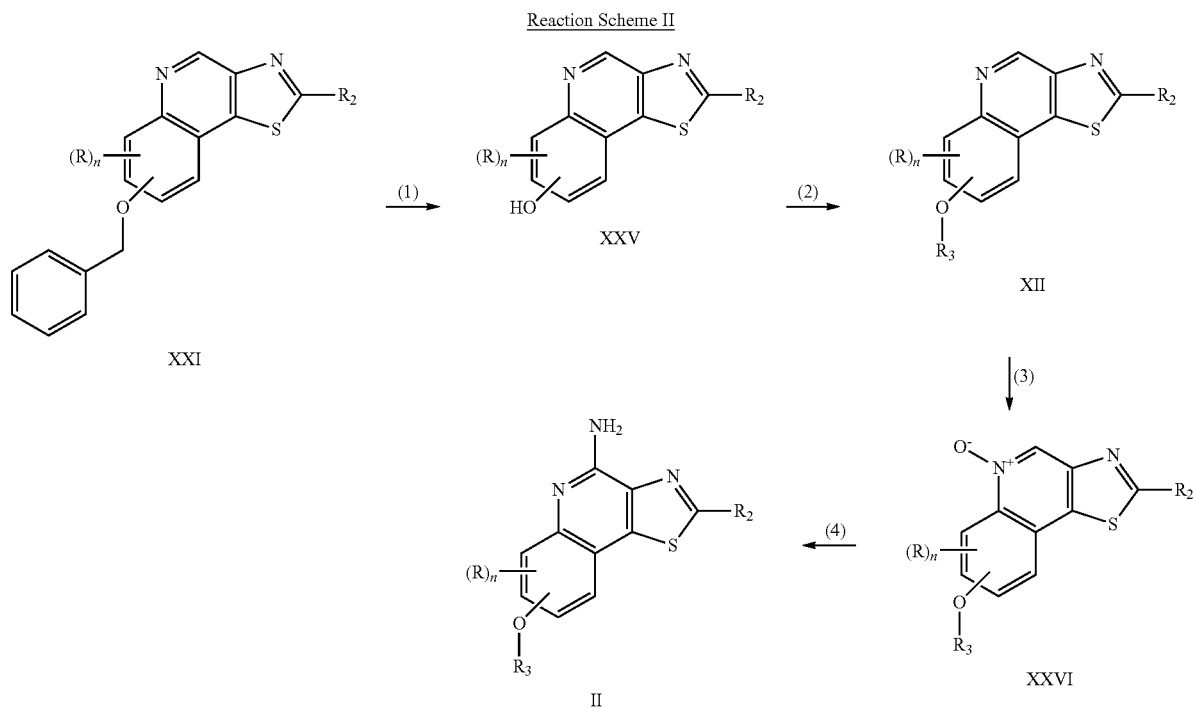

be installed by using a methoxy-substituted carboxylic acid equivalent, for example, methoxyacetyl chloride and 2-methoxypropionyl chloride, in step (5) of Reaction Scheme I. The demethylation can be carried out by treating a compound of Formula II wherein $R_2$ is a methoxyalkylenyl group with boron tribromide in a suitable solvent such as dichloromethane at a sub-ambient temperature such as 0° C.

Synthetic elaborations can also be carried out at the $R_3$ group in compounds prepared in either Reaction Scheme I or II. For example, an $R_3$ group in a compound of Formula XII may contain a —S— functional group, which can be oxidized to —$S(O)_2$— in step (3) of Reaction Scheme II using an excess of the oxidizing agent. Step (4) of Reaction Scheme II may then be carried out to provide a compound of Formula II, wherein $R_3$ contains a —$S(O)_2$— functional Compounds of the invention can be prepared according to Reaction Scheme III where R, $R_2$, $R_3$, and n are as defined above. Reaction Scheme III is analogous to Reaction Scheme I, with a benzyloxypyridine of Formula XXVII used as the starting material in Reaction Scheme III instead of a benzyloxyaniline of Formula XV. Benzyloxypyridines of Formula XXVII can be prepared using conventional synthetic methods; see for example, Holladay et al., *Biorg. Med. Chem. Lett.*, 8, pp. 2797-2802, (1998). Isomers of the compounds of Formula XXVII and Formula XXIX, wherein N is at a different position in the pyridine ring, can also be synthesized and can be used in Reaction Scheme III to prepare compounds of the invention. Steps (1) through (10) of Reaction Scheme III can be run using the same conditions described in steps (1) through (10) of Reaction Scheme I.

Reaction Scheme III
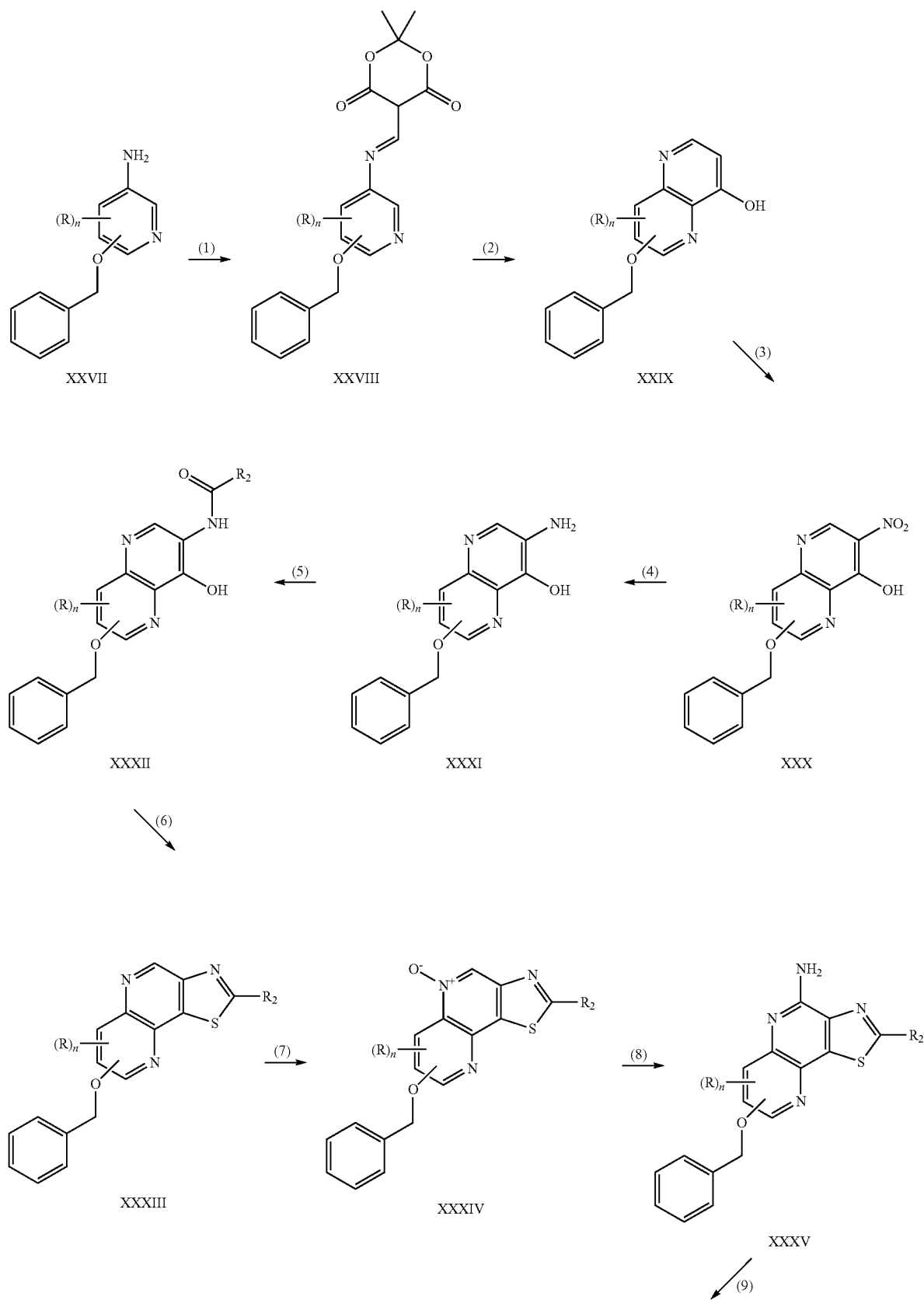

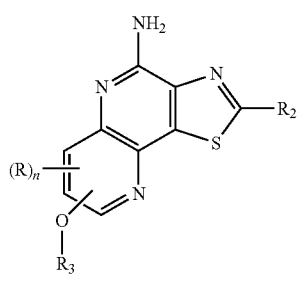

III

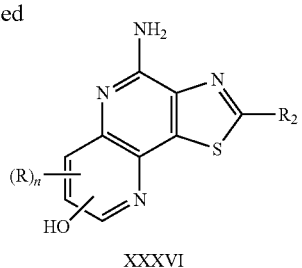

XXXVI

For some embodiments, compounds of the invention can be prepared according to Reaction Scheme IV, where R, $R_2$, $R_8$, and n are defined as above; Z is selected from the group consisting of alkylene, alkenylene, and alkynylene wherein alkylene, alkenylene, and alkynylene can be optionally interrupted with one or more —O— groups; and $R_{3a}$ is —Z—N($R_8$)-Q-$R_4$ or

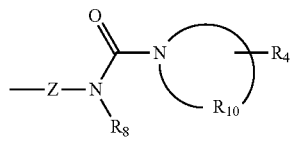

with $R_8$, $R_{10}$, Q, and $R_4$ as defined above; —Z—$R_5$, wherein $R_5$ is

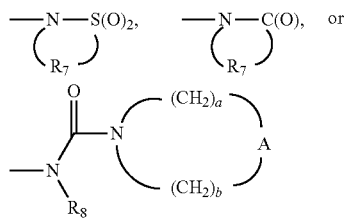

with A, a, b, $R_7$, and $R_8$ as defined above; or —Z—[N($R_8$)-Q]—X—O—$R_4$ or —Z—[N($R_8$)-Q]—X—[V—N($R_8$)]—X—O—$R_4$, wherein X and V are as defined above, and $R_4$ is a [1,3]thiazolo[4,5-c]quinoline optionally substituted as defined in $R_4$ above.

In step (1) of Reaction Scheme IV, the amine of an amino alcohol of Formula XXXVII is protected with a tert-butoxy carbonyl (Boc) group to provide a hydroxyalkylcarbamate of Formula XXXVIII. Numerous amino alcohols of Formula XXXVII are commercially available; others can be prepared using known synthetic methods. The reaction can be conveniently carried out by treating the amino alcohol of Formula XXXVII with di-tert-butyl dicarbonate optionally in the presence of a base such as aqueous sodium hydroxide. The reaction can be run at room temperature in a suitable solvent such as tetrahydrofuran or dichloromethane.

In step (2) of Reaction Scheme IV, a hydroxyalkylcarbamate of Formula XXXVIII is converted to an iodoalkylcarbamate of Formula XXXIX using conventional methods. The reaction can be conveniently carried out by treating the hydroxyalkylcarbamate of Formula XXXVIII with a solution of iodine, triphenylphosphine, and imidazole. The reaction can be run at room temperature in a suitable solvent such as dichloromethane or solvent mixture such as diethyl ether/acetonitrile.

In step (3) of Reaction Scheme IV, a [1,3]thiazolo[4,5-c]quinolinol of Formula XXV is treated with an iodoalkylcarbamate of Formula XXXIX to provide an ether-substituted [1,3]thiazolo[4,5-c]quinoline of Formula XL. The reaction can be carried out according to the Williamson conditions described in step (10) of Reaction Scheme I.

In steps (4) and (5) of Reaction Scheme IV, a [1,3]thiazolo[4,5-c]quinoline of Formula XL is oxidized to a [1,3]thiazolo[4,5-c]quinoline-5N-oxide of Formula XLI, which is aminated to provide a [1,3]thiazolo[4,5-c]quinolin-4-amine of Formula XLII, which is a subgenus Formulas I and II. Steps (4) and (5) of Reaction Scheme IV can be carried out as described for steps (7) and (8), respectively, of Reaction Scheme I. In step (5), the preferred conditions for amination are the activation of an N-oxide of Formula XLI by conversion to an ester and then reacting the ester with an aminating agent. Step (5) is conveniently carried out by adding ammonium hydroxide to a solution of the N-oxide of Formula XLI in a suitable solvent such as 1,2-dichloroethane and then adding p-toluenesulfonyl chloride and stirring at an elevated temperature such as 65° C.

In step (6) of Reaction Scheme IV, the Boc protecting group of a [1,3]thiazolo[4,5-c]quinolin-4-amine of Formula XLII is removed to provide an amino-substituted [1,3]thiazolo[4,5-c]quinolin-4-amine of Formula XLIII, which is a subgenus of Formulas I and II. The reaction can be conveniently carried out by adding a solution of hydrochloric acid in ethanol to a [1,3]thiazolo[4,5-c]quinolin-4-amine of Formula XLII. The reaction can be carried out at an elevated temperature, for example, the reflux temperature of the solvent.

In step (7) of Reaction Scheme IV, an amino-substituted [1,3]thiazolo[4,5-c]quinolin-4-amine of Formula XLIII is converted to a [1,3]thiazolo[4,5-c]quinolinyl compound of Formula IIa, a subgenus of Formulas I and II, using conventional methods. For example, an amino-substituted [1,3]thiazolo[4,5-c]quinolin-4-amine of Formula XLIII can react with an acid chloride of Formula $R_4C(O)Cl$ to provide a compound of Formula IIa in which $R_{3a}$ is —Z—N($R_8$)—C(O)—$R_4$. In addition, a [1,3]thiazolo[4,5-c]quinolin-4-amine of Formula XLIII can react with sulfonyl chloride of Formula $R_4S(O)_2Cl$ or a sulfonic anhydride of Formula $(R_4S(O)_2)_2O$ to provide a compound of Formula IIa in which $R_{3a}$ is —Z—N($R_8$)—S(O)$_2$—$R_4$. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction can be conveniently carried out by adding the acid chloride of Formula R₄C(O)Cl, sulfonyl chloride of Formula R₄S(O)₂Cl, or sulfonic anhydride of Formula (R₄S(O)₂)₂O to a solution of the amino-substituted [1,3]thiazolo[4,5-c]quinolin-4-amine of Formula XLIII in a suitable solvent such as chloroform, dichloromethane, N,N-dimethylacetamide (DMA), or 1-methyl-2-pyrrolidinone. Optionally a base such as triethylamine, pyridine, or N,N-diisopropylethylamine, or catalytic DMAP, or a combination thereof can be added. The reaction can be carried out at room temperature or initially at a sub-ambient temperature such as 0° C. and then warming to room temperature.

Compounds of Formula IIa where $R_{3a}$ is —Z—$R_5$ and $R_5$ is

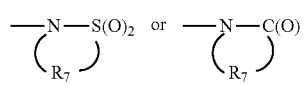

can be prepared by treating an amino-substituted [1,3]thiazolo[4,5-c]quinolin-4-amine of Formula XLIII, wherein $R_8$ is hydrogen, with a chloroalkanesulfonyl chloride of Formula Cl—$R_7$S(O)₂Cl or a chloroalkan.oyl chloride of Formula Cl—$R_7$C(O)Cl. The reaction can be conveniently carried out by adding the chloroalkanesulfonyl chloride or chloroalkanoyl chloride to a solution of the amino-substituted [1,3]thiazolo[4,5-c]quinolin-4-amine of Formula XLIII in a suitable solvent such as chloroform at ambient temperature. The isolable intermediate chloroalkanesulfonamide or chloroalkanamide can then be treated with a base such as 1,8-diazabicyclo[5.4.0]undec-7-ene or sodium hydride in a suitable solvent such as DMF to effect the cyclization.

Ureas of Formula IIa, where $R_{3a}$ is —Z—N($R_8$)-Q-$R_4$, Q is —C($R_6$)—NH—W—, $R_6$ is =O, and W is a bond, can be prepared by reacting an amino-substituted [1,3]thiazolo[4,5-c]quinolin-4-amine of Formula XLIII with isocyanates of Formula $R_4$N=C=O. Numerous isocyanates of Formula $R_4$N=C=O are commercially available; others can be readily prepared using known synthetic methods. The reaction can be conveniently carried out by adding the isocyanate of Formula $R_4$N=C=O to a solution of the amino-substituted [1,3]thiazolo[4,5-c]quinolin-4-amine of Formula XLIII in a suitable solvent such as dichloromethane, chloroform, or DMA. Optionally a base such as triethylamine can be added. The reaction can be carried out at room temperature or initially at a sub-ambient temperature such as 0° C. and warming to room temperature. Alternatively, a compound of Formula XLIII can be treated with an isocyanate of Formula $R_4$(CO)N=C=O, a thioisocyanate of Formula $R_4$N=C=S, a sulfonyl isocyanate of Formula $R_4$S(O)₂N=C=O, or a carbamoyl chloride of Formula $R_4$N—($R_8$)—C(O)Cl,

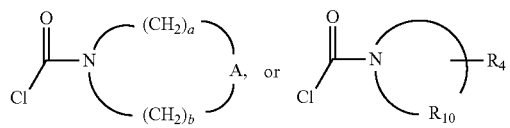

to provide a compound of Formula IIa, where $R_{3a}$ is —Z—N($R_8$)-Q-$R_4$,

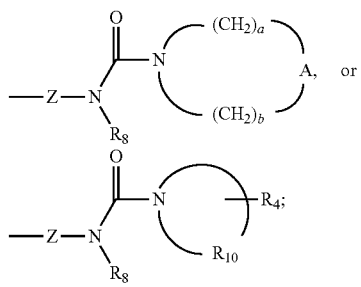

wherein Q is —C($R_6$)—N($R_8$)—W—, where $R_6$, $R_8$, and W are defined as above.

Sulfamides of Formula IIa, where $R_{3a}$ is —Z—N($R_8$)—S(O)₂—N($R_8$)—$R_4$ can be prepared by reacting a compound of Formula XLIII with sulfuryl chloride to generate a sulfamoyl chloride in situ, and then reacting the sulfamoyl chloride with an amine of Formula HN($R_8$)$R_4$. Alternatively, sulfamides of Formula IIa can be prepared by reacting a compound of Formula XLIII with a sulfamoyl chloride of Formula $R_4$($R_8$)N—S(O)₂Cl. Many amines of Formula HN($R_8$)$R_4$ and some sulfamoyl chlorides of Formula $R_4$($R_8$)N—S(O)₂Cl are commercially available; others can be prepared using known synthetic methods.

Compounds of Formula IIa, wherein $R_{3a}$ is —Z—N($R_8$)—$R_4$ can be prepared by reductive alkylation of the amino-substituted [1,3]thiazolo[4,5-c]quinolin-4-amine of Formula XLIII, wherein $R_8$ is hydrogen. The alkylation is conveniently carried out in two parts by (i) adding an aldehyde or ketone to a solution of an amino-substituted [1,3]thiazolo[4,5-c]quinolin-4-amine of Formula XLIII or a salt thereof in a suitable solvent such as DMF in the presence of a base such as N,N-diisopropylethylamine. In part (ii) the reduction is carried out by adding a suitable reducing agent such as the borane-pyridine complex. Both part (i) and part (ii) can be carried out at room temperature. In compounds of Formula XLIII, wherein $R_8$ is hydrogen, it is convenient to carry out the reductive alkylation followed by reaction with an acid chloride, sulfonyl chloride, sulfonic anhydride, isocyanate, or carbamoyl chloride as described above to provide a compound of Formula IIa, wherein $R_{3a}$ is —Z—N($R_8$)-Q-$R_4$, wherein Z, $R_4$, $R_8$, and Q are as defined above.

Dimers of Formula IIa, wherein $R_{3a}$ is —Z—[N($R_8$)-Q]-X[V—N($R_8$)]—X—O—$R_4$, wherein X and $R_8$ are as defined above, Q is selected from the group consisting of —C($R_6$)—, —S(O)₂—, —C($R_6$)—N($R_8$)—, V is selected from the group consisting of —C($R_6$)—, —N($R_8$)—C($R_6$)—, and —S(O)₂—, and $R_4$ is a [1,3]thiazolo[4,5-c]quinoline optionally substituted as defined in $R_4$ above, can be prepared by treating an amino-substituted [1,3]thiazolo[4,5-c]quinolin-4-amine of Formula XLIII or a salt thereof with a diacid chloride, a disulfonyl chloride, or a diisocyanate according to the reaction conditions described above for the reactions with acid chlorides, sulfonyl chlorides, and isocyanates. Numerous diacid chlorides, disulfonyl chlorides, and diisocyanates are commercially available. These include but are not limited to aliphatic compounds such as fumaryl chloride, succinyl chloride, glutaryl chloride, sebacoyl chloride, 2,2'-oxydiacetyl chloride, 1,4-butanedisulfonyl chloride, 1,4-diisocyanatobutane, hexamethylene diisocyanate, and 1,12-diisocyanatododecane; aromatic compounds such as 1,2-benzenedisulfonyl chloride, 1,3- benzenedisulfonyl chloride, 1,4-phenylene diisocyanate, 1,5-naphthalenediisocyanate, phthaloyl chloride, and isophthaloyl chloride; cycloaliphatic compounds such as dicylcohexylmethane-4,4'-diisocyanate, trans-1,4-cyclohexane diisocyanate, and 1,3-bis(isocyanatomethyl)cyclohexane; heteroaryl compounds such as 2,6-pyrdinedicarbonyl chloride; and compounds such as 4,4'-benzoyl chloride, 4,4'-methylene-bis(benzenesulfonyl) chloride, m-xylene diisocyanate, 4,4'-diphenylmethane diisocyanate.

Dimers of Formula IIa, wherein $R_{3a}$ is —Z—[N($R_8$)—C(O)—N($R_8$)]—X—O—$R_4$, wherein X is as defined above, and $R_4$ is a [1,3]thiazolo[4,5-c]quinoline optionally substituted as defined in $R_4$ above, can be prepared by treating an amino-substituted [1,3]thiazolo[4,5-c]quinolin-4-amine of Formula XLIII or a salt thereof with carbonyldiimidazole in a suitable solvent such as DMF at an elevated temperature such as 75° C.

Compounds of the invention can be prepared according to Reaction Scheme V, where R, $R_2$, $R_{10}$, and n are as defined above; $Z_a$ is selected from the group consisting of a bond, alkylene, alkenylene, and alkynylene wherein alkylene, alkenylene, and alkynylene can be optionally interrupted with one or more —O— groups; $R_{3b}$ is

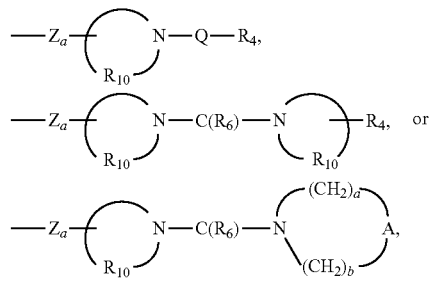

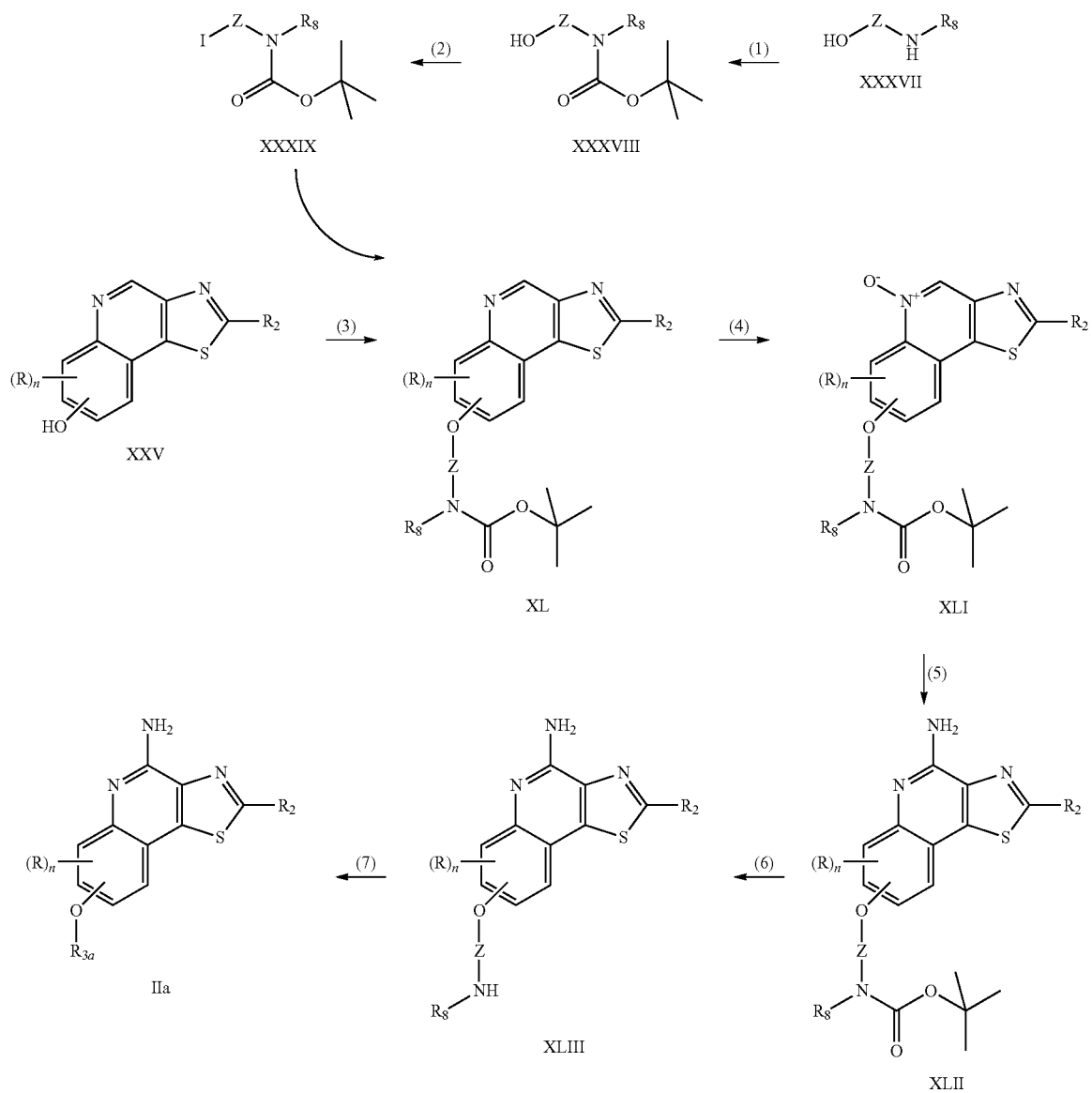

wherein $R_4$, $R_6$, $R_{10}$, A, Q, a, and b are as defined above. Steps (1) through (7) of Reaction Scheme V can be run as described in steps (1) through (7) of Reaction Scheme IV to provide compounds of Formula III), a subgenus of Formulas I and II.

Alternatively, a compound of Formula XLV can react with a [1,3]thiazolo[4,5-c]quinolinol of Formula XXV under the Mitsunobu reaction conditions described in step (10) of carboxylate provides a compound of Formula XLVII wherein $Z_a$ is a bond and $R_{10}$ is pentylene.

The oxidation in step (4) of Reaction Scheme V can be carried out according to the reaction conditions described in step (7) of Reaction Scheme I or by heating a solution of a compound of Formula XLVII in a suitable solvent such as ethyl acetate with peracetic acid at a temperature such as 50° C. and then adding sodium metabisulfate.

Reaction Scheme V

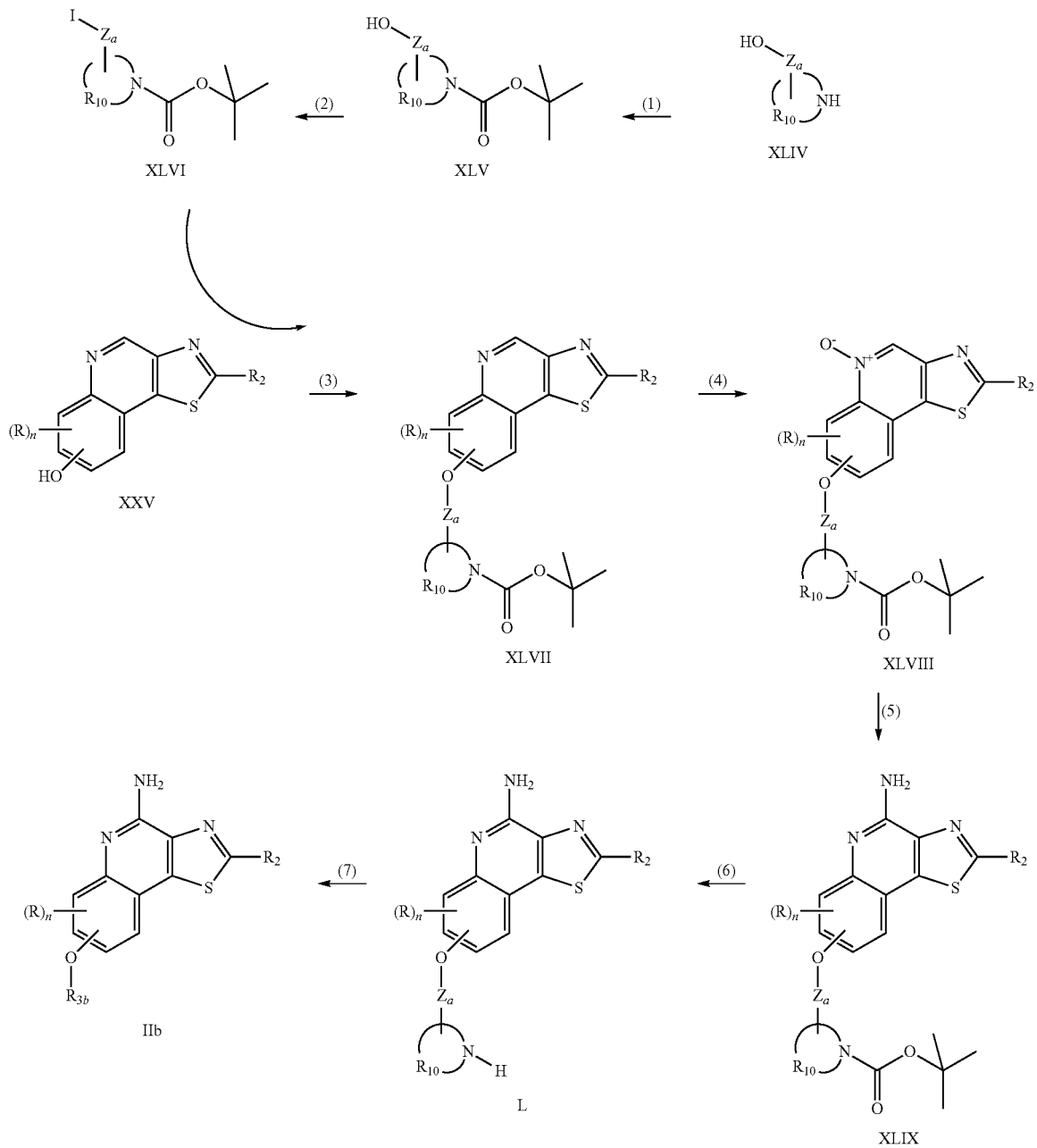

Reaction Scheme I. For example, combining a [1,3]thiazolo[4,5-c]quinolinol of Formula XXV, triphenylphosphine, and tert-butyl 4-hydroxy-1-piperdinecarboxylate in THF at 5° C. or room temperature and slowly adding diisopropyl azodi- Compounds of the invention can also be prepared according to Reaction Scheme VI, wherein R, $R_2$, and n are as defined above; Z is selected from the group consisting of alkylene, alkenylene, and alkynylene wherein alkylene, alkenylene, and alkynylene can be optionally interrupted with one or more —O— groups; and $R_{3c}$ is —Z-Het, —Z-Het'-$R_4$, or —Z-Het'-Y—$R_4$, wherein Het or Het' is attached to Z at a nitrogen atom.

In step (1) of Reaction Scheme VI, a [1,3]thiazolo[4,5-c]quinolinol of Formula XXIV is treated with a dihalide of Formula I—Z—Cl or Br—Z—Cl using the Williamson conditions described in step (10) of Reaction Scheme I to provide a chloro-substituted compound of Formula X.

In step (2) of Reaction Scheme VI, a chloro-substituted compound of Formula X is treated with a cyclic secondary amine to provide a compound of Formula IIc, a subgenus of Formulas I and II. Many cyclic secondary amines are commercially available, such as unsubstituted or substituted pyrrolidines, piperidines, morpholines, and piperazines; others can be prepared using conventional methods. The reaction can be conveniently carried out by adding a cyclic secondary amine to a compound of Formula X in a suitable solvent such as DMF. The reaction can be conveniently carried out in the presence of a base such as potassium carbonate at an elevated temperature such as 65° C.

Compounds of Formula IIc are also prepared from [1,3]thiazolo[4,5-c]quinolinols of Formula XXV, shown in Reaction Scheme II. A [1,3]thiazolo[4,5-c]quinolinol of Formula XXV is first treated with a dihalide of Formula I—Z—Cl or Br—Z—Cl according to step (1) of Reaction Scheme V. The product is then oxidized and aminated according to the methods described in steps (7) and (8) of Reaction Scheme I to provide a compound of Formula X, which is then treated with a cyclic secondary amine as described in step (2) of Reaction Scheme VI to provide a compound of Formula IIc.

A compound of Formula X is also a useful starting material to provide a number of other compounds of the invention. For example, a compound of Formula X can be treated with a non-cyclic secondary amine or a mercaptan under the conditions described in step (2) above to provide a compound in which $R_{3c}$ is —Z—Y—$R_4$, wherein $R_4$ is as defined above and Y is —N($R_8$)-Q- or —S—, wherein Q is a bond and $R_8$ is as defined above. In another example, a compound of Formula X can be treated under the same conditions with a substituted phenol to provide a compound wherein $R_{3c}$ is —Z—Y—X—Y—$R_4$, in which the Y bonded to Z is —O—, X is phenylene, and $R_4$ and the Y bonded to $R_4$ are as defined above or a compound wherein $R_{3c}$ is —Z—Y—$R_4$, in which Y is —O—, and $R_4$ is phenyl that is optionally substituted. In yet another example, a compound of Formula X can be treated with N-hydroxyphthalimide in the presence of a base, such as triethylamine, in a suitable solvent such as DMF at ambient temperature. The phthalimide group can then be removed from the resulting N-phthalimide-protected hydroxylamine by treatment with hydrazine at ambient temperature in a suitable solvent such as ethanol. The resulting hydroxylamine can then be treated with one of numerous commercially available aldehydes or ketones in a suitable solvent such as methanol to provide a compound of Formula IIc wherein $R_{3c}$ is —Z—Y—$R_4$ or —Z—$R_5$, where Y is —O—N═C($R_4$)—, $R_5$ is

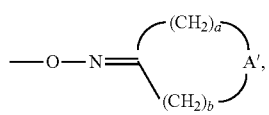

and $R_4$, a, b, and A' are as defined above. Alternatively, the hydroxylamine prepared after the hydrazine deprotection may be treated with one of numerous acid chlorides, sulfonyl chloride, isocyanates, carbamoyl chloride, or sulfamoyl chlorides using one of the methods described in step (7) of Reaction Scheme IV to provide a compound Formula IIc wherein $R_{3c}$ is —Z—Y—$R_4$ where Y is —O—NH-Q-, and Q and $R_4$ are as defined above.

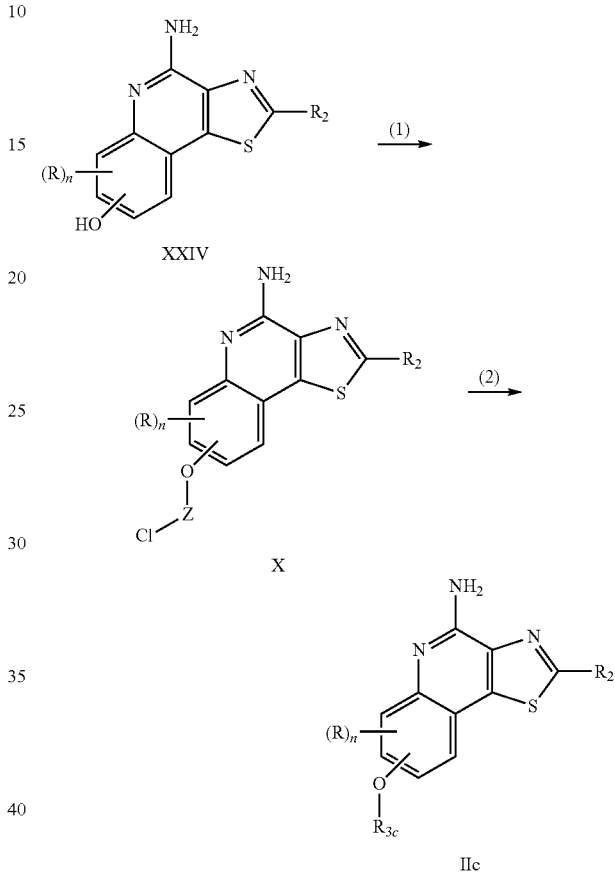

Reaction Scheme VI

Compounds of the invention can also be prepared using variations of the synthetic routes shown in Reaction Schemes I through VI that would be apparent to one of skill in the art. For example, the synthetic route shown in Reaction Scheme IV for the preparation of quinolines having a $R_{3a}$ substituent can be used to prepare [1,5]naphthyridines having a $R_{3a}$ substituent by using a [1,3]thiazolo[4,5-c][1,5]naphthyridinol in lieu of the [1,3]thiazolo[4,5-c]quinolinol. Similarly, the synthetic routes shown in Reaction Schemes V and VII can be carried out using a [1,3]thiazolo[4,5-c][1,5]naphthyridinol instead of a [1,3]thiazolo[4,5-c]quinolinol as a starting material. Compounds of the invention can also be prepared using the synthetic routes described in the EXAMPLES below.

Prodrugs can be prepared in a variety of ways. For example, a compound wherein $R_3$ or $R_2$ is —X—OH (e.g. hydroxyalkyl) can be converted into a prodrug wherein $R_3$ or $R_2$ is, for example, —X—O—C($R_6$)—$R_4$, —X—O—C($R_6$)—O—$R_4$, or —X—O—C($R_6$)—N($R_8$)—$R_4$, wherein X, $R_4$, $R_6$, and $R_8$ are as defined above, using methods known to one skilled in the art. In addition, a compound wherein R is hydroxy may also be converted to an ester, an ether, a carbonate, or a carbamate. For any of these compounds containing an alcohol functional group, a prodrug can be formed by the replacement of the hydrogen atom of the alcohol group with a group such as $C_{1-6}$ alkanoyloxymethyl, 1-($C_{1-6}$alkanoyloxy)ethyl, 1-methyl-1-($C_{1-6}$alkanoyloxy)ethyl, $C_{1-6}$alkoxycarbonyloxymethyl, N—($C_{1-6}$ alkoxycarbonyl)aminomethyl, succinoyl, $C_{1-6}$ alkanoyl, α-amino$C_{1-4}$alkanoyl, arylacyl, —P(O)(OH)$_2$, —P(O)(O—$C_{1-6}$alkyl)$_2$, $C_{1-6}$alkoxycarbonyl, $C_{1-6}$ alkylcarbamoyl, and α-aminoacyl or α-aminoacyl-α-aminoacyl, where each α-aminoacyl group is independently selected from racemic, D-, and L-amino acids. For compounds containing an alcohol functional group, particularly useful prodrugs are esters made from carboxylic acids containing one to six carbon atoms, unsubstituted or substituted benzoic acid esters, or esters made from amino acids. The reaction conditions described above in step (7) of Reaction Scheme IV can be used.

Prodrugs can also be made from a compound containing an amino group by conversion of the amino group to a functional group such as an amide, carbamate, urea, amidine, or another hydrolyzable group using conventional methods. A prodrug of this type can be made by the replacement of a hydrogen atom in an amino group, particularly the amino group at the 4-position, with a group such as —C(O)—R', α-aminoacyl, α-aminoacyl-α-aminoacyl, —C(O)—O—R', —C(O)—N(R''')—R', —C(=NY')—R', —CH(OH)—C(O)—OY$_1$, —CH(O$C_{1-4}$ alkyl)Y$_0$, —CH$_2$Y$_2$, or —CH(CH$_3$)Y$_2$; wherein R' and R''' are each independently $C_{1-10}$ alkyl, $C_{3-7}$ cycloalkyl, phenyl, or benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R''' can also be hydrogen; each α-aminoacyl group is independently selected from racemic, D-, and L-amino acids; Y$_1$ is hydrogen, $C_{1-6}$ alkyl, or benzyl; Y$_0$ is $C_{1-6}$ alkyl, carboxy$C_{1-6}$alkylenyl, amino$C_{1-4}$alkylenyl, mono-N—$C_{1-6}$ alkylamino$C_{1-4}$alkylenyl, or di-N,N—$C_{1-6}$ alkylamino$C_{1-4}$ alkylenyl; and Y$_2$ is mono-N—$C_{1-6}$ alkylamino, di-N,N—$C_{1-6}$alkylamino, morpholin-4-yl, piperidin-1-yl, pyrrolidin-1-yl, or 4-$C_{1-4}$ alkylpiperazin-1-yl. For compounds containing an amine functional group, particularly useful prodrugs are amides derived from carboxylic acids containing one to ten carbon atoms, amides dervied from racemic, D-, or L-amino acids, and carbamates containing one to ten carbon atoms. The reaction can be carried out, for example, by combining a compound of Formula I, II, III, IV, V, or VI with a chloroformate or acid chloride, such as ethyl chloroformate or acetyl chloride, in the presence of a base such as triethylamine in a suitable solvent such as dichloromethane at room temperature.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as *chlamydia*, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Omen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245, 776, and U.S. Publication Nos. 2003/0139364, 2003/ 185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Example 1

7-(2-Morpholin-4-ylethoxy)-2-propyl[1,3]thiazolo[4,5-c]quinolin-4-amine

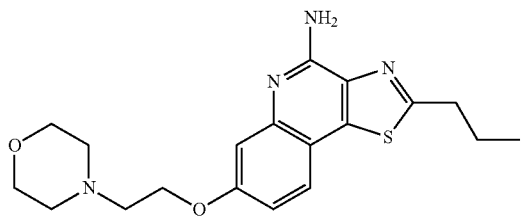 [SMILES: CCCc1nc2c(N)nc3cc(OCCN4CCOCC4)ccc3c2s1]

Part A

A mixture of triethyl orthoformate (92 milliliters (mL), 0.55 moles (mol)) and 2,2-dimethyl-[1,3]-dioxane-4,6-dione (75.3 grams (g), 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (approximately 400 mL) until the filtrate was colorless. 5-{[(3-Benzyloxy)phenylimino]methyl}-2,2-dimethyl-[1, 3]-dioxane-4,6-dione (170.65 g) was isolated as a tan, powdery solid. $^1$H NMR (300MHz, DMSO-d$_6$) δ 11.21 (d, J=14.2 Hz, 1H), 8.61 (d, J=14.2 Hz, 1H), 7.49-7.30 (m, 7H), 7.12 (dd, J=8.1, 1.96 Hz, 1H), 6.91 (dd, J=8.4, 2.1 Hz, 1H), 5.16 (s, 2H), 1.68 (s, 6H).

Part B

A mixture of 5-{[(3-benzyloxy)phenylimino]methyl}-2, 2-dimethyl-[1,3]-dioxane-4,6-dione (170.65 g, 0.483 mol) and DOWTHERM A (800 mL) heat transfer fluid was heated to 100° C. and then slowly added to a flask containing DOWTHERM A (1.3 liters (L), heated at 210° C.) heat transfer fluid over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed sequentially with diethyl ether (1.7 L) and acetone (0.5 L), and dried in an oven to provide 76.5 g of 7-benzyloxyquinolin-4-ol as a tan powder. $^1$H NMR (300MHz, DMSO-d$_6$) δ 11.53 (s, 1H), 7.99 (dd, J=2.4, 7.4 Hz, 1H), 7.79 (d, J=7.4 Hz, 1H), 7.50-7.32 (m, 5H), 7.00 (s, 1H), 6.98 (dd, J=2.5, 7.4 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 molar (M)) was slowly added over a period of 30 minutes while maintaining the reaction temperature between 121° C. and 125° C. After the addition, the reaction was stirred at 125° C. for one hour then allowed to cool to room temperature. The resulting solid was isolated by filtration, washed with water, and dried in an oven for 1.5 days to provide 69.13 g of 7-benzyloxy-3-nitroquinolin-4-ol as a grayish powder. $^1$H NMR (300MHz, DMSO-d$_6$) δ 12.77 (s, 1H), 9.12 (s, 1H), 8.17 (dd, J=3.3, 6.3 Hz, 1H), 7.51-7.33 (m, 5H), 7.21-7.17 (m, 2H), 5.25 (s, 2H). Material from a separate run was used in the next step.

Part D

A mixture of 7-benzyloxy-3-nitroquinolin-4-ol (10.67 g, 36.0 millimoles (mmol)) and 5% platinum on carbon (1.05 g) in N,N-dimethylformamide (DMF) (110 mL) was hydrogenated on a Parr apparatus. The mixture was filtered through CELITE filter agent. The CELITE filter agent was rinsed with DMF (20 mL). The filtrate was cooled in an ice bath and acidified with hydrogen chloride gas, resulting in the formation of a reddish-brown solid. The solid was isolated by filtration, washed with acetone, and dried in a vacuum oven at 60° C. to provide 8.17 g of 3-amino-7-benzyloxyquinolin-4-ol hydrochloride as a tan solid.

Part E

To a solution of the crude 3-amino-7-benzyloxyquinolin-4-ol hydrochloride (8.03 g, 26.5 mmol) prepared in Part D and triethylamine (7.40 mL, 53 mmol) in dichloromethane at 0° C. was added butyryl chloride (2.75 mL, 26.5 mmol) dropwise. The solution was stirred at 0° C. for ten minutes, and then the cooling bath was removed. A solid formed that was isolated by filtration and washed with a small amount of dichloromethane. The solid was triturated with water (75 mL) and was isolated by filtration. The solid was rinsed sequentially with water and diethyl ether and dried at 60° C. in a vacuum oven to provide 8.03 g of N-(7-benzyloxy-4-hydroxyquinolin-3-yl)butyramide, containing a small amount of triethylamine hydrochloride as determined by proton nuclear magnetic resonance spectroscopy ($^1$H NMR) analysis.

Part F

Under a nitrogen atmosphere, a mixture of the N-(7-benzyloxy-4-hydroxyquinolin-3-yl)butyramide prepared in Part E (2.97 g, 8.83 mmol), phosphorus pentasulfide (1.96 g, 4.41 mmol), and pyridine was heated to reflux. The resulting solution was cooled and the excess phosphorus pentasulfide was quenched slowly with 10% aqueous sodium carbonate (10 mL). The reaction mixture was partitioned between water (40 mL) and dichloromethane (100 mL). The organic layer was washed with 0.1 M aqueous hydrochloric acid (50 mL), dried over magnesium sulfate, filtered and concentrated under reduced pressure to yield a brownish-yellow solid. The solid was recrystallized from heptane (40 mL, hot filtration). The crystals were isolated by filtration and washed with cold heptane to provide 1.74 g of 7-benzyloxy-2-propyl[1,3]thiazolo[4,5-c]quinoline as a light yellow solid.

Part G

To a solution of 7-benzyloxy-2-propyl[1,3]thiazolo[4,5-c]quinoline (4.89 g, 14.6 mmol) in dichloromethane (75 mL) at room temperature was added 3-chloroperoxybenzoic acid (mCPBA) (5.82 g of 65% purity, 21.93 mmol) in portions. After one hour of stirring, the mixture was washed with 10% aqueous sodium carbonate (2×50 mL). The combined washings were extracted with dichloromethane (50 mL), and the combined organic fractions were washed with water (75 mL), dried over magnesium sulfate, filtered, concentrated under reduced pressure, and dried under high vacuum to yield 4.93 g of 7-benzyloxy-5-oxido-2-propyl[1,3]thiazolo[4,5-c]quinoline as a light yellow solid.

Part H

To a light orange solution of 7-benzyloxy-5-oxido-2-propyl[1,3]thiazolo[4,5-c]quinoline (4.93 g, 14.1 mmol) in dichloromethane (100 mL) at 0° C. was added trichloroacetyl isocyanate (2.00 mL, 16.9 mmol). The solution was allowed to warm to room temperature and was stirred for 20 hours. The solution was concentrated under reduced pressure, and the residue, N-(7-benzyloxy-2-propyl[1,3]thiazolo[4,5-c]quinolin-4-yl)-2,2,2-trichloroacetamide, was used without further manipulation in the next step.

Part I

To a stirred mixture of N-(7-benzyloxy-2-propyl[1,3]thiazolo[4,5-c]quinolin-4-yl)-2,2,2-trichloroacetamide (6.96 g, 14.9 mmol) in methanol (100 mL) at room temperature was added sodium methoxide (11.3 mL of a 25 weight % solution in methanol, 52.1 mmol). After a few minutes a solution formed from which a solid precipitated. The reaction mixture was concentrated under reduced pressure and further dried under vacuum. The resulting solid was suspended in a minimal amount of methanol (50 mL) and was isolated by filtration. The solid was washed with methanol to provide 3.93 g of 7-benzyloxy-2-propyl[1,3]thiazolo[4,5-c]quinolin-4-amine as a light yellow solid, mp 175-178° C. $^1$H NMR (300MHz, d$_6$-DMSO) δ 7.67 (d, J=8.7 Hz, 1H), 7.49-7.29 (m, 5H), 7.10 (d, J=2.5 Hz, 1H), 6.96 (dd, J=8.7, 2.5 Hz, 1H), 6.84 (s, 2H), 5.20 (s, 2H), 3.09 (t, J=7.8 Hz, 2H), 1.84 (sextet, J=7.2 Hz, 2H), 0.99 (t, J=7.5 Hz, 3H); $^{13}$C NMR (75 MHz, d$_6$-DMSO) δ 169.1, 158.9, 152.4, 146.5, 139.4, 137.0, 136.0, 128.4, 127.8, 127.6, 125.7, 113.3, 113.2, 107.8, 69.3, 35.1, 22.8, 13.5; MS (APCI) m/z 350.0 (M+H$^+$).

Part J

Under a nitrogen atmosphere, a solution of hydrogen bromide in acetic acid (50 mL of 30% weight/weight (w/w)) was added to 7-benzyloxy-2-propyl[1,3]thiazolo[4,5-c]quinolin-4-amine (3.55 g, 10.2 mmol), and the reaction was heated at 65° C. for 30 minutes and then cooled to approximately 0° C. Aqueous sodium hydroxide (50% w/w) was added slowly to adjust the reaction mixture to pH 7. A light yellow solid formed, which was isolated by filtration and air-dried to provide 4-amino-2-propyl[1,3]thiazolo[4,5-c]quinolin-7-ol acetic acid salt.

Part K

Under a nitrogen atmosphere, cesium carbonate (6.29 g, 19.3 mmol) was added to a suspension of the material from Part J (3.86 mmol) in DMF (20 mL), and the reaction mixture was heated at 75° C. for 30 minutes. 4-(2-Chloroethyl)morpholine hydrochloride (0.90 g, 4.8 mmol) was then added, and the mixture was stirred at 75° C. overnight. The solvent was then removed under reduced pressure at 65° C. The resulting solid was partitioned between dichloromethane (100 mL) and water (100 mL). The organic layer was washed sequentially with water (50 mL) and brine (50 mL), dried over magnesium sulfate, filtered, and concentrated under reduced pressure. The resulting dark brown solid was purified by column chromatography using a HORIZON HPFC system (an automated, modular high-performance flash purification product available from Biotage, Inc, Charlottesville, Va., USA) (silica cartridge, eluting with 0 to 30% 80:18:2 chloroform/methanol/concentrated ammonium hydroxide (CMA) in chloroform) to provide 0.48 g of a light yellow solid after drying under high vacuum. The solid was recrystallized from tert-butyl methyl ether (30 mL, hot filtration), and the crystals were washed with cold tert-butyl methyl ether and dried in a vacuum oven at 60° C. to provide 0.32 g of 7-(2-morpholin-4-ylethoxy)-2-propyl[1,3]thiazolo[4,5-c]quinolin-4-amine as light yellow needles, mp 122-125° C. $^1$H NMR (500 MHz, d$_6$-DMSO) δ 7.65 (d, J=8.5, 1H), 7.03 (d, J=2.5, 1H ), 6.90 (dd, J=8.5, 2.5, 1H), 6.79 (s, 2H), 4.17 (t, J=5.6, 2H), 3.58 (t, J=4.8, 4H), 3.11 (t, J=7.6, 2H ), 2.72 (t, J=5.6, 2H), 2.48 (m, 4H), 1.84 (sextet, J=7.5, 2H), 1.00 (t, J=7.5, 3H); $^{13}$C NMR (125 Hz, d$_6$-DMSO) δ 169.0, 159.0, 152.3, 146.5, 139.3, 136.0, 125.7, 113.1, 113.0, 107.3, 66.1, 65.4, 57.0, 53.6, 35.1, 22.7, 13.4;

Anal. calcd for $C_{19}H_{24}N_4O_2S$: C, 61.27; H, 6.49; N, 15.04. Found: C, 61.24; H, 6.54; N, 14.94.

Example 2

2-Propyl-7-(2-pyrrolidin-1-ylethoxy) [1,3]thiazolo[4,5-c]quinolin-4-amine

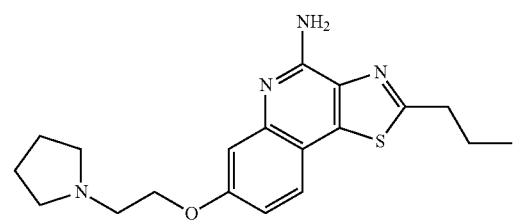 [SMILES: CCCc1nc2c(N)nc3cc(OCCN4CCCC4)ccc3c2s1]

The method described in Part K of Example 1 was used to treat the material from Part J of Example 1 (5.40 mmol) in DMF (25 mL) with cesium carbonate (11.00 g, 33.75 mmol) and 1-(2-chloroethyl)pyrrolidine hydrochloride (1.15 g, 6.75 mmol) with the modification that the reaction was carried out at 70° C. instead of 75° C. The purification methods described in Part K of Example 1 were used to provide 0.33 g of 2-propyl-7-(2-pyrrolidin-1-ylethoxy)[1,3]thiazolo[4,5-c]quinolin-4-amine as light yellow needles, mp 124-127° C. $^1$H NMR (500 MHz, CDCl$_3$) δ 7.59 (d, J=8.8, 1H), 7.17 (d, J=2.2, 1H), 6.98 (dd, J=8.9, 2.5, 1H), 5.51 (s, 2H), 4.22 (t, J=5.7, 2H), 3.09 (t, J=7.6, 2H) 2.95 (t, J=6.0, 2H), 2.63 (m, 4H), 1.93 (sextet, J=7.5, 2H), 1.80 (m, 4H), 1.07 (t, J=7.2, 3H); $^{13}$C NMR (125 Hz, CDCl$_3$) δ 169.7, 159.8, 151.8, 146.2, 140.7, 136.4, 125.6, 115.0, 114.3, 107.5, 67.2, 55.1, 54.7, 36.0, 23.5, 23.2, 13.7;

Anal. calcd for C$_{19}$H$_{24}$N$_4$OS: C, 64.02; H, 6.79; N, 15.72. Found: C, 63.85; H, 6.65; N, 15.64.

Example 3

7-(2-Piperidin-1-ylethoxy)-2-propyl[1,3]thiazolo[4,5-c]quinolin-4-amine

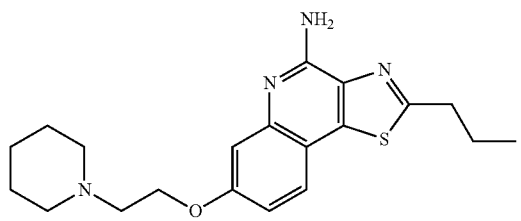 [SMILES: CCCc1nc2c(N)nc3cc(OCCN4CCCCC4)ccc3c2s1]

The method described in Part K of Example 1 were used to treat the material from Part J of Example 1 (5.67 mmol) in DMF (25 mL) with cesium carbonate (9.24 g, 28.4 mmol) and 1-(2-chloroethyl)piperidine hydrochloride (1.30 g, 7.09 mmol) with the modification that the reaction was carried out at 70° C. instead of 75° C. The purification methods described in Part K of Example 1 were used, with the modification that chromatographic purification was carried out eluting with 0 to 35% CMA in chloroform, to provide 0.41 g of 7-(piperidin-1-ylethoxy)-2-propyl[1,3]thiazolo[4,5-c]quinolin-4-amine as light yellow needles, mp 141-143° C. $^1$H NMR (500 MHz, d$_6$-DMSO) δ 7.65 (d, J=8.9, 1H), 7.03 (d, J=2.5, 1H), 6.89 (dd, J=8.9, 2.2, 1H), 6.79 (s, 2H), 4.14 (t, J=6.0, 2H), 3.10 (t, J=7.5, 2H), 2.67 (t, J=6.0, 2H), 2.43 (m, 4H), 1.84 (sextet, J=7.5, 2H), 1.49 (quin, J=4.6, 4H), 1.36 (m 2H), 1.00 (t, J=7.6, 3H); $^{13}$C NMR (125 Hz, d$_6$-DMSO) δ 169.0, 159.1, 152.4, 146.5, 139.4, 136.0, 125.7, 113.1, 113.0, 107.3, 65.7, 57.3, 54.4, 35.1, 25.6, 23.9, 22.7, 13.4;

Anal. calcd for C$_{20}$H$_{26}$N$_4$OS: C, 64.83; H, 7.07; N, 15.12. Found: C, 64.52; H, 7.37; N, 14.80.

Example 4 tert-Butyl 3-[(4-amino-2-propyl[1,3]thiazolo[4,5-c]quinolin-7-yl)oxy]propylcarbamate

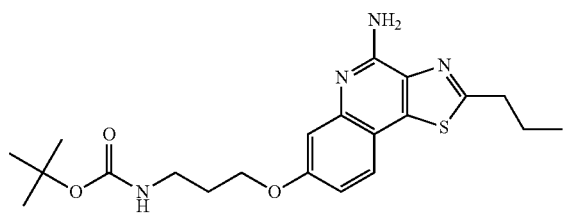 [SMILES: CCCc1nc2c(N)nc3cc(OCCCNC(=O)OC(C)(C)C)ccc3c2s1]

Part A

A solution of 3-amino-1-propanol (14.88 g, 0.1981 mol) in dichloromethane (130 mL) was cooled to approximately 0° C., and a solution of di-tert-butyl dicarbonate (46.70 g, 0.2140 mol) in dichloromethane (100 mL) was added dropwise over a period of 45 minutes. Upon the completion of the addition, the resulting solution was washed sequentially with aqueous sodium carbonate (2×100 mL of 2 M), acetic acid (2×50 mL of 5% w/w), and brine (75 mL); dried over magnesium sulfate; filtered; and concentrated under reduced pressure to provide 39.02 g of tert-butyl 3-hydroxypropylcarbamate as a colorless oil containing some tert-butanol.

Part B

A mixture of tert-butyl 3-hydroxypropylcarbamate (19.36 g, 110.5 mmol), triphenylphosphine (34.76 g, 132.6 mmol), imidazole (10.53 g, 154.7 mmol), diethyl ether (500 mL), and acetonitrile (150 mL) was cooled to approximately 0° C., and iodine (36.45 g, 143.6 mmol) was added in one portion. The reaction mixture was allowed to warm to room temperature slowly and stirred overnight. A precipitate formed, which was removed by filtration and washed with a small amount of diethyl ether. The filtrate was washed sequentially with water (2×500 mL), saturated aqueous sodium thiosulfate (2×250 mL), water (250 mL), and brine (250 mL); dried over magnesium sulfate; filtered; and concentrated under reduced pressure to provide a mixture of a yellow oil and a white solid. The mixture was diluted with heptane (50 mL) and filtered to remove the solid, which was washed with heptane (50 mL). The filtrate was concentrated under reduced pressure to provide an oil that was diluted with heptane (50 mL) and filtered to remove a solid, which was washed with heptane (50 mL). The filtrate was concentrated under reduced pressure to provide 22.60 g of tert-butyl 3-iodopropylcarbamate as a yellow oil containing about 9 mol % triphenylphosphine oxide as determined by $^1$H NMR.

Part C

To 7-benzyloxy-2-propyl[1,3]thiazolo[4,5-c]quinoline (prepared as described in Part F of Example 1, 4.52 g, 13.5 mmol) was added hydrogen bromide (40 mL of a 45 wt. % solution in acetic acid). The resulting solution was heated at 65° C. for 1.5 hours and then cooled in an ice bath. Aqueous sodium hydroxide (50% w/w solution) was added slowly to adjust the solution to pH 7, and a light yellow solid formed. The solid was isolated by filtration, dried, and then suspended in boiling ethanol (25 mL) for 5 minutes. The mixture was allowed to cool to room temperature, and a tan solid was isolated by filtration. The solid was washed with cold ethanol and dried in a vacuum oven to yield 2.69 g of 2-propyl[1,3]thiazolo[4,5-c]quinolin-7-ol. Material from a separate run was used in the next step.

Part D

Under a nitrogen atmosphere, cesium carbonate (10.13 g, 31.07 mmol) was added to a suspension of 2-propyl[1,3]thiazolo[4,5-c]quinolin-7-ol (5.06 g, 20.7 mmol) in DMF (110 mL), and the reaction mixture was heated at 65° C. A solution of tert-butyl 3-iodopropylcarbamate (7.08 g, 24.8 mmol) in DMF (20 mL) was added dropwise with stirring. The reaction mixture was stirred at 65° C. overnight. The solvent was then removed under reduced pressure at 65° C. The resulting solid was partitioned between dichloromethane (250 mL) and water (250 mL). The organic layer was washed sequentially with saturated aqueous sodium thiosulfate (100 mL), water (100 mL), and brine (100 mL); dried over magnesium sulfate; filtered; and concentrated under reduced pressure. The resulting solid was purified by column chromatography on silica gel (eluting with 0 to 4% methanol in chloroform) to provide 5.36 g of tert-butyl 3-[(2-propyl[1,3]thiazolo[4,5-c]quinolin-7-yl)oxy]propylcarbamate as a light yellow solid.

Part E

The method described in Part G of Example 1 was used to treat tert-butyl 3-[(2-propyl[1,3]thiazolo[4,5-c]quinolin-7-yl)oxy]propylcarbamate (1.20 g, 2.99 mmol) with mCPBA (1.19 g of 65% pure material, 4.49 mmol) in dichloromethane (20 mL) with the modification that the reaction was stirred overnight. tert-Butyl 3-[(5-oxido-2-propyl[1,3]thiazolo[4,5-c]quinolin-7-yl)oxy]propylcarbamate (1.08 g) was obtained as a light yellow solid.

Part F

A solution of tert-butyl 3-[(5-oxido-2-propyl[1,3]thiazolo[4,5-c]quinolin-7-yl)oxy]propylcarbamate (1.08 g, 2.59 mmol) in 1,2-dichloroethane (25 mL) was heated in a sealed tube to 65° C., and then ammonium hydroxide (5 mL of 30% solution) and p-toluenesulfonyl chloride (0.49 g, 2.8 mmol) were added. The reaction was heated at 65° C. for 24 hours and then diluted with dichloromethane (50 mL). The resulting mixture was washed with aqueous sodium carbonate (2×50 mL of 2 M), and the combined washings were extracted with dichloromethane (2×50 mL). The combined organic layers were washed sequentially with water (50 mL) and brine (50 mL), dried over magnesium sulfate, filtered, and concentrated under reduced pressure. The resulting light brown solid was purified by column chromatography using a HORIZON HPFC system (silica cartridge, eluting with 0 to 18% CMA in chloroform) to provide 0.72 g of a light yellow solid after drying under high vacuum. The solid was recrystallized from tert-butyl methyl ether (40 mL, hot filtration), and the crystals were washed with cold tert-butyl methyl ether and dried in a vacuum oven at 40° C. overnight to provide tert-butyl 3-[(4-amino-2-propyl[1,3]thiazolo[4,5-c]quinolin-7-yl)oxy]propylcarbamate as off-white needles, mp 146-149° C. $^1$H NMR (300 MHz, $d_6$-DMSO) δ 7.66 (d, J=8.8, 1H), 7.01 (d, J=2.5, 1H), 6.90 (t, J=2.5, 1H), 6.88 (dd, J=9.0, 2.5, 1H), 6.77 (s, 2H), 4.05 (t, J=6.3, 2H), 3.11 (t, J=7.2, 2H), 3.08 (t, J=3.4, 2H), 1.90-1.78 (m, 4H), 1.36 (s, 9H), 1.00 (t, J=7.5, 3H); $^{13}$C NMR (75 MHz, $d_6$-DMSO) δ 169.0, 159.2, 155.6, 152.3, 146.5, 139.4, 136.0, 126.6, 125.6, 113.1, 113.0, 107.2, 79.1, 77.5, 65.3, 36.9, 35.1, 29.2, 28.2, 22.8, 13.4;

Anal. calcd for $C_{21}H_{28}N_4O_3S$: C, 60.55; H, 6.78; N, 13.45. Found: C, 60.64; H, 6.82; N, 13.57.

Example 5

N-{3-[(4-Amino-2-propyl[1,3]thiazolo[4,5-c]quinolin-7-yl)oxy]propyl}methanesulfonamide

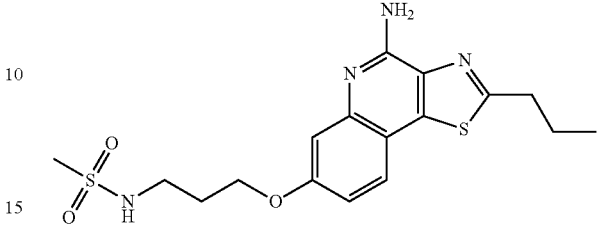

Part A

A solution of hydrogen chloride in ethanol (2 mL of 4.25 M) was added to a suspension of tert-butyl 3-[(4-amino-2-propyl[1,3]thiazolo[4,5-c]quinolin-7-yl)oxy]propylcarbamate (0.69 g, 1.66 mmol) in ethanol (15 mL), and the reaction was heated at 80° C. for 30 minutes, allowed to cool to room temperature, and stirred overnight. The solvent was removed under reduced pressure, and dichloromethane (100 mL) was added. The resulting solution was washed with water (100 mL). The aqueous fraction was made basic with the addition of ammonium hydroxide, and the resulting solution was extracted with dichloromethane (2×50 mL). The organic fractions were combined, washed with brine (75 mL), dried over magnesium sulfate, filtered, and concentrated under reduced pressure to provide 0.58 g of 7-(3-aminopropoxy)-2-propyl[1,3]thiazolo[4,5-c]quinolin-4-amine containing some impurities.

Part B

Under a nitrogen atmosphere, a suspension of the material from Part A and triethylamine (0.51 mL, 3.7 mmol) in dichloromethane (25 mL) was cooled to approximately 0° C. Methanesulfonyl chloride (0.14 mL, 1.8 mmol) was added dropwise, and the reaction was allowed to slowly warm to room temperature and stirred overnight. An analysis by high-performance liquid chromatography (HPLC) indicated that starting material remained. The solvent was removed under reduced pressure, and the residue was suspended in chloroform (80 mL) with triethylamine (5 mL). Methanesulfonyl chloride (0.14 mL, 1.8 mmol) was added, and the reaction was stirred at room temperature for 5.5 hours. The reaction was monitored by HPLC, and additional methanesulfonyl chloride (0.84 mL, 11 mmol) was added over the course of four days. The reaction mixture was partitioned between chloroform (50 mL) and water (100 mL). The organic fraction was washed with brine (2×50 mL), dried over magnesium sulfate, filtered, and concentrated under reduced pressure. The resulting light yellow solid was purified by column chromatography using a HORIZON HPFC system (silica cartridge, eluting with 0 to 25% CMA in chloroform), and the purified product was dried in a vacuum oven at 60° C. overnight to provide 0.17 g of N-{3-[(4-amino-2-propyl[1,3]thiazolo[4,5-c]quinolin-7-yl)oxy]propyl}methanesulfonamide as off-white needles, nip 168-171° C. $^1$H NMR (300 MHz, $d_6$-DMSO) δ 7.66 (d, J=8.7, 1H), 7.08 (t, J=5.9, 1H), 7.04 (d, J=2.5, 1H), 6.90 (dd, J=8.8, 2.5, 1H), 6.79 (s, 2H), 4.12 (t, J=6.2, 2H), 3.17-3.08 (m, 4H), 2.90 (s, 3H), 1.93 (sextet, J=6.6, 2H), 1.84 (sextet, J=7.2, 2H), 1.00 (t, J=7.5, 3H); $^{13}$C NMR (75 MHz, $d_6$-DMSO) δ 169.0, 159.1, 152.3, 146.5, 139.3, 135.9, 125.6, 113.1, 107.3, 64.9, 39.4, 39.2, 35.0, 29.2, 22.7, 13.4;

Anal. calcd for $C_{17}H_{22}N_4O_3S_2$: C, 51.76; H, 5.62; N, 14.20. Found: C, 51.53; H, 5.37; N, 14.10.

Example 6

N-{3-[(4-Amino-2-propyl[1,3]thiazolo[4,5-c]quinolin-7-yl)oxy]propyl}-5-(dimethylamino)naphthalene-1-sulfonamide

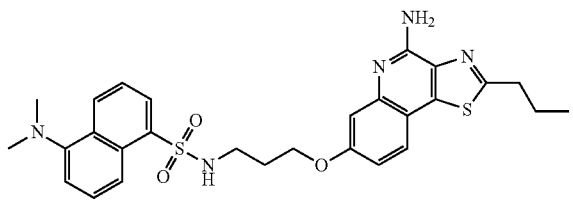 [SMILES: CCCc1nc2c(N)nc3cc(OCCCNS(=O)(=O)c4cccc5c(N(C)C)cccc45)ccc3c2s1]

Pyridine (5 mL) and 4-dimethylaminopyridine (100 mg) were added to 7-(3-aminopropoxy)-2-propyl[1,3]thiazolo[4,5-c]quinolin-4-amine (0.93 g, 2.9 mmol, prepared according to the method described in Part A of Example 5) in dichloromethane (40 mL). 5-Dimethylamino-1-naphthalenesulfonyl chloride (0.95 g, 3.5 mmol, dansyl chloride) were sequentially added to the mixture, and the resulting yellow solution was stirred overnight under a nitrogen atmosphere at room temperature. An analysis by HPLC indicated the presence of starting material, and additional dansyl chloride (240 mg) was added. The reaction was stirred for two hours and then mixed with water (100 mL). The aqueous fraction was extracted with chloroform (2×100 mL), and the combined organic fractions were washed with brine (100 mL), dried over magnesium sulfate, filtered, and concentrated under reduced pressure. The resulting light yellow solid was purified by column chromatography using a HORIZON HPFC system (silica cartridge, eluting with 0 to 20% CMA in chloroform), and the purified product was dried under high vacuum to provide 1.17 g of N-{3-[(4-amino-2-propyl[1,3]thiazolo[4,5-c]quinolin-7-yl)oxy]propyl}-5-(dimethylamino)naphthalene-1-sulfonamide as a light yellow solid, mp 143-146° C. $^1$H NMR (300 MHz, d$_6$-DMSO) δ 8.41 (d, J=8.5, 1H), 8.30 (d, J=8.8, 1H), 8.10 (dd, J=7.2, 1.3, 1H), 7.98 (t, J=6.0, 1H), 7.60-7.55 (m, 2H), 7.20 (d, J=6.9, 1H), 6.88 (d, J=2.6, 1H), 6.75 (s, 2H), 6.71 (dd, J=8.8, 2.5, 1H), 5.74 (s, 1H), 3.93 (t, J=6.0, 2H), 3.11 (t, J=7.6, 2H), 2.98 (q, J=6.7, 2H), 2.77 (s, 6H), 1.88-1.78 (m, 4H), 1.00 (t, J=7.5, 3H); $^{13}$C NMR (75 MHz, d$_6$-DMSO) δ 168.9, 158.9, 152.3, 151.3, 146.4, 139.3, 135.9, 135.8, 129.4, 129.0, 128.3, 127.7, 125.5, 123.4, 118.9, 115.0, 113.0, 112.9, 107.2, 64.6, 44.9, 39.3, 35.0, 28.9, 22.7, 13.4.

Example 7

7-(2-Morpholin-4-yl-2-oxoethoxy)-2-propyl[1,3]thiazolo[4,5-c]quinolin-4-amine

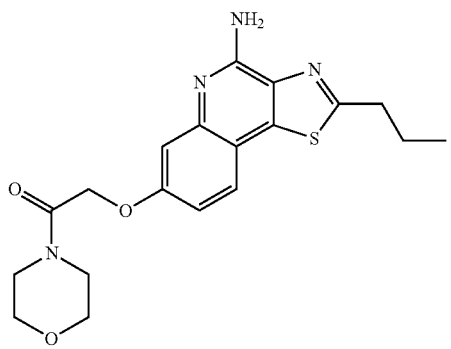 [SMILES: CCCc1nc2c(N)nc3cc(OCC(=O)N4CCOCC4)ccc3c2s1]

Part A

A solution of bromoacetyl bromide (3.0 mL, 0.034 mol) in dichloromethane (240 mL) was cooled to −25° C. A solution of morpholine (9.0 mL, 0.10 mol) in dichloromethane (20 mL) was slowly added over a period of one hour. After the addition was complete, the reaction was stirred at −25° C. for 15 minutes and allowed to warm to ambient temperature. Dichloromethane was added, and the resulting solution was washed with water, 1N aqueous hydrogen chloride, and brine; dried over magnesium sulfate; filtered; and concentrated under reduced pressure to provide 4-(bromoacetyl)morpholine as a colorless oil.

Part B

Under a nitrogen atmosphere, cesium carbonate (4.44 g, 13.6 mmol) was added to a suspension of 2-propyl[1,3]thiazolo[4,5-c]quinolin-7-ol (2.22 g, 9.09 mmol) in DMF (50 mL), and the reaction mixture was heated at 75° C. for 15 minutes. A solution of 4-(bromoacetyl)morpholine (2.26 g, 10.9 mmol) in DMF (10 mL) was added dropwise with stirring. The reaction mixture was stirred at 75° C. for 2.25 hours. The solvent was then removed under reduced pressure at 75° C. The resulting solid was partitioned between dichloromethane (250 mL) and water (250 mL). The organic layer was washed sequentially with water (100 mL) and brine (100 mL), dried over magnesium sulfate, filtered, and concentrated under reduced pressure. The resulting solid was purified by column chromatography using a HORIZON HPFC system (silica cartridge, eluting with 0 to 20% CMA in chloroform), and the purified product was dried under high vacuum to provide 2.84 g of 7-(2-morpholin-4-yl-2-oxoethoxy)-2-propyl[1,3]thiazolo[4,5-c]quinoline as a light yellow solid. A portion of the product (0.37 g) was recrystallized from tert-butyl methyl ether (40 mL), and the crystals were washed with cold tert-butyl methyl ether and dried in a vacuum oven at 40° C. overnight to provide the following analytical data, mp 133-136° C.

Anal. calcd for $C_{19}H_{21}N_3O_3S$: C, 61.44; H, 5.70; N, 11.31. Found: C, 61.26; H, 5.74; N, 11.25.

Part C

The method described in Part G of Example 1 was used to treat 7-(2-morpholin-4-yl-2-oxoethoxy)-2-propyl[1,3]thiazolo[4,5-c]quinoline (2.45 g, 6.60 mmol) with mCPBA (2.28 g of 65% pure material, 8.57 mmol) in dichloromethane (50 mL) to provide 2.58 g of 7-(2-morpholin-4-yl-2-oxoethoxy)-5-oxido-2-propyl[1,3]thiazolo[4,5-c]quinoline as a light yellow solid.

Part D

The method described in Part F of Example 4 was used to treat 7-(2-morpholin-4-yl-2-oxoethoxy)-5-oxido-2-propyl[1,3]thiazolo[4,5-c]quinoline (2.58 g, 6.66 mmol) with ammonium hydroxide (15 mL of 30%) and p-toluenesulfonyl chloride (1.26 g, 7.33 mmol) in 1,2-dichloroethane (60 mL). The reaction was complete in four hours. The resulting light brown solid was purified by column chromatography using a HORIZON HPFC system (silica cartridge, eluting with 0 to 5% CMA in chloroform followed by 25% CMA in chloroform) to provide 1.88 g of a light yellow solid after drying under high vacuum. The solid was recrystallized from 2-propanol (175 mL), and the crystals were washed with cold 2-propanol and dried in a vacuum oven at 60° C. overnight to provide 1.54 g of 7-(2-morpholin-4-yl-2-oxoethoxy)-2-propyl[1,3]thiazolo[4,5-c]quinolin-4-amine as white needles, mp 200-203° C. $^1$H NMR (300 MHz, d$_6$-DMSO) δ 7.68 (d, J=8.7, 1H), 7.02 (d, J=2.5, 1H), 6.92 (dd, J=8.8, 2.5, 1H), 6.80 (s, 2H), 4.93 (s, 2H), 3.61-3.47 (m, 8H), 3.11 (t, J=7.8, 2H), 1.84 (sextet, J=7.2, 2H), 1.02 (t, J=7.5, 3H); $^{13}$C NMR (75 MHz, d$_6$-DMSO) δ 169.1, 165.9, 158.5, 152.4, 146.3, 139.3, 136.0, 125.6, 113.3, 113.0, 107.7, 66.05, 65.9, 44.8, 41.6, 35.1, 22.7, 13.4;

Anal. calcd for $C_{19}H_{22}N_4O_3S$: C, 59.05; H, 5.74; N, 14.50. Found: C, 59.08; H, 5.53; N, 14.20.

Example 8 tert-Butyl 6-[(4-amino-2-propyl[1,3]thiazolo[4,5-c]quinolin-7-yl)oxy]hexylcarbamate

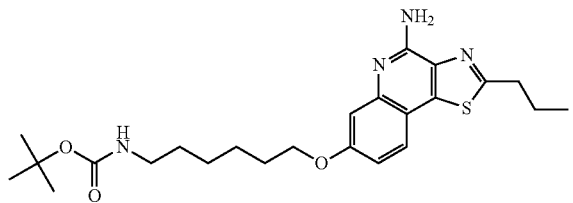 [SMILES: CCCc1nc2c(N)nc3cc(OCCCCCCNC(=O)OC(C)(C)C)ccc3c2s1]

Part A

The methods described in Parts A and B of Example 4 were used to treat 6-amino-1-hexanol (10.0 g, 85.3 mmol) with di-tert-butyl dicarbonate (20.1 g, 92.2 mmol) and treat the resulting product with triphenylphosphine (26.14 g, 99.7 mmol), imidazole (7.92 g, 116.3 mmol), and iodine (27.41 g, 108.0 mmol). The resulting light yellow oil (19.36 g) was purified by column chromatography (silica gel, eluting with dichloromethane) to provide 13.53 g of tert-butyl 6-iodohexylcarbamate as a light yellow oil.

Part B

Under a nitrogen atmosphere, cesium carbonate (2.58 g, 7.92 mmol) was added to a suspension of 2-propyl[1,3]thiazolo[4,5-c]quinolin-7-ol (1.29 g, 5.28 mmol) in DMF (25 mL), and the reaction mixture was heated to 65° C. A solution of tert-butyl 6-iodohexylcarbamate (1.90 g, 5.81 mmol) in DMF (10 mL) was added dropwise with stirring. The reaction mixture was stirred at 65° C. for 5.5 hours. The solvent was then removed under reduced pressure at 65° C. The resulting solid was partitioned between dichloromethane (100 mL) and water (100 mL). The organic layer was washed sequentially with saturated aqueous sodium thiosulfate (50 mL), water (50 mL), and brine (50 mL); dried over magnesium sulfate; filtered; and concentrated under reduced pressure. The resulting solid was purified by column chromatography using a HORIZON HPFC system (silica cartridge, eluting with 0 to 6% CMA in chloroform), and the purified product was dried under high vacuum to provide 1.79 g of tert-butyl 6-[(2-propyl[1,3]thiazolo[4,5-c]quinolin-7-yl)oxy]hexylcarbamate as a light yellow solid.

Part C

The method described in Part G of Example 1 was used to treat tert-butyl 6-[(2-propyl[1,3]thiazolo[4,5-c]quinolin-7-yl)oxy]hexylcarbamate (1.80 g, 4.06 mmol) with mCPBA (1.62 g of 65% pure material, 6.09 mmol) in dichloromethane (30 mL) with the modification that the reaction was stirred for 2.5 hours. tert-Butyl 6-[(5-oxido-2-propyl[1,3]thiazolo[4,5-c]quinolin-7-yl)oxy]hexylcarbamate (1.79 g) was obtained as a light yellow solid.

Part D

The method described in Part F of Example 4 was used to treat tert-butyl 6-[(5-oxido-2-propyl[1,3]thiazolo[4,5-c]quinolin-7-yl)oxy]hexylcarbamate (1.79 g, 3.90 mmol) with ammonium hydroxide (8 mL of 30%) and p-toluenesulfonyl chloride (0.74 g, 4.3 mmol) in 1,2-dichloroethane (40 mL). The reaction was stirred for one hour at 65° C., allowed to come to room temperature, and stirred overnight. The purification methods described in Part F of Example 4 were used, with the modification that chromatographic purification was carried out eluting with 0 to 15% CMA in chloroform, to provide 1.06 g of tert-butyl 6-[(4-amino-2-propyl[1,3]thiazolo[4,5-c]quinolin-7-yl)oxy]hexylcarbamate as off-white needles, mp 136-139° C. $^1$H NMR (300 MHz, $d_6$-DMSO) δ 7.64 (d, J=8.7, 1H), 7.01 (d, J=2.5, 1H), 6.88 (dd, J=9.0, 2.5, 1H), 6.77 (m, 3H), 4.03 (t, J=6.6, 2H), 3.11 (t, J=7.5, 2H), 2.90 (q, J=6.6, 2H), 1.90-1.71 (m, 4H), 1.39-1.30 (m, 15H), 1.00 (t, J=7.1, 3H); $^{13}$C NMR (75 MHz, $d_6$-DMSO) δ 168.9, 159.3, 155.5, 152.3, 146.5, 139.4, 135.9, 125.6, 113.1, 113.0, 107.2, 77.2, 67.4, 35.1, 29.4, 28.6, 28.2, 26.0, 25.2, 22.8, 13.4;

Anal. calcd for $C_{24}H_{34}N_4O_3S$: C, 62.85; H, 7.47; N, 12.22. Found: C, 62.80; H, 7.36; N, 12.18.

Example 9

N-{6-[(4-Amino-2-propyl[1,3]thiazolo[4,5-c]quinolin-7-yl)oxy]hexyl}methanesulfonamide

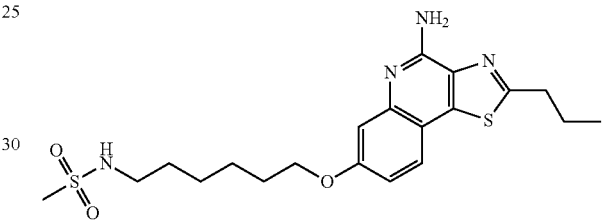

Part A

A solution of hydrogen chloride in ethanol (3 mL of 4.25 M) was added to a suspension of tert-butyl 6-[(4-amino-2-propyl[1,3]thiazolo[4,5-c]quinolin-7-yl)oxy]hexylcarbamate (0.93 g, 2.0 mmol) in ethanol (20 mL), and the reaction was heated at 80° C. for one hour, allowed to cool to room temperature, and concentrated to dryness under reduced pressure. The residue was partitioned between water (50 mL) and dichloromethane (30 mL) was added. The aqueous fraction was made basic with the addition of ammonium hydroxide, and the resulting solution was extracted with dichloromethane (2×50 mL). The organic fractions were combined, washed with brine (75 mL), dried over magnesium sulfate, filtered, and concentrated under reduced pressure to provide 0.73 g of 7-[(6-aminohexyl)oxy]-2-propyl[1,3]thiazolo[4,5-c]quinolin-4-amine.

Part B

Under a nitrogen atmosphere, methanesulfonyl chloride (0.35 mL, 4.1 mmol) was added dropwise to a suspension of 7-[(6-aminohexyl)oxy]-2-propyl[1,3]thiazolo[4,5-c]quinolin-4-amine (0.73 g, 2.0 mmol) and triethylamine (5 mL, 36 mmol) in chloroform (50 mL), and the reaction was stirred overnight. The work-up procedure described in Part B of Example 5 was followed. The resulting light yellow solid was purified by column chromatography using a HORIZON HPFC system (silica cartridge, eluting with 0 to 20% CMA in chloroform) to provide 0.47 g of a light yellow solid after drying under high vacuum. The solid was recrystallized from toluene (25 mL), and the crystals were washed with cold toluene and dried in a vacuum oven at 60° C. overnight to provide 0.32 g of N-{6-[(4-amino-2-propyl[1,3]thiazolo[4,5-c]quinolin-7-yl)oxy]hexyl}methanesulfonamide as off-white needles, mp 138-134° C. $^1$H NMR (300 MHz, $d_6$-DMSO) δ 7.64 (d, J=8.7, 1H), 7.02 (d, J=2.5, 1H), 6.92 (t, J=5.9, 1H), 6.88 (dd, J=8.8, 2.5, 1H), 6.78 (s, 2H), 4.04 (t, J=6.4, 2H), 3.10 (t, J=7.5, 2H), 2.92 (q, J=6.6, 2H), 2.86 (s, 3H), 1.90-1.70 (m, 4H) 1.53-1.33 (m, 6H), 1.00 (t, J=7.5, 3H); $^{13}$C NMR (75 MHz, $d_6$-DMSO) δ 168.9, 159.3, 152.3, 146.5, 139.4, 135.9, 125.6, 113.1, 113.0, 107.2, 67.4, 42.4, 39.2, 35.1, 29.3, 28.5, 25.9, 25.2, 22.7, 13.4;

Anal. calcd for $C_{20}H_{28}N_4O_3S_2$: C, 55.02; H, 6.46; N, 12.83. Found: C, 55.20; H, 6.80; N, 12.68.

Example 10 tert-Butyl 2-{2-[(4-amino-2-propyl[1,3]thiazolo[4,5-c]quinolin-7-yl)oxy]ethoxy}ethylcarbamate

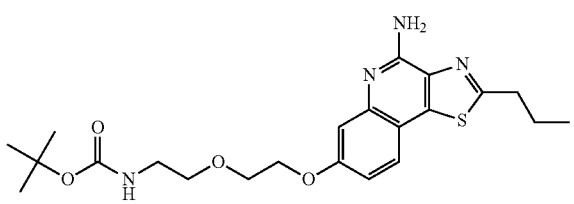 [SMILES: CCCc1nc2c(N)nc3cc(OCCOCCNC(=O)OC(C)(C)C)ccc3c2s1]

Part A

A solution of 2-(2-aminoethoxy)ethanol (15.0 g, 143 mmol) in tetrahydrofuran (THF) (90 mL) was cooled to approximately 0° C., and aqueous sodium hydroxide (72 mL of 2 M) was added over a period of 20 minutes. A solution of di-tert-butyl dicarbonate (31.1 g, 143 mmol) in THF (90 mL) was then added over a period of 20 minutes. The reaction was stirred for one hour at 0° C. and then allowed to warm to room temperature and stirred overnight. The THF was removed under reduced pressure, and the resulting aqueous mixture was adjusted to pH 3 with the addition of 1 M sulfuric acid. The acidic mixture was extracted with ethyl acetate (3×100 mL), and the combined extracts were washed sequentially with water (150 mL) and brine (150 mL), dried over magnesium sulfate, filtered, and concentrated under reduced pressure to provide 27.1 g of tert-butyl 2-(2-hydroxyethoxy)ethylcarbamate as a colorless oil. A portion of the oil (10.0 g, 48.7 mmol) was treated with triphenylphosphine (15.33 g, 58.45 mmol), imidazole (4.64 g, 68.2 mmol), and iodine (16.01 g, 63.3 mmol) according to the method described in Part B of Example 4, with the modification that dichloromethane (325 mL) was used instead of diethyl ether and acetonitrile, to provide 7.82 g of tert-butyl 2-(2-iodoethoxy)ethylcarbamate containing a small amount of triphenylphosphine oxide.

Part B

Under a nitrogen atmosphere, cesium carbonate (1.50 g, 4.61 mmol) was added to a suspension of 2-propyl[1,3]thiazolo[4,5-c]quinolin-7-ol (0.75 g, 3.1 mmol) in DMF (15 mL), and the reaction mixture was heated at 75° C. for 30 minutes. A solution of tert-butyl 2-(2-iodoethoxy)ethylcarbamate (1.93 g, 6.14 mmol) in DMF (5 mL) was added dropwise with stirring. The reaction mixture was stirred at 75° C. for 3.75 hours. The solvent was then removed under reduced pressure at 65° C. The resulting solid was partitioned between dichloromethane (100 mL) and water (100 mL). The organic layer was washed sequentially with water (50 mL) and brine (50 mL), dried over magnesium sulfate; filtered, and concentrated under reduced pressure. The resulting dark brown solid was purified by column chromatography using a HORIZON HPFC system (silica cartridge, eluting with 0 to 8% CMA in chloroform), and the purified product was dried under high vacuum to provide 1.31 g of tert-butyl 2-{2-[(2-propyl[1,3]thiazolo[4,5-c]quinolin-7-yl)oxy]ethoxy}ethylcarbamate as a light yellow solid.

Part C

Under a nitrogen atmosphere, mCPBA (1.20 g, 4.30 mmol, 65% pure) was added in portions to a solution of tert-butyl 2-{2-[(2-propyl[1,3]thiazolo[4,5-c]quinolin-7-yl)oxy]ethoxy}ethylcarbamate (1.25 g, 2.90 mmol) in dichloromethane (75 mL), and the reaction was stirred at room temperature for 1.75 hours, diluted with chloroform (100 mL), and washed with 10% aqueous sodium carbonate (2×50 mL). The aqueous layer was extracted with chloroform (50 mL), and the combined organic fractions were washed with water (75 mL), dried over magnesium sulfate, filtered, concentrated under reduced pressure, and dried under high vacuum to yield 1.23 g of tert-butyl 2-{2-[(5-oxido-2-propyl[1,3]thiazolo[4,5-c]quinolin-7-yl)oxy]ethoxy}ethylcarbamate as a light yellow solid.

Part D

The method described in Part F of Example 4 was used to treat tert-butyl 2-{2-[(5-oxido-2-propyl[1,3]thiazolo[4,5-c]quinolin-7-yl)oxy]ethoxy}ethylcarbamate (1.23 g, 2.75 mmol) with ammonium hydroxide (5 mL of 30%) and p-toluenesulfonyl chloride (0.58 g, 3.0 mmol) in 1,2-dichloroethane (25 mL) with the modifications that the reaction was allowed to run for 16 hours, and chloroform was used instead of dichloromethane in the work-up procedure. The purification methods described in Part F of Example 4 were used, with the modification that chromatographic purification was carried out eluting with 0 to 20% CMA in chloroform, to provide 0.583 g of tert-butyl 2-{2-[(4-amino-2-propyl[1,3]thiazolo[4,5-c]quinolin-7-yl)oxy]ethoxy}ethylcarbamate as light yellow needles, mp 111-113° C. $^1$H NMR (300 MHz, $d_6$-DMSO) δ 7.66 (d, J=8.8, 1H), 7.02 (d, J=2.5, 1H), 6.90 (dd, J=8.8, 2.5, 2H), 6.79 (s, 2H), 4.17 (t, J=4.3, 2H), 3.76 (t, J=4.7, 2H), 3.46 (t, J=5.9, 2H), 3.09 (m, 4H), 1.84 (sextet, J=7.5, 2H), 1.36 (s, 9H), 1.00 (t, J=7.5, 3H); $^{13}$C NMR (75 MHz, $d_6$-DMSO) δ 169.1, 159.0, 155.6, 152.4, 146.5, 139.4, 136.0, 125.7, 113.1, 107.2, 77.6, 69.3, 68.6, 67.1, 35.1, 28.2, 22.8, 13.4;

Anal. calcd for $C_{22}H_{30}N_4O_4S$: C, 59.17; H, 6.77; N, 12.55. Found: C, 58.88; H, 6.87; N, 12.64.

Example 11

N-(2-{2-[(4-Amino-2-propyl[1,3]thiazolo[4,5-c]quinolin-7-yl)oxy]ethoxy}ethyl)methanesulfonamide

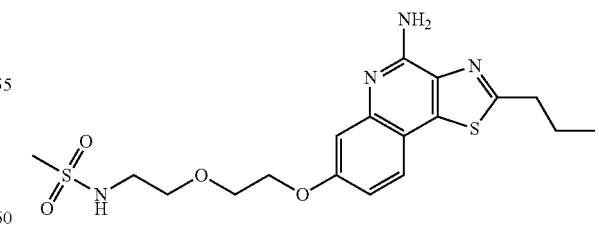

Part A

The method described in Part A of Example 9 was used to treat tert-butyl 2-{2-[(4-amino-2-propyl[1,3]thiazolo[4,5-c]quinolin-7-yl)oxy]ethoxy}ethylcarbamate (0.74 g, 1.7 mmol) in ethanol (20 mL) with hydrogen chloride (3 mL of a 4.25 M solution in ethanol) to provide 0.63 g of 7-[2-(2- aminoethoxy)ethoxy]-2-propyl[1,3]thiazolo[4,5-c]quinolin-4-amine as a light yellow solid.

Part B

The method described in Part B of Example 9 was used to treat 7-[2-(2-aminoethoxy)ethoxy]-2-propyl[1,3]thiazolo[4,5-c]quinolin-4-amine (0.63 g, 1.8 mmol) in chloroform (40 mL) with triethylamine (2.5 mL, 18 mmol) and methanesulfonyl chloride (0.300 mL, 3.64 mmol); the reaction was complete in 3.5 hours. The purification methods described in Part B of Example 9 were used, with the modification that chromatographic purification was carried out eluting with 0 to 30% CMA in chloroform, to provide 0.40 g of N-(2-{2-[(4-amino-2-propyl[1,3]thiazolo[4,5-c]quinolin-7-yl)oxy]ethoxy}ethyl)methanesulfonamide as off-white needles, mp 134-137° C. $^1$H NMR (300 MHz, $d_6$-DMSO) δ 7.66 (d, J=8.7, 1H), 7.07 (t, J=5.6, 1H), 7.03 (d, J=2.5, 1H), 6.90 (dd, J=8.7, 2.5, 1H), 6.80 (s, 2H), 4.19 (t, J=4.3, 2H), 3.79 (t, J=4.7, 2H), 3.55 (t, J=5.9, 2H), 3.16-3.08 (m, 4H), 2.91 (s, 3H), 1.84 (sextet, J=7.5, 2H), 1.00 (t, J=7.5, 3H); $^{13}$C NMR (75 MHz, $d_6$-DMSO) δ 169.0, 159.0, 152.4, 146.5, 139.3, 136.0, 125.7, 113.1, 113.0, 107.2, 69.8, 68.7, 67.1, 42.3, 39.7, 35.1, 22.8, 13.4;

Anal. calcd for $C_{18}H_{24}N_4O_4S_2$: C, 50.92; H, 5.70; N, 13.20. Found: C, 51.20; H, 5.48; N, 13.14.

Example 12 tert-Butyl 2-[(4-amino-2-propyl[1,3]thiazolo[4,5-c]quinolin-7-yl)oxy]ethylcarbamate

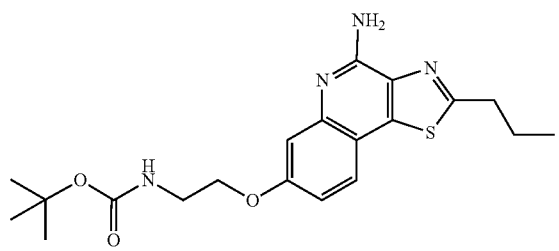 [SMILES: CCCc1nc2c(N)nc3cc(OCCNC(=O)OC(C)(C)C)ccc3c2s1]

Part A

The methods described in Parts A and B of Example 4 were used to treat 2-amino-1-ethanol with di-tert-butyl dicarbonate and treat the resulting product (10.0 g, 62.0 mmol) with triphenylphosphine (19.52 g, 74.5 mmol), imidazole (5.91 g, 86.9 mmol), and iodine (20.47 g, 80.65 mmol), with the modification that dichloromethane (400 mL) was used in the second step instead of diethyl ether and acetonitrile. The product, tert-butyl 2-iodoethylcarbamate (8.41 g) was obtained as a light yellow oil.

Part B

The method described in Part B of Example 10 was used to treat 2-propyl[1,3]thiazolo[4,5-c]quinolin-7-ol (2.94 g, 12.0 mmol) in DMF (40 mL) with cesium carbonate (5.88 g, 18.0 mmol) and a solution of tert-butyl 2-iodoethylcarbamate (4.89 g, 18.0 mmol) in DMF (10 mL). The reaction was complete in 3.25 hours. The purification methods described in Part B of Example 10 were used, with the modification that chromatographic purification was carried out eluting with 0 to 4% CMA in chloroform, to provide 3.85 g of tert-butyl 2-[(2-propyl[1,3]thiazolo[4,5-c]quinolin-7-yl)oxy]ethylcarbamate as a light yellow solid.

Part C

The method described in Part C of Example 10 was used to treat tert-butyl 2-[(2-propyl[1,3]thiazolo[4,5-c]quinolin-7-yl)oxy]ethylcarbamate (3.85 g, 9.94 mmol) with mCPBA (2.57 g of 65% pure material, 14.9 mmol) in dichloromethane to provide 4.01 g of tert-butyl 2-[(5-oxido-2-propyl[1,3]thiazolo[4,5-c]quinolin-7-yl)oxy]ethylcarbamate as a light orange solid.

Part D

The method described in Part F of Example 4 was used to treat tert-butyl 2-[(5-oxido-2-propyl[1,3]thiazolo[4,5-c]quinolin-7-yl)oxy]ethylcarbamate (4.01 g, 9.94 mmol) with ammonium hydroxide (17 mL of 30%) and p-toluenesulfonyl chloride (2.08 g, 10.9 mmol) in 1,2-dichloroethane (85 mL). The reaction was complete in 4.5 hours. The purification methods described in Part F of Example 4 were used to provide 2.84 g of tert-butyl 2-[(4-amino-2-propyl[1,3]thiazolo[4,5-c]quinolin-7-yl)oxy]ethylcarbamate as light yellow needles, mp 136-139° C. $^1$H NMR (500 MHz, $d_6$-DMSO) δ 7.66 (d, J=8.5, 1H), 7.02 (d, J=2.5, 1H), 7.01 (s, 1H), 6.89 (dd, J=8.8, 2.5, 1H), 6.80 (s, 2H), 4.04 (t, J=5.8, 2H), 3.33 (q, J=5.7, 2H), 3.11 (t, J=7.6, 2H), 1.84 (sextet, J=7.5, 2H), 1.38 (s, 9H), 1.00 (t, J=7.2, 3H); $^{13}$C NMR (125 Hz, $d_6$-DMSO) δ 169.0, 159.0, 155.6, 152.4, 146.5, 139.3, 136.0, 125.7, 131.1, 113.0, 107.3, 77.7, 66.4, 35.1, 28.2, 22.7, 13.4;

Anal. calcd for $C_{20}H_{26}N_4O_3S$: C, 59.68; H, 6.51; N, 13.92. Found: C, 59.59; H, 6.18; N, 13.88.

Example 13

N-{2-[(4-Amino-2-propyl[1,3]thiazolo[4,5-c]quinolin-7-yl)oxy]ethyl}methanesulfonamide

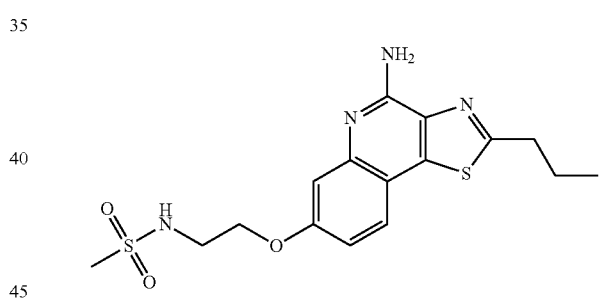

Part A

A solution of hydrogen chloride in ethanol (15 mL of 2.2 M) was added to a suspension of tert-butyl 2-[(4-amino-2-propyl[1,3]thiazolo[4,5-c]quinolin-7-yl)oxy]ethylcarbamate (2.57 g, 6.38 mmol) in ethanol (60 mL), and the reaction was heated at 80° C. overnight. A precipitate began to form after about ten minutes. The solvent was removed under reduced pressure, and the resulting solid was suspended in ethanol (25 mL), isolated by filtration, washed with ethanol, and dried in a vacuum oven at 60° C. to provide 2.06 of 7-(2-aminoethoxy)-2-propyl[1,3]thiazolo[4,5-c]quinolin-4-amine hydrochloride as a light yellow solid.

Part B

Under a nitrogen atmosphere, methanesulfonyl chloride (0.20 mL, 2.5 mmol) was added dropwise to a solution of 7-(2-aminoethoxy)-2-propyl[1,3]thiazolo[4,5-c]quinolin-4-amine hydrochloride (0.64 g, 1.9 mmol) and triethylamine (0.53 mL, 3.8 mmol) in chloroform (40 mL), and the reaction was stirred for 1.25 hours. The work-up procedure described in Part B of Example 5 was followed. The resulting light yellow solid was purified by column chromatography using a HORIZON HPFC system (silica cartridge, eluting with 0 to 25% CMA in chloroform) to provide 0.73 g of an off-white solid after drying under high vacuum. The solid was recrystallized from propyl acetate (35 mL, hot filtration), and the crystals were washed with cold propyl acetate and dried in a vacuum oven at 60° C. overnight to provide 0.48 g of N-{2-[(4-amino-2-propyl[1,3]thiazolo[4,5-c]quinolin-7-yl)oxy]ethyl}methanesulfonamide as light yellow needles, mp 148-151° C.

$^1$H NMR (300 MHz, $d_6$-DMSO) δ 7.68 (d, J=8.7, 1H), 7.30 (t, J=6.0, 1H), 7.03 (d, J=2.5, 1H), 6.92 (dd, J=8.8, 2.5, 1H), 6.81 (s, 2H), 4.13 (t, J=5.6, 2H), 3.38 (q, J=5.6, 2H), 3.11 (t, J=7.1, 2H), 2.95 (s, 3H), 1.84 (sextet, J=7.5, 2H), 1.00 (t, J=7.2, 3H); $^{13}$C NMR (75 Hz, $d_6$-DMSO) δ 169.1, 158.8, 152.4, 146.5, 139.36, 136.0, 125.8, 113.2, 112.9, 107.3, 79.1, 66.9, 41.8, 35.1, 22.8, 13.4;

Anal. calcd for $C_{16}H_{20}N_4O_3S_2$: C, 50.51; H, 5.30; N, 14.72. Found: C, 50.78; H, 5.10; N, 14.67.

Example 14

N,N'-Bis{2-[(4-amino-2-propyl[1,3]thiazolo[4,5-c]quinolin-7-yl)oxy]ethyl}urea

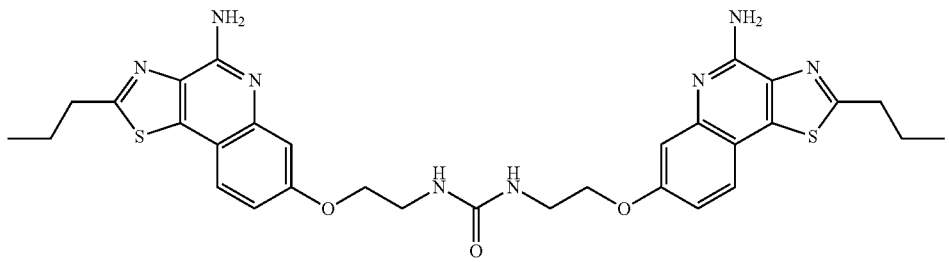 [SMILES: CCCc1nc2c(N)nc3cc(OCCNC(=O)NCCOc4ccc5c(c4)nc(N)c4nc(CCC)sc45)ccc3c2s1]

Under a nitrogen atmosphere, a suspension of 7-(2-aminoethoxy)-2-propyl[1,3]thiazolo[4,5-c]quinolin-4-amine hydrochloride (0.60 g, 2.0 mmol) and carbonyldiimidazole (150 mg, 0.95 mmol) in DMF was heated at 75° C. for four hours. Upon heating a solution formed, and a precipitate began to form after about 30 minutes. The reaction mixture was then combined with material from a smaller run, and the DMF was removed under reduced pressure at 65° C. Water (50 mL) was added to the residue, and the resulting solid was isolated by filtration, washed with water, methanol (25 mL) and tert-butyl methyl ether (25 mL), and dried overnight in a vacuum oven at 80° C. A portion of the solid (250 mg) was suspended in warm DMF (25 mL) and filtered. The DMF was removed under reduced pressure at 65° C. The resulting solid was suspended in chloroform (10 mL), isolated by filtration, washed with chloroform, and dried in a vacuum oven at 60° C. to provide 0.14 mg of N,N'-bis{2-[(4-amino-2-propyl[1,3]thiazolo[4,5-c]quinolin-7-yl)oxy]ethyl}urea as a light yellow solid, mp 213-216° C. $^1$H NMR (500 MHz, $d_6$-DMSO) δ 7.61 (d, J=8.8, 2H), 7.03 (d, J=2.6, 2H), 6.89 (dd, J=8.5, 2.2, 2H), 6.81 (s, 4H), 6.28 (t, J=5.3, 2H), 4.06 (t, J=5.6, 4H), 3.44 (q, J=5.4, 4H), 3.10 (t, J=7.3, 4H), 1.84 (sextet, J=7.6, 4H), 1.00 (t, J=7.2, 6H); $^{13}$C NMR (125 Hz, $d_6$-DMSO) δ 169.0, 159.0, 158.0, 152.4, 146.5, 139.3, 136.0, 125.7, 113.1, 112.9, 107.4, 67.4, 38.8, 35.1, 22.7, 13.4; HRMS (EI) m/z calcd for $C_{31}H_{34}N_8O_3S_2$: 631.2274; found: 631.2283.

Example 15

Bis{2-[(4-amino-2-propyl[1,3]thiazolo[4,5-c]quinolin-7-yl)oxy]ethyl}ether

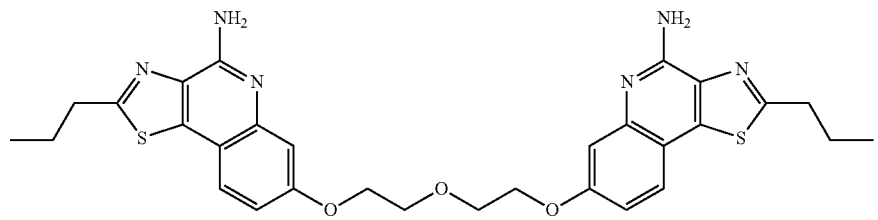 [SMILES: CCCc1nc2c(N)nc3cc(OCCOCCOc4ccc5c(c4)nc(N)c4nc(CCC)sc45)ccc3c2s1]

The method described in Part K of Example 1 was used to treat 4-amino-2-propyl[1,3]thiazolo[4,5-c]quinolin-7-ol acetic acid salt (prepared according to the method described in Part J of Example 1, 1.17 g, 4.51 mmol) in DMF (10 mL) with cesium carbonate (3.27 g, 10.0 mmol) and 2-chloroethylether (288 mg, 2.01 mmol) with the modification that the reaction was carried out at 70° C. instead of 75° C. The purification methods described in Part K of Example 1 were used, with the modification that chromatographic purification was carried out eluting with 0 to 25% CMA in chloroform. Following recrystallization from tert-butyl methyl ether, the solid (0.38 g) was recrystallized from 2-butanone (40 mL, hot filtration), and the crystals were washed with cold 2-butanone and dried in a vacuum oven at 60° C. to provide 0.21 g of bis{2-[(4-amino-2-propyl[1,3]thiazolo[4,5-c]quinolin-7-yl)oxy]ethyl}ether as light yellow needles, mp 186-189° C. $^1$H NMR (500 MHz, d$_6$-DMSO) δ 7.63 (d, J=8.7, 2H), 7.05 (d, J=2.5, 2H), 6.90 (dd, J=8.7, 2.5, 2H), 6.80 (s, 4H), 4.22 (m, 4H), 3.88 (m, 4H), 3.10 (t, J=7.5, 4H), 1.84 (sextet, J=7.5, 4H), 1.00 (t, J=7.2, 6H); $^{13}$C NMR (125 Hz, d$_6$-DMSO) δ 169.0, 159.0, 152.4, 146.5, 139.3, 136.0, 125.7, 113.1, 113.0, 107.3, 69.0, 67.2, 35.1, 22.7, 13.4;

Anal. calcd for C$_{30}$H$_{32}$N$_6$O$_3$S$_2$.0.5 H$_2$O: C, 60.30; H, 5.56; N, 14.06. Found: C, 60.54; H, 5.48; N, 14.16.

Example 16

7-[2-(2-Chloroethoxy)ethoxy]-2-propyl[1,3]thiazolo[4,5-c]quinolin-4-amine

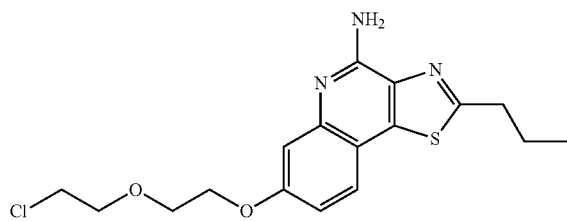 [SMILES: CCCc1nc2c(N)nc3cc(OCCOCCCl)ccc3c2s1]

Part A

The method described in Part B of Example 10 was used to treat 2-propyl[1,3]thiazolo[4,5-c]quinolin-7-ol (1.10 g, 4.50 mmol) in DMF (17 mL) with cesium carbonate (1.76 g, 5.40 mmol) and a solution of 1-chloro-2-(2-iodoethoxy)ethane (1.27 g, 5.40 mmol) in DMF (5 mL). The reaction was complete in 2.75 hours. The purification methods described in Part B of Example 10 were used to provide 1.18 g of 7-[2-(2-chloroethoxy)ethoxy]-2-propyl[1,3]thiazolo[4,5-c]quinoline as a light yellow solid.

Part B

The method described in Part C of Example 10 was used to treat 7-[2-(2-chloroethoxy)ethoxy]-2-propyl[1,3]thiazolo[4,5-c]quinoline (1.2 g, 3.4 mmol) with mCPBA (1.36 g of 65% pure material, 5.13 mmol) in dichloromethane (30 mL). The reaction was complete in 2.5 hours, and 1.03 g of 7-[2-(2-chloroethoxy)ethoxy]-5-oxido-2-propyl[1,3]thiazolo[4,5-c]quinoline were obtained as a light orange solid.

Part C

The methods described in Parts H and I of Example 1 were used to treat 7-[2-(2-chloroethoxy)ethoxy]-5-oxido-2-propyl[1,3]thiazolo[4,5-c]quinoline (1.03 g, 2.81 mmol) in dichloromethane (20 mL) with trichloroacetyl isocyanate (0.40 mL) followed by sodium methoxide (2 mL of a 25% w/w solution in methanol) in methanol (20 mL). The reaction with sodium methoxide was complete within 45 minutes. The crude solid was purified by column chromatography using a HORIZON HPFC system (silica cartridge, eluting with 0 to 20% CMA in chloroform) to provide 0.93 g of a light yellow solid after drying under high vacuum. The solid was recrystallized from tert-butyl methyl ether (35 mL, hot filtration), and the crystals were washed with cold tert-butyl methyl ether and dried in a vacuum oven at 60° C. to provide 0.23 g of 7-[2-(2-chloroethoxy)ethoxy]-2-propyl[1,3]thiazolo[4,5-c]quinolin-4-amine as a light yellow solid, mp 101-103° C. $^1$H NMR (300 MHz, d$_6$-DMSO) δ 7.67 (d, J=8.8, 1H), 7.03 (t, J=2.5, 1H), 6.91 (dd, J=8.7, 2.5, 1H), 6.79 (s, 2H), 4.19 (t, J=4.3, 2H), 3.83 (t, J=4.7, 2H), 3.75 (s, 4H), 3.11 (t, J=7.8, 2H), 1.84 (sextet, J=7.5, 2H), 1.00 (t, J=7.5, 3H); $^{13}$C NMR (75 MHz, d$_6$-DMSO) δ 169.5, 159.4, 152.8, 146.9, 139.8, 136.4, 126.1, 113.6, 113.5, 107.7, 71.0, 69.2, 67.6, 43.9, 35.5, 23.1, 13.8;

Anal. calcd for C$_{17}$H$_{20}$N$_3$O$_2$SCl: C, 55.81; H, 5.51; N, 11.48. Found: C, 55.74; H, 5.40; N, 11.29.

Examples 17-55

A reagent from the table below (1.1 equivalents, 0.11 mmol) was added to a test tube containing a solution of 7-[2-(2-aminoethoxy)ethoxy]-2-propyl[1,3]thiazolo[4,5-c]quinolin-4-amine (prepared as described in Part A of Example 11, 35 mg, 0.10 mmol) and N,N-diisopropylethylamine (36 μL, 0.20 mmol) in N,N-dimethylacetamide (DMA) (1 mL). Each test tube was capped and placed on a shaker at room temperature four hours. Two drops of water were added to each test tube, and then the solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase prep HPLC was performed with non-linear gradient elution from 5-95% B where A is 0.05% trifluoroacetic acid/water and B is 0.05% trifluoroacetic acid/acetonitrile. Fractions were collected by mass-selective triggering. The table below shows the acid chloride, sulfonyl chloride, isocyanate, isothiocyanate, or carbamoyl chloride used for each example, the structure of the resulting compound, and the observed accurate mass for the isolated trifluoroacetate salt.

Examples 17-55

| Example | Reagent | R | Measured Mass (M + H) |
|---|---|---|---|
| 17 | None | –H | 347.1506 |
| 18 | Acetyl chloride | –C(O)CH$_3$ | 389.1625 |
| 19 | Propionyl chloride | –C(O)CH$_2$CH$_3$ | 403.1834 |

-continued

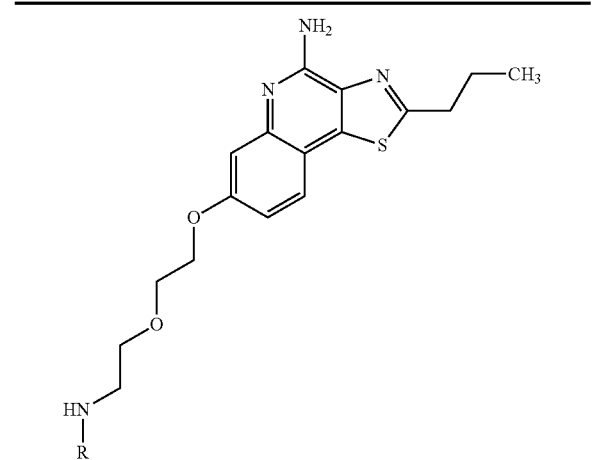

| Example | Reagent | R | Measured Mass (M + H) |
|---|---|---|---|
| 20 | Methyl chloroformate | (methyl carbonate group) | 405.1556 |
| 21 | Cyclopropanecarbonyl chloride | (cyclopropyl carbonyl) | 415.1840 |
| 22 | Butyryl chloride | (propyl carbonyl) | 417.1925 |
| 23 | Cyclohexanecarbonyl chloride | (cyclohexyl carbonyl) | 457.2274 |
| 24 | Hydrocinnamoyl chloride | (phenethyl carbonyl) | 479.2126 |
| 25 | o-Anisoyl chloride | (2-methoxybenzoyl) | 481.1924 |

-continued

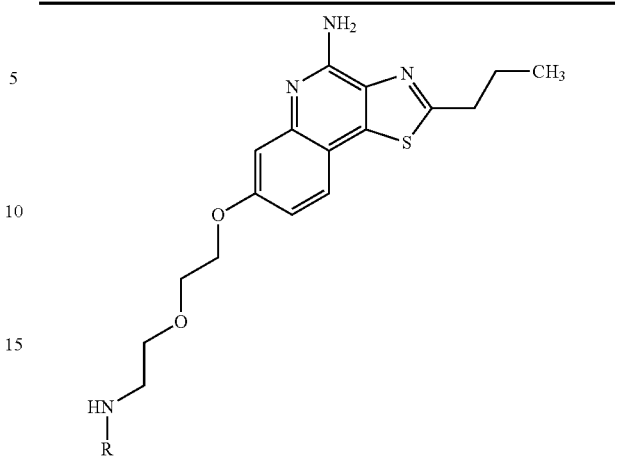

| Example | Reagent | R | Measured Mass (M + H) |
|---|---|---|---|
| 26 | m-Anisoyl chloride | (3-methoxybenzoyl) | 481.1951 |
| 27 | 2-Chlorobenzoyl chloride | (2-chlorobenzoyl) | 485.1414 |
| 28 | 3-Chlorobenzoyl chloride | (3-chlorobenzoyl) | 485.1414 |
| 29 | 4-Chlorobenzoyl chloride | (4-chlorobenzoyl) | 485.1433 |
| 30 | Nicotinoyl chloride hydrochloride | (pyridin-3-yl carbonyl) | 452.1743 |
| 31 | Picolinoyl chloride hydrochloride | (pyridin-2-yl carbonyl) | 452.1712 |

| Example | Reagent | R | Measured Mass (M + H) |
|---|---|---|---|
| 32 | Methanesulfonyl chloride | -S(=O)₂-CH₃ | 425.1312 |
| 33 | Ethanesulfonyl chloride | -S(=O)₂-CH₂CH₃ | 439.1498 |
| 34 | 1-Propanesulfonyl chloride | -S(=O)₂-CH₂CH₂CH₃ | 453.1635 |
| 35 | Benzenesulfonyl chloride | -S(=O)₂-Ph | 487.1468 |
| 36 | 1-Methylimidazole-4-sulfonyl chloride | -S(=O)₂-(1-methylimidazol-4-yl) | 491.1534 |
| 37 | 3-Cyanobenzenesulfonyl chloride | -S(=O)₂-(3-cyanophenyl) | 512.1421 |
| 38 | 4-Cyanobenzenesulfonyl chloride | -S(=O)₂-(4-cyanophenyl) | 512.1395 |
| 39 | 3-Methoxybenzenesulfonyl chloride | -S(=O)₂-(3-methoxyphenyl) | 517.1613 |
| 40 | 4-Methoxybenzenesulfonyl chloride | -S(=O)₂-(4-methoxyphenyl) | 517.1620 |
| 41 | 2-Chlorobenzenesulfonyl chloride | -S(=O)₂-(2-chlorophenyl) | 521.1098 |
| 42 | 3-Chlorobenzenesulfonyl chloride | -S(=O)₂-(3-chlorophenyl) | 521.1101 |
| 43 | 4-Chlorobenzenesulfonyl chloride | -S(=O)₂-(4-chlorophenyl) | 521.1088 |
| 44 | Cyclopropyl isothiocyanate | -C(=S)-NH-cyclopropyl | 446.1678 |
| 45 | Cyclopentyl isocyanate | -C(=O)-NH-cyclopentyl | 458.2220 |

-continued

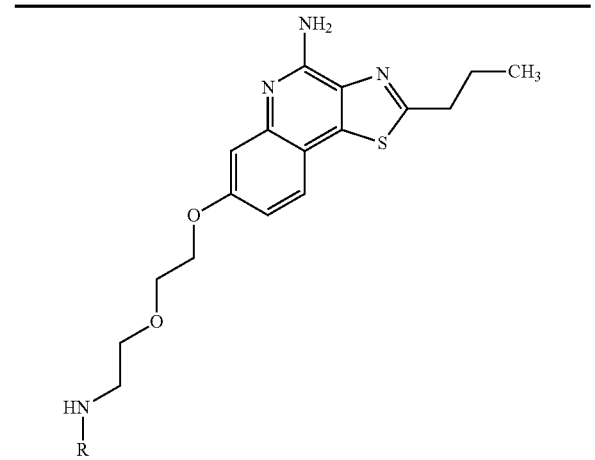

| Example | Reagent | R | Measured Mass (M + H) |
|---|---|---|---|
| 46 | Cyclopropylmethyl isothiocyanate | HN-C(=S)-CH2-cyclopropyl | 460.1844 |
| 47 | Phenyl isocyanate | HN-C(=O)-phenyl | 466.1903 |
| 48 | Cyclohexyl isocyanate | HN-C(=O)-cyclohexyl | 472.2347 |
| 49 | Phenyl isothiocyanate | HN-C(=S)-phenyl | 482.1696 |
| 50 | 2-Phenylethyl isocyanate | HN-C(=O)-CH2CH2-phenyl | 494.2235 |

-continued

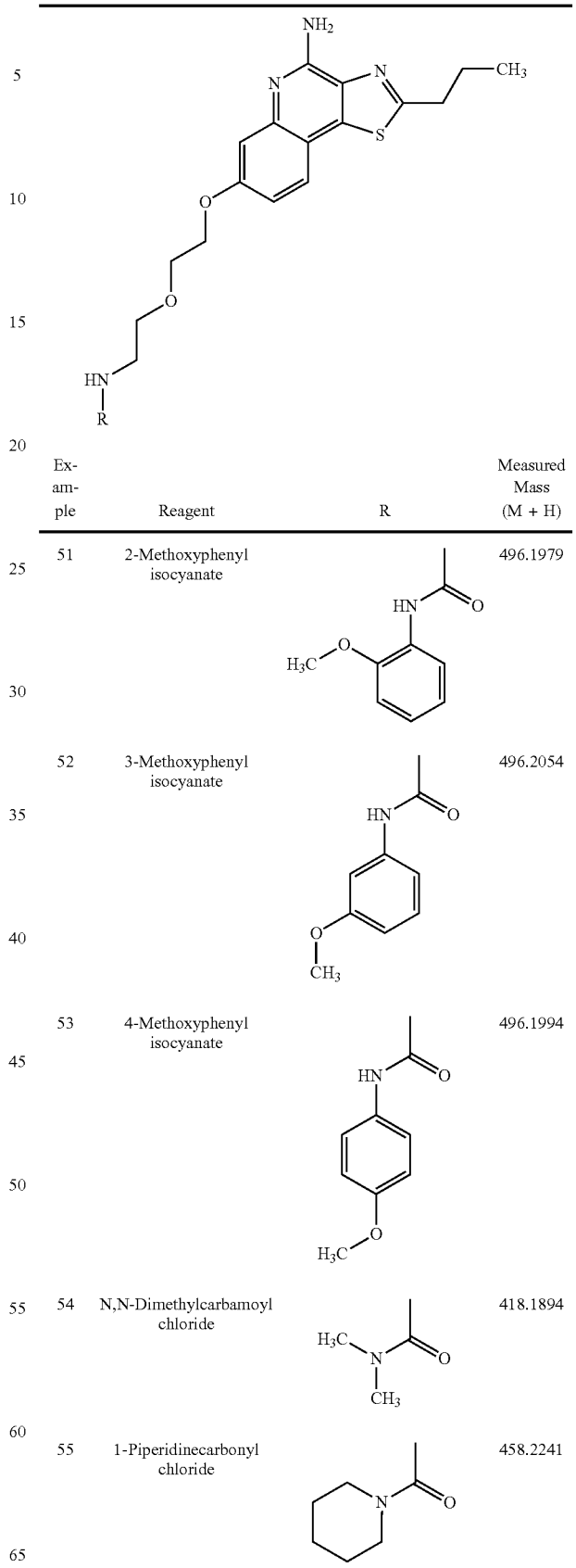

| Example | Reagent | R | Measured Mass (M + H) |
|---|---|---|---|
| 51 | 2-Methoxyphenyl isocyanate | HN-C(=O)-(2-methoxyphenyl) | 496.1979 |
| 52 | 3-Methoxyphenyl isocyanate | HN-C(=O)-(3-methoxyphenyl) | 496.2054 |
| 53 | 4-Methoxyphenyl isocyanate | HN-C(=O)-(4-methoxyphenyl) | 496.1994 |
| 54 | N,N-Dimethylcarbamoyl chloride | (CH3)2N-C(=O)- | 418.1894 |
| 55 | 1-Piperidinecarbonyl chloride | piperidinyl-C(=O)- | 458.2241 |

Examples 56-101

An amine (0.15 mmol, 1.5 equivalents) from the table below was added to a test tube containing 7-[2-(2-chloroethoxy)ethoxy]-2-propyl[1,3]thiazolo[4,5-c]quinolin-4-amine (prepared as described in Example 16, 37 mg, 0.10 mmol) and potassium carbonate (55 mg, 0.40 mmol) in DMA (1 mL). Each tube was capped and heated at 70° C. for 16 hours. An analysis by liquid chromatography/mass spectrometry (LC/MS) indicated the presence of starting material for Examples 59 and 74; therefore, each reaction was heated at 85° C. for six additional hours. Each reaction mixture was filtered, and the filter cake was washed with DMA (0.250 mL). The solvent was then removed from the filtrate by vacuum centrifugation. The compounds were purified using the method described in Examples 17-55. The table below shows the amine added to each test tube, the structure of the resulting compound, and the observed accurate mass for the isolated trifluoroacetate salt.

Examples 56-101

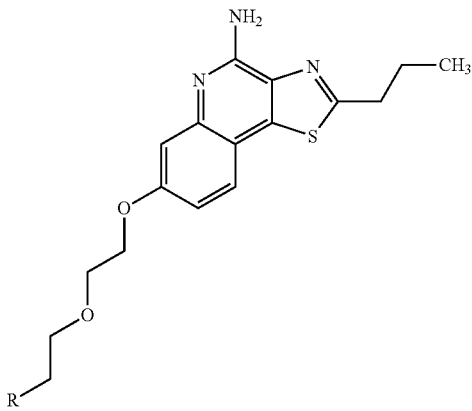

| Example | Reagent | R | Measured Mass (M + H) |
|---|---|---|---|
| 56 | None | Cl– | 366.1057 |
| 57 | Pyrrolidine | pyrrolidinyl | 401.2044 |
| 58 | Piperidine | piperidinyl | 415.2173 |
| 59 | Morpholine | morpholinyl | 417.1958 |
| 60 | 3-Methylpiperidine | 3-methylpiperidinyl | 429.2318 |
| 61 | 4-Methylpiperidine | 4-methylpiperidinyl | 429.2327 |
| 62 | Hexamethyleneimine | hexamethyleneiminyl | 429.2340 |

-continued

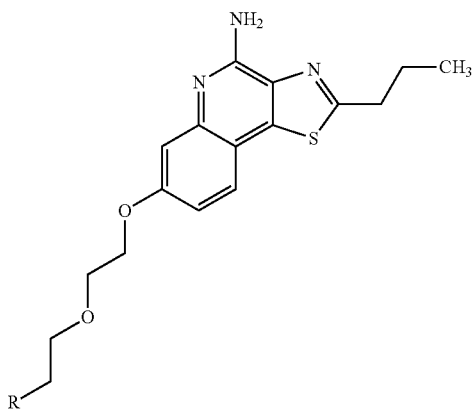

| Example | Reagent | R | Measured Mass (M + H) |
|---|---|---|---|
| 63 | 1-Methylpiperazine | (N-methylpiperazinyl) | 430.2311 |
| 64 | 3-Hydroxypiperidine | (3-hydroxypiperidinyl) | 431.2148 |
| 65 | 4-Hydroxypiperidine | (4-hydroxypiperidinyl) | 431.2130 |
| 66 | Thiomorpholine | (thiomorpholinyl) | 433.1730 |
| 67 | N-Methylcyclohexylamine | (N-methyl-N-cyclohexylamino) | 443.2473 |
| 68 | 3-(Dimethylamino)pyrrolidine | (3-dimethylaminopyrrolidinyl) | 444.2450 |
| 69 | N,N-Dimethyl-3-aminopyrrolidine | (N,N-dimethyl-3-aminopyrrolidinyl) | 444.2456 |

-continued

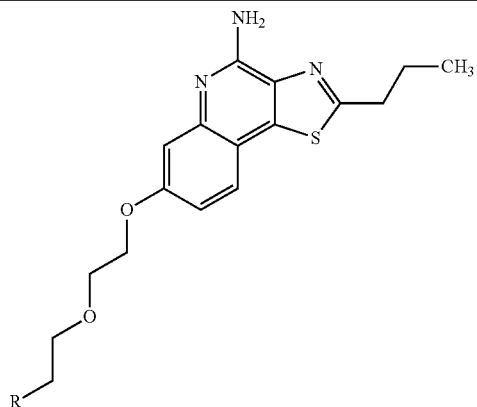

| Example | Reagent | R | Measured Mass (M + H) |
|---|---|---|---|
| 70 | 1-Ethylpiperazine | [piperazine with N-ethyl] | 444.2440 |
| 71 | N-Methylhomopiperazine | [N-methylhomopiperazine] | 444.2461 |
| 72 | 2-Piperidinemethanol | [2-(hydroxymethyl)piperidine, N-substituted] | 445.2307 |
| 73 | 3-(Hydroxymethyl)piperidine | [3-(hydroxymethyl)piperidine, N-substituted] | 445.2292 |
| 74 | 4-(Hydroxymethyl)piperidine | [4-(hydroxymethyl)piperidine, N-substituted] | 445.2270 |
| 75 | N-Methylbenzylamine | [N-methylbenzylamine] | 451.2189 |
| 76 | 3-Azabicyclo[3.2.2]nonane | [3-azabicyclo[3.2.2]nonane] | 455.2492 |

-continued

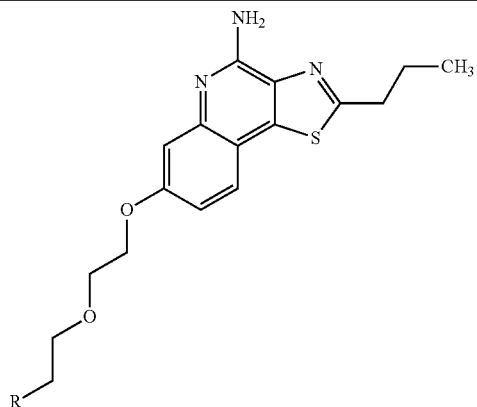

| Example | Reagent | R | Measured Mass (M + H) |
|---|---|---|---|
| 77 | Nipecotamide | 1-methylpiperidin-3-yl carboxamide | 458.2202 |
| 78 | (3S)-(−)-3-Acetamidopyrrolidine | (S)-1-methyl-3-acetamidopyrrolidinyl | 458.2253 |
| 79 | 1-Acetylpiperazine | 4-acetyl-1-methylpiperazinyl | 458.2245 |
| 80 | 1-Methyl-4-(methylamino)piperidine | 1-methyl-4-(dimethylamino)piperidinyl | 458.2549 |
| 81 | Nipecotic acid | 1-methylpiperidine-3-carboxylic acid | 459.2078 |
| 82 | 2-Piperidineethanol | 1-methyl-2-(2-hydroxyethyl)piperidinyl | 459.2423 |

-continued

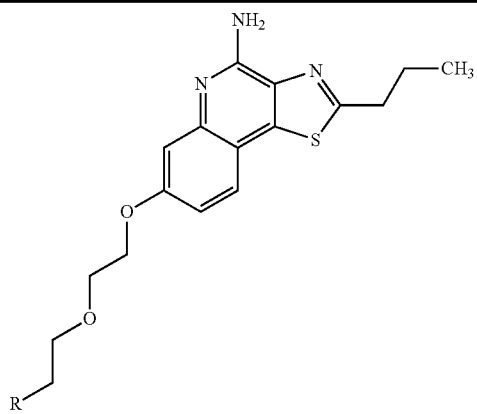

| Example | Reagent | R | Measured Mass (M + H) |
|---|---|---|---|
| 83 | 4-Piperidineethanol | *1-methylpiperidin-4-yl with ethanol substituent* | 459.2415 |
| 84 | N-(2-Hydroxyethyl)piperazine | *4-methylpiperazin-1-yl with ethanol substituent* | 460.2406 |
| 85 | 1,2,3,4-Tetrahydroisoquinoline | *N-methyl-1,2,3,4-tetrahydroisoquinolin-2-yl* | 463.2170 |
| 86 | (R)-(+)-N-Methyl-1-phenylethylamine | *(R)-N,N-dimethyl-1-phenylethylamine* | 465.2357 |
| 87 | (S)-(−)-N-Methyl-1-phenylethylamine | *(S)-N,N-dimethyl-1-phenylethylamine* | 465.2369 |
| 88 | N-Methylphenylethylamine | *N,N-dimethyl-2-phenylethylamine* | 465.2354 |

-continued
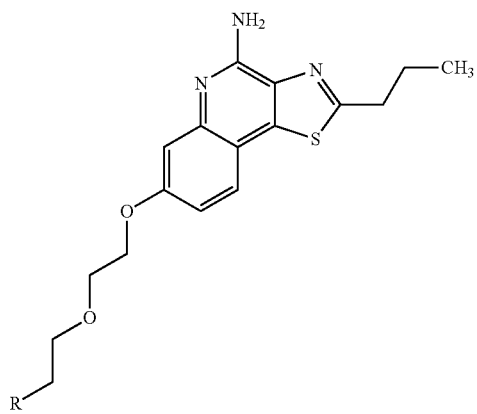
| Example | Reagent | R | Measured Mass (M + H) |
|---|---|---|---|
| 89 | 2-(2-Methylaminoethyl)pyridine | H₃C–N(CH₃)–CH₂CH₂–(2-pyridyl) | 466.2282 |
| 90 | Decahydroisoquinoline | N-methyl decahydroisoquinolinyl | 469.2622 |
| 91 | Decahydroquinoline | N-methyl decahydroquinolinyl | 469.2635 |
| 92 | 1-(2-Methoxyethyl)piperazine | 4-methyl-1-(2-methoxyethyl)piperazinyl | 474.2541 |
| 93 | alpha-(Methylaminomethyl)benzyl alcohol | H₃C–N(CH₃)–CH₂–CH(OH)–Ph | 481.2299 |

-continued
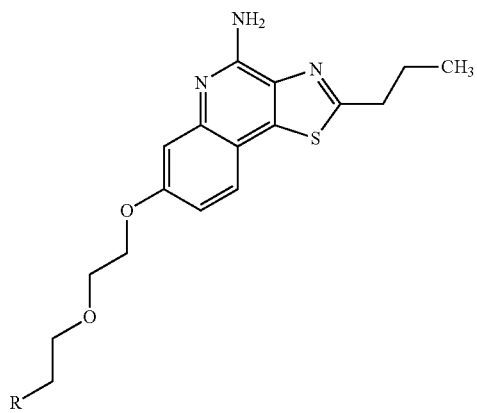
| Example | Reagent | R | Measured Mass (M + H) |
|---|---|---|---|
| 94 | 4-(1-Pyrrolidinyl)piperidine | | 484.2756 |
| 95 | 4-Phenylpiperidine | | 491.2474 |
| 96 | 1-Phenylpiperazine | | 492.2400 |
| 97 | 1-(2-Pyridyl)piperazine | | 493.2390 |
| 98 | 1-(4-Pyridyl)-piperazine | | 493.2389 |
| 99 | 1-(2-Pyrimdyl)piperazine | | 494.2330 |

-continued

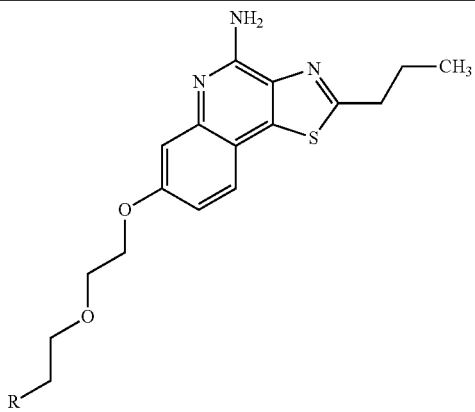

| Example | Reagent | R | Measured Mass (M + H) |
|---|---|---|---|
| 100 | 4-Piperidinopiperidine | (piperidinopiperidine-CH2-) | 498.2913 |
| 101 | 1-Hydroxyethylethoxypiperazine | HO-CH2CH2-O-CH2CH2-N(piperazine)-CH2- | 504.2670 |

Example 102

7-[2-(1,1-Dioxidoisothiazolidin-2-yl)ethoxy]-2-propyl[1,3]thiazolo[4,5-c]quinolin-4-amine

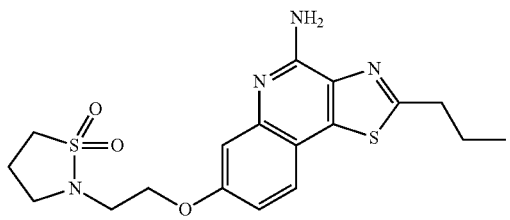 [SMILES: CCCc1nc2c(N)nc3cc(OCCN4CCCS4(=O)=O)ccc3c2s1]

Under a nitrogen atmosphere, 3-chloropropanesulfonyl chloride (0.30 mL, 2.4 mmol) was added dropwise to a solution of 7-(2-aminoethoxy)-2-propyl[1,3]thiazolo[4,5-c]quinolin-4-amine hydrochloride (0.75 g, 2.2 mmol), prepared as described in Example 13 Part A, and triethylamine (0.68 mL, 4.9 mmol) in chloroform (50 mL), and the heterogeneous reaction was stirred overnight at room temperature. An analysis by HPLC indicated the presence of starting material, and additional triethylamine (0.68 mL, 4.9 mmol) was added. The resulting solution was stirred for 2.5 hours at room temperature, diluted with chloroform (100 mL), washed sequentially with water (50 mL) and brine (50 mL), dried over magnesium sulfate, filtered, and concentrated under reduced pressure to provide an orange solid. The solid was dissolved in DMF (15 mL), and the solution was heated to 50° C. under a nitrogen atmosphere. 1,8-Diazabicyclo[5.4.0]undec-7-ene (DBU) (0.42 mL, 2.8 mmol) was added in one portion, and the reaction was stirred at 50° C. for 2.75 hours. The DMF was removed under reduced pressure at 65° C., and the residue was partitioned between chloroform (100 mL) and water (100 mL). The organic layer was separated and washed sequentially with water (50 mL) and brine (50 mL), dried over magnesium sulfate, filtered, and concentrated under reduced pressure. The crude product was purified by column chromatography using a HORIZON HPFC system (silica cartridge, eluting with 0 to 25% CMA in chloroform) followed by recrystallization from propyl acetate (25 mL for 0.35 g). The crystals were washed with cold propyl acetate and dried in a vacuum oven at 60° C. overnight to provide 0.156 g of 7-[2-(1,1-dioxidoisothiazolidin-2-yl)ethoxy]-2-propyl[1,3]thiazolo[4,5-c]quinolin-4-amine as a light yellow solid, mp 127-130° C.

$^1$H NMR (500 MHz, $d_6$-DMSO) δ 7.68 (d, J=8.9, 1H), 7.04 (d, J=2.2, 1H), 6.91 (dd, J=8.8, 2.5, 1H), 6.81 (s, 2H), 4.22 (t, J=5.0, 2H), 3.37-3.28 (m, 4H), 3.19 (t, J=7.6, 2H), 3.11 (t, J=7.6, 2H), 2.24 (quintet, J=7.0, 2H), 1.84 (sextet, J=7.3, 2H), 1.00 (t, J=7.6, 3H);

$^{13}$C NMR (125 Hz, $d_6$-DMSO) δ 169.1, 158.7, 152.4, 146.5, 139.3, 136.0, 125.8, 113.2, 113.0, 107.4, 66.2, 47.7, 45.7, 43.8, 35.1, 22.8, 18.5, 13.4;

Anal. calcd for $C_{18}H_{22}N_4O_3S_2$: C, 53.18; H, 5.46; N, 13.78. Found: C, 53.27; H, 5.41; N, 13.66.

Example 103

N-{2-[(4-Amino-2-propyl[1,3]thiazolo[4,5-c]quinolin-7-yl)oxy]ethyl}acrylamide

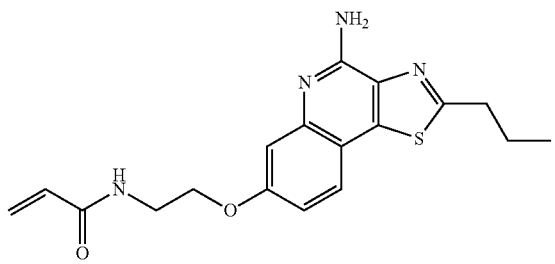 [SMILES: C=CC(=O)NCCOc1ccc2c(c1)nc(N)c1nc(CCC)sc12]

Under a nitrogen atmosphere, 3-chloropropionyl chloride (0.28 mL, 2.9 mmol) was added dropwise to a solution of 7-(2-aminoethoxy)-2-propyl[1,3]thiazolo[4,5-c]quinolin-4-amine hydrochloride (0.90 g, 2.7 mmol), prepared as described in Example 13 Part A, and triethylamine (2.0 mL, 15 mmol) in chloroform (50 mL), and the solution was stirred for 3.5 hours at room temperature. The intermediate was isolated, dissolved in DMF, and treated with DBU (0.50 mL, 3.3 mmol), as described in Example 102 with the modification that the reaction with DBU was heated for 5.25 hours. After the work-up procedure, described in Example 102, the crude product was purified by column chromatography using a HORIZON HPFC system (silica cartridge, eluting with 0 to 28% CMA in chloroform) followed by recrystallization from acetonitrile (50 mL for 0.67 g). The crystals were washed with cold acetonitrile and dried in a vacuum oven at 60° C. overnight to provide 0.426 g of N-{2-[(4-amino-2-propyl[1,3]thiazolo[4,5-c]quinolin-7-yl)oxy]ethyl}acrylamide as a light yellow solid, mp 200-202° C.

$^1$H NMR (500 MHz, $d_6$-DMSO) δ 7.51 (d, J=8.9, 1H), 7.00 (d, J=2.5, 1H), 6.86 (dd, J=8.9, 2.5, 1H), 6.18 (dd, J=17.0, 1.6, 1H), 6.09 (dd, J=17.0, 10.7, 1H), 5.56 (dd, J=10.1, 1.9, 1H), 4.08 (t, J=5.3, 2H), 3.36-3.64 (m, 5H), 3.00 (t, J=7.6, 2H), 1.83 (sextet, J=7.3, 2H), 0.97 (t, J=7.6, 3H);

$^{13}$C NMR (125 Hz, $d_6$-DMSO) δ 170.3, 166.4, 159.4, 151.8, 145.3, 140.9, 136.0, 130.3, 126.5, 125.6, 114.0, 113.8, 107.1, 66.4, 38.7, 35.7, 23.0, 13.3;

Anal. calcd for $C_{18}H_{20}N_4O_2S$: C, 60.65; H, 5.66; N, 15.72. Found: C, 60.64; H, 5.60; N, 15.70.

Example 104

N-{2-[(4-Amino-2-propyl[1,3]thiazolo[4,5-c]quinolin-7-yl)oxy]ethyl}pyrrolidin-2-one

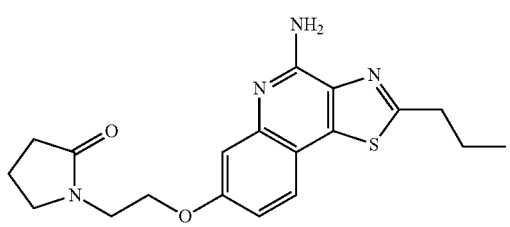 [SMILES: CCCc1nc2c(N)nc3cc(OCCN4CCCC4=O)ccc3c2s1]

Under a nitrogen atmosphere, 4-chlorobutyryl chloride (0.30 mL, 2.6 mmol) was added dropwise to a solution of 7-(2-aminoethoxy)-2-propyl[1,3]thiazolo[4,5-c]quinolin-4-amine hydrochloride (0.81 g, 2.4 mmol), prepared as described in Example 13 Part A, and triethylamine (1.8 mL, 13 mmol) in chloroform (50 mL), and the solution was stirred for 2.5 hours at room temperature. The intermediate was isolated as an orange solid using the procedure described in Example 102. A solution of the orange solid in DMF (15 mL) was slowly added to a mixture of sodium hydride (120 mg of a 60% dispersion in mineral oil, 3.0 mmol) in DMF (5 mL) that had been cooled to 0° C. The resulting mixture was stirred at 0° C. for 15 minutes, allowed to warm to room temperature, and stirred overnight. The DMF was removed under reduced pressure at 65° C., and the residue was partitioned between chloroform (100 mL) and water (100 mL). The organic layer was separated and washed with brine (50 mL), dried over magnesium sulfate, filtered, and concentrated under reduced pressure. The crude product was purified by column chromatography using a HORIZON HPFC system (silica cartridge, eluting with 0 to 25% CMA in chloroform) followed by recrystallization from acetonitrile (25 mL for 0.37 g). The crystals were washed with cold acetonitrile and dried in a vacuum oven at 60° C. to provide 290 mg of N-{2-[(4-amino-2-propyl[1,3]thiazolo[4,5-c]quinolin-7-yl)oxy]ethyl}pyrrolidin-2-one as a light yellow solid, mp 163-166° C.

$^1$H NMR (500 MHz, $d_6$-DMSO) δ 7.67 (d, J=8.5, 1H), 7.04 (d, J=2.5, 1H), 6.89 (dd, J=8.9, 2.5, 1H), 6.81 (s, 2H), 4.17 (t, J=5.7, 2H), 3.58 (t, J=5.4, 2H), 3.47 (t, J=6.9, 2H), 3.11 (t, J=7.5, 2H), 2.21 (t, J=7.8, 2H), 1.94 (quintet, J=7.3, 2H), 1.84 (sextet, J=7.2, 2H), 1.00 (t, J=7.3, 3H);

$^{13}$C NMR (125 Hz, $d_6$-DMSO) δ 174.1, 169.1, 158.8, 152.4, 146.5, 139.3, 136.0, 125.7, 113.2, 113.0, 107.4, 65.5, 47.3, 41.4, 35.1, 30.2, 22.7, 17.6, 13.4;

Anal. calcd for $C_{19}H_{22}N_4O_2S$: C, 61.60; H, 5.99; N, 15.12. Found: C, 61.38; H, 6.18; N, 15.23.

Example 105

2-[(4-Amino-2-ethyl[1,3]thiazolo[4,5-c]quinolin-7-yl)oxy]-1-thien-3-ylethanone

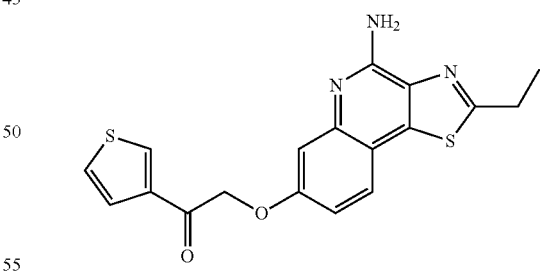

Part A

A Parr vessel was charged with 7-benzyloxy-3-nitroquinolin-7-ol (50.0 g, 169 mmol), anhydrous DMF (500 mL), and 5% platinum on carbon (5.0 g). The vessel was placed on Parr apparatus, evacuated, and charged with hydrogen gas (approximately 45 psi, $3.1 \times 10^5$ Pa). The reaction mixture was shaken overnight and filtered to remove the catalyst. To the resulting dark colored solution was added concentrated aqueous hydrochloric acid (14 mL of 12 N solution). A precipitate formed, and the reaction mixture was stirred over the weekend. The solid was collected by vacuum filtration, washed with diethyl ether (100 mL), and air-dried overnight to provide 44 g of 3-amino-7-benzyloxyquinolin-4-ol hydrochloride.

Part B

To a stirred solution of 3-amino-7-benzyloxyquinolin-4-ol hydrochloride (40.4 g, 133 mmol) and triethylamine (33.8 g, 334 mmol) in dichloromethane (1000 mL) at room temperature, was slowly added propionyl chloride (13.6 g, 147 mmol). After the reaction was stirred for six hours, water (250 mL) was added. The organic layer was separated and concentrated to provide 41.5 g of N-(7-benzyloxy-4-hydroxyquinolin-3-yl)propionamide as a pale tan, crystalline solid. MS (ACPI) m/z 323 (M+H)$^+$.

Part C

To a stirred suspension of the material from Part B in pyridine (500 mL) was added phosphorus pentasulfide (28.6 g, 64.4 mmol). The reaction mixture was heated to reflux and became homogeneous and dark orange. The reaction was heated at reflux overnight and then allowed to cool to room temperature. Aqueous sodium carbonate (50 mL of 10% w/w) was slowly added. The resulting mixture was partitioned between water (200 mL) and dichloromethane (700 mL). The aqueous layer was separated and extracted with dichloromethane (3×100 mL). The organic fractions were combined and concentrated under reduced pressure. The resulting tan solid was treated with boiling heptane (3×400 mL) and filtered. The heptane filtrates were combined and concentrated to provide 15 g of 7-benzyloxy-2-ethyl[1,3]thiazolo[4,5-c]quinoline as a pale yellow crystalline solid. MS (ACPI) m/z=321 (M+H)$^+$.

Part D mCPBA (16.15 g of 50% pure material, 47 mmol) was slowly added in small portions to a stirred solution of 7-benzyloxy-2-ethyl[1,3]thiazolo[4,5-c]quinoline (15.0 g, 46.8 mmol) in chloroform (150 mL). The reaction was stirred at room temperature overnight, washed with 10% aqueous sodium carbonate (2×50 mL), and concentrated under reduced pressure to provide 15.4 g of 7-benzyloxy-2-ethyl-5-oxido[1,3]thiazolo[4,5-c]quinoline as a light tan solid. MS (ACPI) m/z=337 (M+H)$^+$.

Part E

Trichloroacetyl isocyanate (5.6 mL, 46.8 mmol) was slowly added to a vigorously stirred pale orange solution of 7-benzyloxy-2-ethyl-5-oxido[1,3]thiazolo[4,5-c]quinoline (15.0 g, 44.6 mmol) in dichloromethane (200 mL) at room temperature. The solution was maintained at room temperature for 18 hours, and then concentrated ammonium hydroxide solution (60 mL) was added. An off-white precipitate formed and was collected by vacuum filtration. Recrystallization from acetonitrile provided 11.3 g of 7-benzyloxy-2-ethyl[1,3]thiazolo[4,5-c]quinolin-4-amine as a white crystalline solid, mp 208-209° C. MS (APCI) m/z 336.1 (M+H)$^+$; Anal. calcd for $C_{19}H_{17}N_3OS$: C, 68.03; H, 5.11; N, 12.53. Found: C, 67.45; H, 4.83; N, 12.41.

Part F

Hydrogen bromide in acetic acid (40 mL of 45% w/w) was added to 7-benzyloxy-2-ethyl[1,3]thiazolo[4,5-c]quinolin-4-amine (11.3 g, 33.7 mmol), and the resulting solution was heated at 65° C. for two hours and then cooled in an ice bath. Aqueous sodium hydroxide (50% w/w solution) was added slowly to adjust the solution to pH 7, and a pale yellow-green solid formed. The solid was isolated by filtration and air-dried to provide 8.4 g of 4-amino-2-ethyl[1,3]thiazolo[4,5-c]quinolin-7-ol. MS (APCI) m/z 246.0 (M+H)$^+$.

Part G

A mixture of 4-amino-2-ethyl[1,3]thiazolo[4,5-c]quinolin-7-ol (245 mg, 1.0 mmol), cesium carbonate (1.3 g, 4.0 mmol), and DMF (20 mL) was stirred at 75° C. for ten minutes. 2-Bromo-1-(3-thienyl)-1-ethanone (225 mg, 1.1 mmol) was added in portions over a period of 30 minutes. The reaction mixture was stirred for two hours, allowed to cool, and diluted with water (250 mL) A precipitate formed. The mixture was stirred for one hour, and the solid was isolated by filtration. The isolated solid was rinsed with water and then dried to provide a brown powder. This material was dissolved in dichloromethane and then purified by column chromatography using a HORIZON HPFC system (silica cartridge, eluting with a gradient of 0% to 20% CMA in chloroform over 700 mL and then with 200 mL of 20% CMA in chloroform.) The resulting solid was recrystallized from acetonitrile to provide 115 mg of 2-[(4-amino-2-ethyl[1,3]thiazolo[4,5-c]quinolin-7-yl)oxy]-1-thien-3-ylethanone as an off-white solid, mp 202.0-203.0° C. MS (ESI) m/z 370 (M+H)$^+$;

Anal. calcd for $C_{18}H_{15}N_3O_2S_2$: C, 58.52; H, 4.09; N, 11.37. Found C, 58.44; H, 3.91; N, 11.32.

Example 106

7-{3-[(4-Amino-2-ethyl[1,3]thiazolo[4,5-c]quinolin-7-yl)oxy]propoxy}-2-ethyl[1,3]thiazolo[4,5-c]quinolin-4-amine

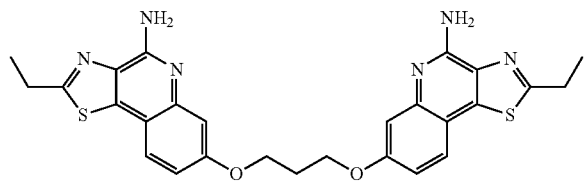 [SMILES: CCc1nc2c(N)nc3cc(OCCCOc4ccc5c(c4)nc(N)c4nc(CC)sc45)ccc3c2s1]

Part A

A mixture of 4-amino-2-ethyl[1,3]thiazolo[4,5-c]quinolin-7-ol (1.00 g, 4.08 mmol), cesium carbonate (5.30 g, 16.3 mmol), and DMF (40 mL) was stirred at 50° C. for ten minutes. A solution of 1-bromo-3-chloropropane (705 mg, 4.48 mmol) in DMF (1.1 mL) was added in portions (0.05 mL) every seven minutes. After two hours, the reaction mixture was poured into water (225 mL). The mixture was stirred for 30 minutes and then filtered. The isolated solid was dried to provide 785 mg of 7-(3-chloropropoxy)-2-ethyl[1,3]thiazolo[4,5-c]quinolin-4-amine as a brown solid.

Part B

A solution of 7-(3-chloropropoxy)-2-ethyl[1,3]thiazolo[4,5-c]quinolin-4-amine (684 mg, 2.12 mmol) in DMF (20 mL) was heated to 110° C. Sodium azide (151 mg, 2.33 mol) was added in a single portion. After one hour the reaction mixture was poured into water (100 mL). The mixture was extracted with chloroform (3×100 mL). The combined extracts were concentrated under reduced pressure. The residue was dissolved in chloroform and purified by column chromatography using a HORIZON HPFC system (eluting with a gradient of 0% to 20% CMA in chloroform over 700 mL and then with 20% CMA in chloroform for 600 mL). The major product isolated from the column fractions was 7-(3-azidopropoxy)-2-ethylthiazolo[4,5-c]quinolin-4-amine (400 mg). A second product isolated from the column was triturated with hot acetonitrile containing a small amount of methanol, and the mixture was allowed to cool to room temperature. The resulting solid was isolated by filtration to provide 75 mg of 7-{3-[(4-amino-2-ethyl[1,3]thiazolo[4,5-c]quinolin-7-yl)oxy]propoxy}-2-ethyl[1,3]thiazolo[4,5-c]quinolin-4-amine as an off-white solid, mp 242.0-243.0° C.

MS (APCI) m/z 531 (M+H)+;

Anal. calcd for $C_{27}H_{26}N_6O_2S_2$: C, 61.11; H, 4.94; N, 15.84. Found C, 60.90; H, 4.72; N, 15.71.

Example 107

3-[(4-Amino-2-propyl[1,3]thiazolo[4,5-c]quinolin-7-yl)oxy]propan-1-ol

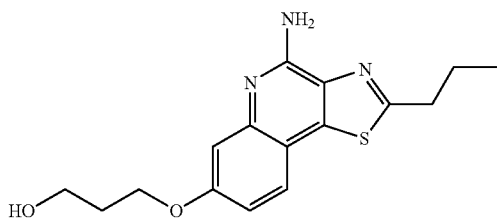 [SMILES: CCCc1nc2c(N)nc3cc(OCCCO)ccc3c2s1]

A mixture of 4-amino-2-ethyl[1,3]thiazolo[4,5-c]quinolin-7-ol acetic acid salt (see Parts A through J of Example 1) (0.640 g, 2.01 mmol), cesium carbonate (2.6 g, 8.0 mmol), and DMF (20 mL) was stirred at 75° C. for ten minutes. A solution of 1-bromo-3-chloropropane (0.350 g, 2.21 mmol) in DMF (10 mL) was added dropwise over a period of 30 minutes. The reaction was stirred at 75° C. for three hours, allowed to cool to room temperature, and poured into deionized water (200 mL). Brine (25 mL) was added, and a precipitate formed. The resulting mixture was stirred for one hour, and the solid was then collected by filtration. The solid was stirred in a mixture of potassium carbonate and methanol overnight, and the mixture was then filtered through a 0.2 micron TEFLON filter. Chloroform was added during the filtration. The filtrate was concentrated under reduced pressure, and the residue was partitioned between chloroform and water. The organic fraction was concentrated under reduced pressure, and the residue was purified by column chromatography using a HORIZON HPFC system (eluting with a gradient of 0% to 20% CMA in chloroform over 900 mL and then with 20% CMA in chloroform for 500 mL). The resulting solid (400 mg) was recrystallized from acetonitrile to provide 100 mg of 3-[(4-amino-2-propyl[1,3]thiazolo[4,5-c]quinolin-7-yl)oxy]propan-1-ol as an off-white solid, mp 157.0-160.0° C.

MS (APCI) m/z 318 (M+H)+;

Anal. calcd for $C_{16}H_{19}N_3O_2S$: C, 60.55; H, 6.03; N, 13.24. Found C, 60.32; H, 5.97; N, 13.33.

Examples 108-127

Part A

A solution of 4-hydroxypiperidine (10.00 g, 98.86 mmol), triethylamine (27.55 mL, 197.7 mmol), and dichloromethane (100 mL) was cooled to approximately 0° C. under a nitrogen atmosphere. Di-tert-butyl dicarbonate (23.73 g, 108.7 mmol) was added over a period of five minutes. The reaction was allowed to warm to room temperature slowly and stirred overnight and then added slowly with vigorous stirring to a cold (0° C.) solution of acetic acid (50 mL of 15% w/w in water). The organic layer was separated and washed sequentially with 15% w/w acetic acid in water (50 mL) and saturated aqueous sodium bicarbonate (3×33 mL), dried over sodium sulfate, filtered, and concentrated under reduced pressure to provide tert-butyl 4-hydroxypiperidine-1-carboxylate as a golden oil that slowly solidified to an off-white solid.

Part B

A solution of diisopropyldiazodicarboxylate (4.63 mL, 23.5 mmol) was added dropwise over a period of two minutes to a solution of 2-propyl[1,3]thiazolo[4,5-c]quinolin-7-ol (prepared as described in Parts A through C of Example 4, 5.00 g, 20.5 mmol), tert-butyl 4-hydroxypiperidine-1-carboxylate (4.74 g, 23.5 mmol), and triphenylphosphine (6.16 g, 23.5 mmol) in tetrahydrofuran (150 mL) at 0° C. The resulting solution was allowed to warm to room temperature and stirred for 15 hours. A precipitate was present and was removed by filtration. The filtrate was concentrated under reduced pressure. The crude product was purified by column chromatography using a HORIZON HPFC system (silica cartridge, eluting with 5% CMA in chloroform). The resulting oil was treated with boiling tert-butyl methyl ether, and a precipitate formed. The precipitate was removed by filtration, and the filtrate was concentrated under reduced pressure. The residue was recrystallized from methanol to provide 3.76 g tert-butyl 4-[(2-propyl[1,3]thiazolo[4,5-c]quinolin-7-yl)oxy]piperidine-1-carboxylate as a white solid. The mother liquor was concentrated under reduced pressure to provide an additional 6.24 g of product containing some triphenylphosphine oxide.

Part C mCPBA (1.97 g of 70% pure material, 11 mmol) was added to a solution of tert-butyl 4-[(2-propyl[1,3]thiazolo[4,5-c]quinolin-7-yl)oxy]piperidine-1-carboxylate (3.76 g, 8.79 mmol), and the reaction was stirred at room temperature for 1.5 hours. An analysis by LC/MS indicated the presence of starting material, and additional mCPBA (250 mg) was added. The reaction was stirred at room temperature for an additional 1.5 hours; diluted with chloroform (20 mL); washed sequentially with aqueous sodium carbonate (20 mL of 10% w/w), water (20 mL), and brine (20 mL); dried over sodium sulfate; filtered; and concentrated under reduced pressure to provide tert-butyl 4-[(5-oxido-2-propyl[1,3]thiazolo[4,5-c]quinolin-7-yl)oxy]piperidine-1-carboxylate as a light yellow solid.

Part D

A solution of the material from Part C in 1,2-dichloroethane (60 mL) was heated to 65° C. in a pressure vessel. Aqueous ammonium hydroxide (20 mL of 30% w/w) and p-toluenesulfonyl chloride (1.76 g, 9.23 mmol) were quickly added, and the vessel was sealed and heated at 70° C. for 15 hours and allowed to cool to room temperature. The organic layer was separated and washed sequentially with aqueous sodium carbonate (20 mL of 10% w/w) and water (20 mL). The combined aqueous fractions were extracted with chloroform (20 mL). The combined organic fractions were washed with brine (25 mL), dried over sodium sulfate, filtered, and concentrated under reduced pressure. The crude product was purified by column chromatography using a HORIZON HPFC system (silica cartridge, eluting with 0% to 10% CMA in chloroform) to provide 2.07 g of tert-butyl 4-[(4-amino-2-propyl[1,3]thiazolo[4,5-c]quinolin-7-yl)oxy]piperidine-1-carboxylate as a yellow solid.

Part E

A solution of hydrogen chloride (8 mL of 3.0 M in ethanol) was added to a solution of tert-butyl 4-[(4-amino-2-propyl[1,3]thiazolo[4,5-c]quinolin-7-yl)oxy]piperidine-1-carboxylate (2.07 g, 4.68 mmol) in ethanol (16 mL), and the resulting solution was heated at 100° C. for 30 minutes. A precipitate formed, and the mixture was allowed to cool to room temperature and diluted with diethyl ether (25 mL). The precipitate was collected by filtration, washed with diethyl ether, and dried under vacuum overnight. The solid was suspended in a small volume of water, and the suspension was cooled to approximately 0° C. and adjusted to approximately pH 10 with the addition of 50% w/w aqueous sodium hydroxide. A yellow precipitate formed and was collected by filtration, washed with water, and dried overnight under vacuum. The solid was purified by column chromatography using a HORIZON HPFC system (silica cartridge, eluting with 0% to 15% CMA in chloroform) followed by recrystallization from acetonitrile. The crystals were dried to provide 7-(piperidin-4-yloxy)-2-propyl[1,3]thiazolo[4,5-c]quinolin-4-amine as yellow crystals.

$^1$H NMR (300 MHz, DMSO-$d_6$) δ 7.65 (d, J=8.7 Hz, 1 H), 7.03 (d, J=2.4 Hz, 1 H), 6.90 (dd, J=8.7, 2.4 Hz, 1 H), 6.77 (s, 2 H), 4.54-4.46 (m, 1 H), 3.12 (t, J=7.3 Hz, 2 H), 2.99-2.92 (m, 2 H), 2.64-2.55 (m, 2 H), 1.99-1.93 (m, 3 H), 1.85 (q, J=7.4 Hz, 2 H), 1.54-1.42 (m, 2 H), 1.01 J=7.3 Hz, 3 H); MS (APCI) m/z 343.16 (M+H)$^+$.

Part F

A reagent from the table below (1.1 equivalents, 0.11 mmol) was added to a test tube containing a solution of 7-(piperidin-4-yloxy)-2-propyl[1,3]thiazolo[4,5-c]quinolin-4-amine (34 mg, 0.10 mmol) and N,N-diisopropylethylamine (35 µL, 0.20 mmol) in DMA (1 mL). Each test tube was capped and vortexed overnight. Water (100 µL) was added to each test tube, and then the solvent was removed by vacuum centrifugation. The compounds were purified by prep HPLC according to the method described in Examples 17-55. The table below shows the acid chloride, sulfonyl chloride, or isocyanate used for each example, the structure of the resulting compound, and the observed accurate mass for the isolated trifluoroacetate salt.

Examples 108-127

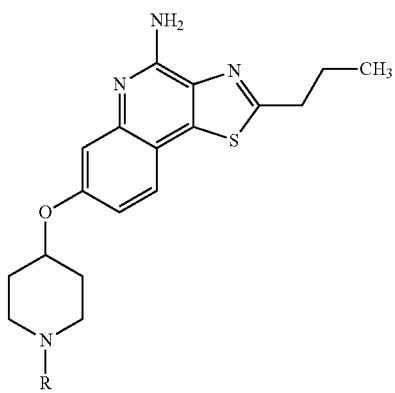

| Example | Reagent | R | Measured Mass (M + H) |
|---|---|---|---|
| 108 | None | H | 343.1575 |
| 109 | Acetyl chloride | H₃C-C(=O)- | 385.1675 |
| 110 | Propionyl chloride | -C(=O)CH₂CH₃ | 399.1830 |
| 111 | Cyclopropanecarbonyl chloride | -C(=O)-cyclopropyl | 411.1852 |
| 112 | Butyryl chloride | -C(=O)CH₂CH₂CH₃ | 413.1994 |
| 113 | Isobutyryl chloride | -C(=O)CH(CH₃)₂ | 413.1981 |
| 114 | Cyclopentanecarbonyl chloride | -C(=O)-cyclopentyl | 439.2160 |
| 115 | Cyclohexanecarbonyl chloride | -C(=O)-cyclohexyl | 453.2302 |
| 116 | Ethanesulfonyl chloride | -S(=O)₂CH₂CH₃ | 435.1503 |
| 117 | 1-Propanesulfonyl chloride | -S(=O)₂CH₂CH₂CH₃ | 449.1667 |

| Example | Reagent | R | Measured Mass (M + H) |
|---|---|---|---|
| 118 | Isopropylsulfonyl chloride | H3C-CH(CH3)-S(=O)2- | 449.1693 |
| 119 | 1-Butanesulfonyl chloride | CH3CH2CH2CH2-S(=O)2- | 463.1841 |
| 120 | Methyl isocyanate | -C(=O)NH-CH3 | 400.1782 |
| 121 | Ethyl isocyanate | -C(=O)NH-CH2CH3 | 414.1935 |
| 122 | Isopropyl isocyanate | -C(=O)NH-CH(CH3)2 | 428.2093 |
| 123 | n-Propyl isocyanate | -C(=O)NH-CH2CH2CH3 | 428.2105 |
| 124 | Cyclopropyl isothiocyanate | -C(=S)NH-cyclopropyl | 442.1723 |
| 125 | Cyclopentyl isocyanate | -C(=O)NH-cyclopentyl | 454.2264 |
| 126 | Cyclohexyl isocyanate | -C(=O)NH-cyclohexyl | 468.2426 |
| 127 | 4-Morpholinylcarbonyl chloride | -C(=O)-morpholinyl | 456.2072 |

Examples 128-148

A reagent from the table below (1.1 equivalents, 0.11 mmol) was added to a test tube containing a solution of 7-(2-aminoethoxy)-2-propyl[1,3]thiazolo[4,5-c]quinolin-4-amine hydrochloride, prepared as described in Example 13, Part A, (33.3 mg, 0.10 mmol) and N,N-diisopropylethylamine (85 μL, 0.49 mmol) in DMA (1 mL). Each test tube was capped and vortexed overnight. Water (two drops) was added to each test tube, and then the solvent was removed by vacuum centrifugation. The compounds were purified by prep HPLC according to the method described in Examples 17-55. The table below shows the acid chloride, sulfonyl chloride, or isocyanate used for each example, the structure of the resulting compound, and the observed accurate mass for the isolated trifluoroacetate salt.

Examples 128-148

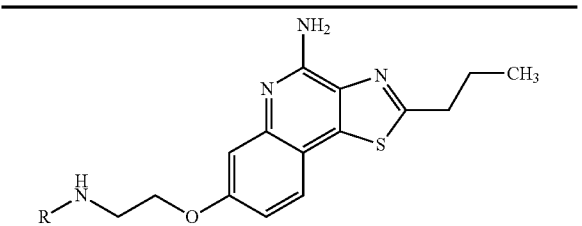

| Example | Reagent | R | Measured Mass (M + H) |
|---|---|---|---|
| 128 | None | H— | 303.1298 |
| 129 | Cyclopropanecarbonyl chloride | cyclopropyl-C(=O)– | 371.1510 |
| 130 | Isobutyryl chloride | (CH3)2CH-C(=O)– | 373.1663 |
| 131 | Cyclopentanecarbonyl chloride | cyclopentyl-C(=O)– | 399.1880 |
| 132 | Benzoyl chloride | Ph-C(=O)– | 407.1519 |
| 133 | Isonicotinoyl chloride hydrochloride | 4-pyridyl-C(=O)– | 408.1518 |
| 134 | Nicotinoyl chloride hydrochloride | 3-pyridyl-C(=O)– | 408.1521 |
| 135 | Methanesulfonyl chloride | CH3-S(=O)2– | 381.1058 |
| 136 | Ethanesulfonyl chloride | CH3CH2-S(=O)2– | 395.1172 |
| 137 | Dimethylsulfamoyl chloride | (CH3)2N-S(=O)2– | 410.1331 |

-continued

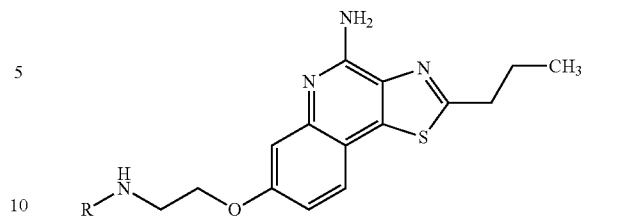

| Example | Reagent | R | Measured Mass (M + H) |
|---|---|---|---|
| 138 | Benzenesulfonyl chloride | Ph-S(=O)2– | 443.1214 |
| 139 | 1-Methylimidazole-4-sulfonyl chloride | (1-methylimidazol-4-yl)-S(=O)2– | 447.1289 |
| 140 | 2,2,2-Trifluoroethanesulfonyl chloride | CF3CH2-S(=O)2– | 449.0932 |
| 141 | n-Propyl isocyanate | CH3CH2CH2-NH-C(=O)– | 388.1840 |
| 142 | Cyclopentyl isocyanate | cyclopentyl-NH-C(=O)– | 414.1980 |
| 143 | Phenyl isocyanate | Ph-NH-C(=O)– | 422.1646 |
| 144 | Cyclohexyl isocyanate | cyclohexyl-NH-C(=O)– | 428.2161 |
| 145 | N,N-Dimethylcarbamoyl chloride | (CH3)2N-C(=O)– | 374.1687 |
| 146 | 1-Pyrrolidinecarbonyl chloride | pyrrolidin-1-yl-C(=O)– | 400.1770 |

-continued

| Example | Reagent | R | Measured Mass (M + H) |
|---|---|---|---|
| 147 | 1-Piperidinecarbonyl chloride | *piperidine-C(=O)-* | 414.1926 |
| 148 | 4-Morpholinylcarbonyl chloride | *morpholine-C(=O)-* | 416.1797 |

Examples 149-189

A phenol (0.165 mmol, 1.5 equivalents) from the table below was added to a test tube containing 7-[2-(2-chloroethoxy)ethoxy]-2-propyl[1,3]thiazolo[4,5-c]quinolin-4-amine (prepared as described in Example 16, 40.3 mg, 0.11 mmol) and potassium carbonate (55 mg, 0.40 mmol) in DMA (1 mL). Each tube was capped and heated at 85° C. overnight. Each reaction mixture was filtered, and the filter cake was washed with DMA (0.200 mL). The solvent was then removed from the filtrate by vacuum centrifugation. The compounds were purified using the method described in Examples 17-55. The table below shows the phenol added to each test tube, the structure of the resulting compound, and the observed accurate mass for the isolated trifluoroacetate salt.

Examples 149-189

| Example | Reagent | R | Measured Mass (M + H) |
|---|---|---|---|
| 16 | None | Cl– | 366.1035 |
| 149 | Phenol | *phenoxy* | 424.1713 |
| 150 | m-Cresol | *3-methylphenoxy* | 438.1844 |
| 151 | o-Cresol | *2-methylphenoxy* | 438.1863 |
| 152 | p-Cresol | *4-methylphenoxy* | 438.1847 |
| 153 | 2-Fluorophenol | *2-fluorophenoxy* | 442.1598 |
| 154 | 3-Fluorophenol | *3-fluorophenoxy* | 442.1601 |

121
-continued

[Structure: 4-amino-2-propyl-thiazoloquinoline with 7-O-CH₂CH₂-O-CH₂CH₂-R substituent]

| Example | Reagent | R | Measured Mass (M + H) |
|---|---|---|---|
| 155 | 4-Fluorophenol | 4-fluoro-phenoxy | 442.1590 |
| 156 | 2-Cyanophenol | 2-cyano-phenoxy | 449.1609 |
| 157 | 3-Cyanophenol | 3-cyano-phenoxy | 449.1630 |
| 158 | 4-Cyanophenol | 4-cyano-phenoxy | 449.1649 |
| 159 | 2,3-Dimethylphenol | 2,3-dimethyl-phenoxy | 452.2024 |

122
-continued

[Structure: 4-amino-2-propyl-thiazoloquinoline with 7-O-CH₂CH₂-O-CH₂CH₂-R substituent]

| Example | Reagent | R | Measured Mass (M + H) |
|---|---|---|---|
| 160 | 2,4-Dimethylphenol | 2,4-dimethyl-phenoxy | 452.2026 |
| 161 | 2,5-Dimethylphenol | 2,5-dimethyl-phenoxy | 452.1971 |
| 162 | 3,4-Dimethylphenol | 3,4-dimethyl-phenoxy | 452.1993 |
| 163 | 3-Methoxyphenol | 3-methoxy-phenoxy | 454.1823 |
| 164 | 4-Methoxyphenol | 4-methoxy-phenoxy | 454.1813 |

123
-continued
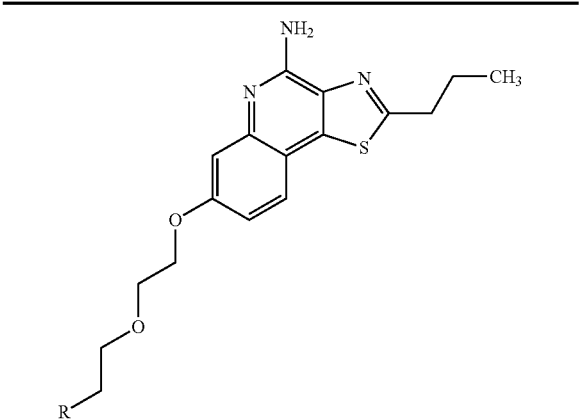
| Example | Reagent | R | Measured Mass (M + H) |
|---|---|---|---|
| 165 | 2-Chlorophenol | 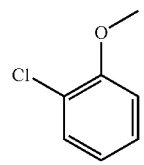 | 458.1309 |
| 166 | 3-Chlorophenol | 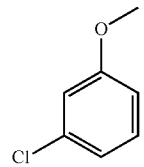 | 458.1305 |
| 167 | 4-Chlorophenol | 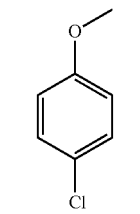 | 458.1325 |
| 168 | 4'-Hydroxyacetophenone | 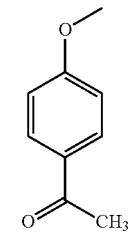 | 466.1804 |
| 169 | 3'-Hydroxyacetophenone | 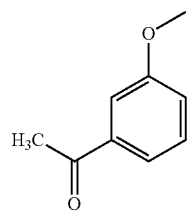 | 466.1821 |
124
-continued
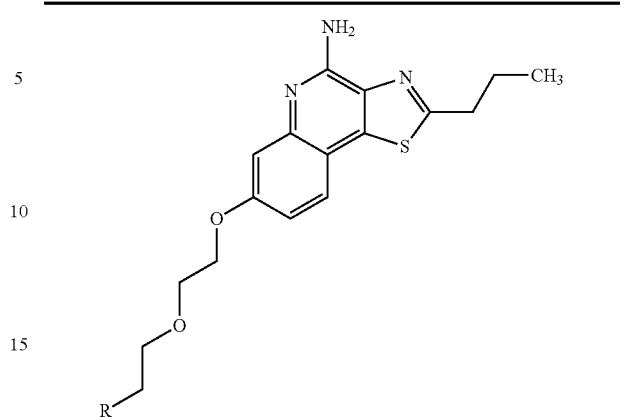
| Example | Reagent | R | Measured Mass (M + H) |
|---|---|---|---|
| 170 | 4-Hydroxybenzamide | 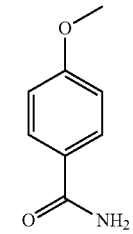 | 467.1742 |
| 171 | Salicylamide | 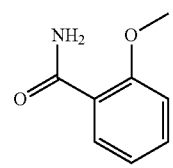 | 467.1720 |
| 172 | 2-Nitrophenol | 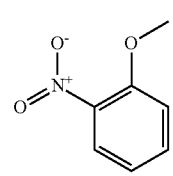 | 469.1570 |
| 173 | 3-Nitrophenol | 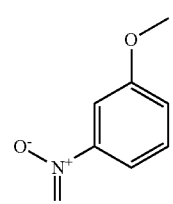 | 469.1559 |
| 174 | 4-Nitrophenol | 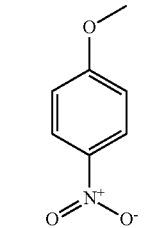 | 469.1566 |

125
-continued
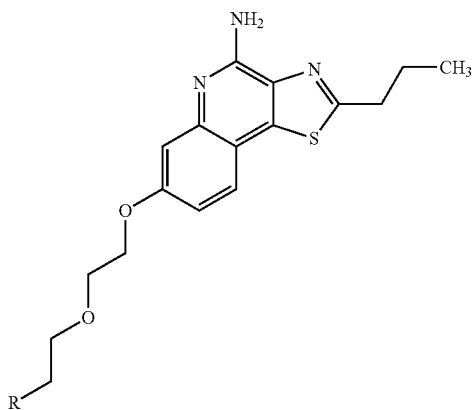
| Example | Reagent | R | Measured Mass (M + H) |
|---|---|---|---|
| 175 | (2-Hydroxy)thioanisole | 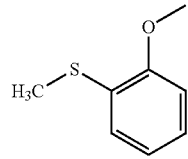 | 470.1526 |
| 176 | 4-(Methylmercapto)phenol | 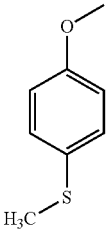 | 470.1615 |
| 177 | 3-tert-Butylphenol | 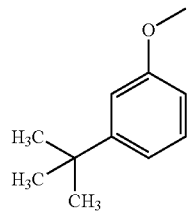 | 480.2295 |
| 178 | 2-Acetamidophenol | 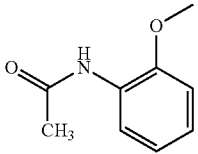 | 481.1928 |
| 179 | 3-Acetamidophenol | 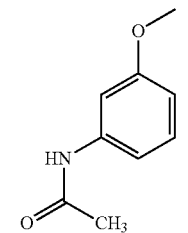 | 481.1924 |
126
-continued
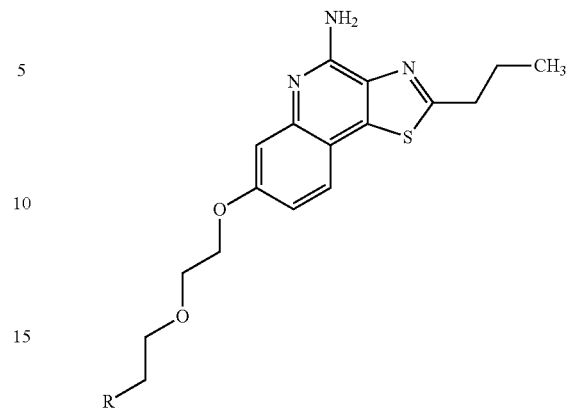
| Example | Reagent | R | Measured Mass (M + H) |
|---|---|---|---|
| 180 | 4-Acetamidophenol | 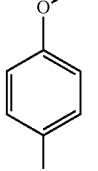 | 481.1940 |
| 181 | Methyl 3-hydroxybenzoate | 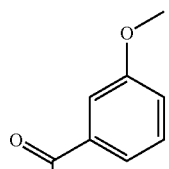 | 482.1783 |
| 182 | 2-Isopropoxyphenol | 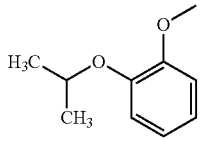 | 482.2131 |
| 183 | 2-Hydroxybenzotrifluoride | 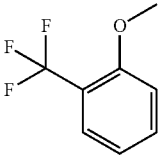 | 492.1588 |
| 184 | 3-Hydroxybenzotrifluoride | 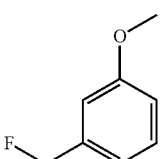 | 492.1577 |

-continued

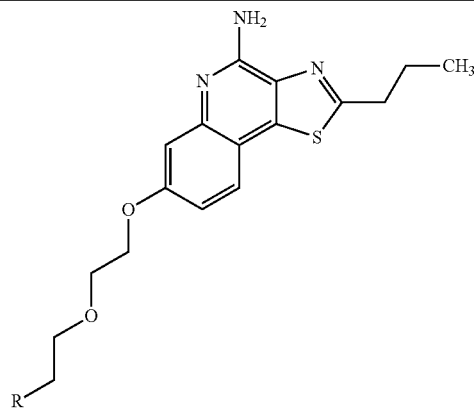

| Example | Reagent | R | Measured Mass (M + H) |
|---|---|---|---|
| 185 | 4-Hydroxybenzotrifluoride | 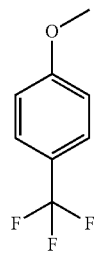 | 492.1598 |
| 186 | 2,3-Dichlorophenol | 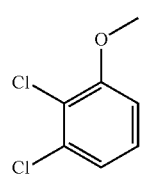 | 492.0910 |
| 187 | 2,4-Dichlorophenol | 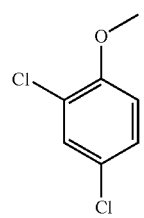 | 492.0929 |
| 188 | 2,5-Dichlorophenol | 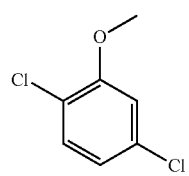 | 492.0930 |

-continued

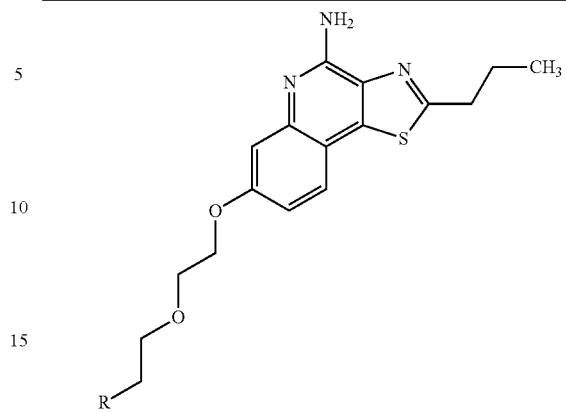

| Example | Reagent | R | Measured Mass (M + H) |
|---|---|---|---|
| 189 | 4-Hydroxybenzenesulfonamide | 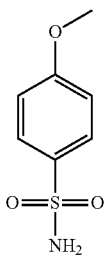 | 503.1436 |

Exemplary Compounds

Certain exemplary compounds, including some of those described above in the Examples, have the following Formula (IId) and the following 2, $R_{3d}$, and $R_2$, substituents, wherein each line of the table is matched with Formula IId to represent a specific embodiment of the invention.

IId

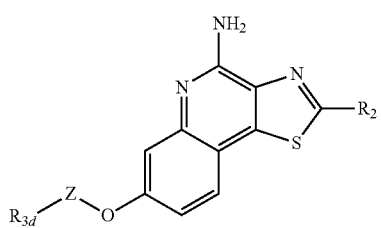

| Z | $R_{3d}$ | $R_2$ |
|---|---|---|
| —CH$_2$CH$_2$— | (methylsulfonyl)amino | ethyl |
| —CH$_2$CH$_2$— | (methylsulfonyl)amino | propyl |
| —CH$_2$CH$_2$— | (methylsulfonyl)amino | butyl |
| —CH$_2$CH$_2$— | (methylsulfonyl)amino | 2-methoxyethyl |
| —CH$_2$CH$_2$— | (methylsulfonyl)amino | ethoxymethyl |
| —CH$_2$CH$_2$— | pyrrolidin-1-yl | ethyl |
| —CH$_2$CH$_2$— | pyrrolidin-1-yl | propyl |
| —CH$_2$CH$_2$— | pyrrolidin-1-yl | butyl |
| —CH$_2$CH$_2$— | pyrrolidin-1-yl | 2-methoxyethyl |
| —CH$_2$CH$_2$— | pyrrolidin-1-yl | ethoxymethyl |

| Z | R$_{3d}$ | R$_2$ |
|---|---|---|
| —CH$_2$CH$_2$— | morpholin-4-yl | ethyl |
| —CH$_2$CH$_2$— | morpholin-4-yl | propyl |
| —CH$_2$CH$_2$— | morpholin-4-yl | butyl |
| —CH$_2$CH$_2$— | morpholin-4-yl | 2-methoxyethyl |
| —CH$_2$CH$_2$— | morpholin-4-yl | ethoxymethyl |
| —CH$_2$CH$_2$— | piperidin-1-yl | ethyl |
| —CH$_2$CH$_2$— | piperidin-1-yl | propyl |
| —CH$_2$CH$_2$— | piperidin-1-yl | butyl |
| —CH$_2$CH$_2$— | piperidin-1-yl | 2-methoxyethyl |
| —CH$_2$CH$_2$— | piperidin-1-yl | ethoxymethyl |
| —CH$_2$CH$_2$— | azepan-1-yl | ethyl |
| —CH$_2$CH$_2$— | azepan-1-yl | propyl |
| —CH$_2$CH$_2$— | azepan-1-yl | butyl |
| —CH$_2$CH$_2$— | azepan-1-yl | 2-methoxyethyl |
| —CH$_2$CH$_2$— | azepan-1-yl | ethoxymethyl |
| —CH$_2$CH$_2$— | 4-ethylpiperazin-1-yl | ethyl |
| —CH$_2$CH$_2$— | 4-ethylpiperazin-1-yl | propyl |
| —CH$_2$CH$_2$— | 4-ethylpiperazin-1-yl | butyl |
| —CH$_2$CH$_2$— | 4-ethylpiperazin-1-yl | 2-methoxyethyl |
| —CH$_2$CH$_2$— | 4-ethylpiperazin-1-yl | ethoxymethyl |
| —CH$_2$CH$_2$— | 4-acetylpiperazin-1-yl | ethyl |
| —CH$_2$CH$_2$— | 4-acetylpiperazin-1-yl | propyl |
| —CH$_2$CH$_2$— | 4-acetylpiperazin-1-yl | butyl |
| —CH$_2$CH$_2$— | 4-acetylpiperazin-1-yl | 2-methoxyethyl |
| —CH$_2$CH$_2$— | 4-acetylpiperazin-1-yl | ethoxymethyl |
| —CH$_2$CH$_2$— | 4-(2-hydroxyethyl)piperazin-1-yl | ethyl |
| —CH$_2$CH$_2$— | 4-(2-hydroxyethyl)piperazin-1-yl | propyl |
| —CH$_2$CH$_2$— | 4-(2-hydroxyethyl)piperazin-1-yl | butyl |
| —CH$_2$CH$_2$— | 4-(2-hydroxyethyl)piperazin-1-yl | 2-methoxyethyl |
| —CH$_2$CH$_2$— | 4-(2-hydroxyethyl)piperazin-1-yl | ethoxymethyl |
| —CH$_2$CH$_2$— | 3,4-dihydroisoquinolin-2(1H)-yl | ethyl |
| —CH$_2$CH$_2$— | 3,4-dihydroisoquinolin-2(1H)-yl | propyl |
| —CH$_2$CH$_2$— | 3,4-dihydroisoquinolin-2(1H)-yl | butyl |
| —CH$_2$CH$_2$— | 3,4-dihydroisoquinolin-2(1H)-yl | 2-methoxyethyl |
| —CH$_2$CH$_2$— | 3,4-dihydroisoquinolin-2(1H)-yl | ethoxymethyl |
| —CH$_2$CH$_2$— | 4-methyl-1,4-diazepan-1-yl | ethyl |
| —CH$_2$CH$_2$— | 4-methyl-1,4-diazepan-1-yl | propyl |
| —CH$_2$CH$_2$— | 4-methyl-1,4-diazepan-1-yl | butyl |
| —CH$_2$CH$_2$— | 4-methyl-1,4-diazepan-1-yl | 2-methoxyethyl |
| —CH$_2$CH$_2$— | 4-methyl-1,4-diazepan-1-yl | ethoxymethyl |
| —CH$_2$CH$_2$— | 4-pyrimidin-2-ylpiperazin-1-yl | ethyl |
| —CH$_2$CH$_2$— | 4-pyrimidin-2-ylpiperazin-1-yl | propyl |
| —CH$_2$CH$_2$— | 4-pyrimidin-2-ylpiperazin-1-yl | butyl |
| —CH$_2$CH$_2$— | 4-pyrimidin-2-ylpiperazin-1-yl | 2-methoxyethyl |
| —CH$_2$CH$_2$— | 4-pyrimidin-2-ylpiperazin-1-yl | ethoxymethyl |
| —CH$_2$CH$_2$CH$_2$— | (methylsulfonyl)amino | ethyl |
| —CH$_2$CH$_2$CH$_2$— | (methylsulfonyl)amino | propyl |
| —CH$_2$CH$_2$CH$_2$— | (methylsulfonyl)amino | butyl |
| —CH$_2$CH$_2$CH$_2$— | (methylsulfonyl)amino | 2-methoxyethyl |
| —CH$_2$CH$_2$CH$_2$— | (methylsulfonyl)amino | ethoxymethyl |
| —CH$_2$CH$_2$CH$_2$— | pyrrolidin-1-yl | ethyl |
| —CH$_2$CH$_2$CH$_2$— | pyrrolidin-1-yl | propyl |
| —CH$_2$CH$_2$CH$_2$— | pyrrolidin-1-yl | butyl |
| —CH$_2$CH$_2$CH$_2$— | pyrrolidin-1-yl | 2-methoxyethyl |
| —CH$_2$CH$_2$CH$_2$— | pyrrolidin-1-yl | ethoxymethyl |
| —CH$_2$CH$_2$CH$_2$— | morpholin-4-yl | ethyl |
| —CH$_2$CH$_2$CH$_2$— | morpholin-4-yl | propyl |
| —CH$_2$CH$_2$CH$_2$— | morpholin-4-yl | butyl |
| —CH$_2$CH$_2$CH$_2$— | morpholin-4-yl | 2-methoxyethyl |
| —CH$_2$CH$_2$CH$_2$— | morpholin-4-yl | ethoxymethyl |
| —CH$_2$CH$_2$CH$_2$— | piperidin-1-yl | ethyl |
| —CH$_2$CH$_2$CH$_2$— | piperidin-1-yl | propyl |
| —CH$_2$CH$_2$CH$_2$— | piperidin-1-yl | butyl |
| —CH$_2$CH$_2$CH$_2$— | piperidin-1-yl | 2-methoxyethyl |
| —CH$_2$CH$_2$CH$_2$— | piperidin-1-yl | ethoxymethyl |
| —CH$_2$CH$_2$CH$_2$— | azepan-1-yl | ethyl |
| —CH$_2$CH$_2$CH$_2$— | azepan-1-yl | propyl |
| —CH$_2$CH$_2$CH$_2$— | azepan-1-yl | butyl |
| —CH$_2$CH$_2$CH$_2$— | azepan-1-yl | 2-methoxyethyl |
| —CH$_2$CH$_2$CH$_2$— | azepan-1-yl | ethoxymethyl |
| —CH$_2$CH$_2$CH$_2$— | 4-ethylpiperazin-1-yl | ethyl |
| —CH$_2$CH$_2$CH$_2$— | 4-ethylpiperazin-1-yl | propyl |
| —CH$_2$CH$_2$CH$_2$— | 4-ethylpiperazin-1-yl | butyl |
| —CH$_2$CH$_2$CH$_2$— | 4-ethylpiperazin-1-yl | 2-methoxyethyl |
| —CH$_2$CH$_2$CH$_2$— | 4-ethylpiperazin-1-yl | ethoxymethyl |
| —CH$_2$CH$_2$CH$_2$— | 4-acetylpiperazin-1-yl | ethyl |
| —CH$_2$CH$_2$CH$_2$— | 4-acetylpiperazin-1-yl | propyl |

| Z | R₃d | R₂ |
|---|---|---|
| —CH₂CH₂CH₂— | 4-acetylpiperazin-1-yl | butyl |
| —CH₂CH₂CH₂— | 4-acetylpiperazin-1-yl | 2-methoxyethyl |
| —CH₂CH₂CH₂— | 4-acetylpiperazin-1-yl | ethoxymethyl |
| —CH₂CH₂CH₂— | 4-(2-hydroxyethyl)piperazin-1-yl | ethyl |
| —CH₂CH₂CH₂— | 4-(2-hydroxyethyl)piperazin-1-yl | propyl |
| —CH₂CH₂CH₂— | 4-(2-hydroxethyl)piperazin-1-yl | butyl |
| —CH₂CH₂CH₂— | 4-(2-hydroxyethyl)piperazin-1-yl | 2-methoxyethyl |
| —CH₂CH₂CH₂— | 4-(2-hydroxyethyl)piperazin-1-yl | ethoxymethyl |
| —CH₂CH₂CH₂— | 3,4-dihydroisoquinolin-2(1H)-yl | ethyl |
| —CH₂CH₂CH₂— | 3,4-dihydroisoquinolin-2(1H)-yl | propyl |
| —CH₂CH₂CH₂— | 3,4-dihydroisoquinolin-2(1H)-yl | butyl |
| —CH₂CH₂CH₂— | 3,4-dihydroisoquinolin-2(1H)-yl | 2-methoxyethyl |
| —CH₂CH₂CH₂— | 3,4-dihydroisoquinolin-2(1H)-yl | ethoxymethyl |
| —CH₂CH₂CH₂— | 4-methyl-1,4-diazepan-1-yl | ethyl |
| —CH₂CH₂CH₂— | 4-methyl-1,4-diazepan-1-yl | propyl |
| —CH₂CH₂CH₂— | 4-methyl-1,4-diazepan-1-yl | butyl |
| —CH₂CH₂CH₂— | 4-methyl-1,4-diazepan-1-yl | 2-methoxyethyl |
| —CH₂CH₂CH₂— | 4-methyl-1,4-diazepan-1-yl | ethoxymethyl |
| —CH₂CH₂CH₂— | 4-pyrimidin-2-ylpiperazin-1-yl | ethyl |
| —CH₂CH₂CH₂— | 4-pyrimidin-2-ylpiperazin-1-yl | propyl |
| —CH₂CH₂CH₂— | 4-pyrimidin-2-ylpiperazin-1-yl | butyl |
| —CH₂CH₂CH₂— | 4-pyrimidin-2-ylpiperazin-1-yl | 2-methoxyethyl |
| —CH₂CH₂CH₂— | 4-pyrimidin-2-ylpiperazin-1-yl | ethoxymethyl |
| —CH₂CH₂CH₂CH₂— | (methylsulfonyl)amino | ethyl |
| —CH₂CH₂CH₂CH₂— | (methylsulfonyl)amino | propyl |
| —CH₂CH₂CH₂CH₂— | (methylsulfonyl)amino | butyl |
| —CH₂CH₂CH₂CH₂— | (methylsulfonyl)amino | 2-methoxyethyl |
| —CH₂CH₂CH₂CH₂— | (methylsulfonyl)amino | ethoxymethyl |
| —CH₂CH₂CH₂CH₂— | pyrrolidin-1-yl | ethyl |
| —CH₂CH₂CH₂CH₂— | pyrrolidin-1-yl | propyl |
| —CH₂CH₂CH₂CH₂— | pyrrolidin-1-yl | butyl |
| —CH₂CH₂CH₂CH₂— | pyrrolidin-1-yl | 2-methoxyethyl |
| —CH₂CH₂CH₂CH₂— | pyrrolidin-1-yl | ethoxymethyl |
| —CH₂CH₂CH₂CH₂— | morpholin-4-yl | ethyl |
| —CH₂CH₂CH₂CH₂— | morpholin-4-yl | propyl |
| —CH₂CH₂CH₂CH₂— | morpholin-4-yl | butyl |
| —CH₂CH₂CH₂CH₂— | morpholin-4-yl | 2-methoxyethyl |
| —CH₂CH₂CH₂CH₂— | morpholin-4-yl | ethoxymethyl |
| —CH₂CH₂CH₂CH₂— | piperidin-1-yl | ethyl |
| —CH₂CH₂CH₂CH₂— | piperidin-1-yl | propyl |
| —CH₂CH₂CH₂CH₂— | piperidin-1-yl | butyl |
| —CH₂CH₂CH₂CH₂— | piperidin-1-yl | 2-methoxyethyl |
| —CH₂CH₂CH₂CH₂— | piperidin-1-yl | ethoxymethyl |
| —CH₂CH₂CH₂CH₂— | azepan-1-yl | ethyl |
| —CH₂CH₂CH₂CH₂— | azepan-1-yl | propyl |
| —CH₂CH₂CH₂CH₂— | azepan-1-yl | butyl |
| —CH₂CH₂CH₂CH₂— | azepan-1-yl | 2-methoxyethyl |
| —CH₂CH₂CH₂CH₂— | azepan-1-yl | ethoxymethyl |
| —CH₂CH₂CH₂CH₂— | 4-ethylpiperazin-1-yl | ethyl |
| —CH₂CH₂CH₂CH₂— | 4-ethylpiperazin-1-yl | propyl |
| —CH₂CH₂CH₂CH₂— | 4-ethylpiperazin-1-yl | butyl |
| —CH₂CH₂CH₂CH₂— | 4-ethylpiperazin-1-yl | 2-methoxyethyl |
| —CH₂CH₂CH₂CH₂— | 4-ethylpiperazin-1-yl | ethoxymethyl |
| —CH₂CH₂CH₂CH₂— | 4-acetylpiperazin-1-yl | ethyl |
| —CH₂CH₂CH₂CH₂— | 4-acetylpiperazin-1-yl | propyl |
| —CH₂CH₂CH₂CH₂— | 4-acetylpiperazin-1-yl | butyl |
| —CH₂CH₂CH₂CH₂— | 4-acetylpiperazin-1-yl | 2-methoxyethyl |
| —CH₂CH₂CH₂CH₂— | 4-acetylpiperazin-1-yl | ethoxymethyl |
| —CH₂CH₂CH₂CH₂— | 4-(2-hydroxyethyl)piperazin-1-yl | ethyl |
| —CH₂CH₂CH₂CH₂— | 4-(2-hydroxyethyl)piperazin-1-yl | propyl |
| —CH₂CH₂CH₂CH₂— | 4-(2-hydroxethyl)piperazin-1-yl | butyl |
| —CH₂CH₂CH₂CH₂— | 4-(2-hydroxyethyl)piperazin-1-yl | 2-methoxyethyl |
| —CH₂CH₂CH₂CH₂— | 4-(2-hydroxyethyl)piperazin-1-yl | ethoxymethyl |
| —CH₂CH₂CH₂CH₂— | 3,4-dihydroisoquinolin-2(1H)-yl | ethyl |
| —CH₂CH₂CH₂CH₂— | 3,4-dihydroisoquinolin-2(1H)-yl | propyl |
| —CH₂CH₂CH₂CH₂— | 3,4-dihydroisoquinolin-2(1H)-yl | butyl |
| —CH₂CH₂CH₂CH₂— | 3,4-dihydroisoquinolin-2(1H)-yl | 2-methoxyethyl |
| —CH₂CH₂CH₂CH₂— | 3,4-dihydroisoquinolin-2(1H)-yl | ethoxymethyl |
| —CH₂CH₂CH₂CH₂— | 4-methyl-1,4-diazepan-1-yl | ethyl |
| —CH₂CH₂CH₂CH₂— | 4-methyl-1,4-diazepan-1-yl | propyl |
| —CH₂CH₂CH₂CH₂— | 4-methyl-1,4-diazepan-1-yl | butyl |
| —CH₂CH₂CH₂CH₂— | 4-methyl-1,4-diazepan-1-yl | 2-methoxyethyl |
| —CH₂CH₂CH₂CH₂— | 4-methyl-1,4-diazepan-1-yl | ethoxymethyl |
| —CH₂CH₂CH₂CH₂— | 4-pyrimidin-2-ylpiperazin-1-yl | ethyl |
| —CH₂CH₂CH₂CH₂— | 4-pyrimidin-2-ylpiperazin-1-yl | propyl |
| —CH₂CH₂CH₂CH₂— | 4-pyrimidin-2-ylpiperazin-1-yl | butyl |
| —CH₂CH₂CH₂CH₂— | 4-pyrimidin-2-ylpiperazin-1-yl | 2-methoxyethyl |

-continued

| Z | R$_{3d}$ | R$_2$ |
|---|---|---|
| —CH$_2$CH$_2$CH$_2$CH$_2$— | 4-pyrimidin-2-ylpiperazin-1-yl | ethoxymethyl |
| —CH$_2$CH$_2$CH$_2$CH$_2$CH$_2$— | (methylsulfonyl)amino | ethyl |
| —CH$_2$CH$_2$CH$_2$CH$_2$CH$_2$— | (methylsulfonyl)amino | propyl |
| —CH$_2$CH$_2$CH$_2$CH$_2$CH$_2$— | (methylsulfonyl)amino | butyl |
| —CH$_2$CH$_2$CH$_2$CH$_2$CH$_2$— | (methylsulfonyl)amino | 2-methoxyethyl |
| —CH$_2$CH$_2$CH$_2$CH$_2$CH$_2$— | (methylsulfonyl)amino | ethoxymethyl |
| —CH$_2$CH$_2$CH$_2$CH$_2$CH$_2$— | pyrrolidin-1-yl | ethyl |
| —CH$_2$CH$_2$CH$_2$CH$_2$CH$_2$— | pyrrolidin-1-yl | propyl |
| —CH$_2$CH$_2$CH$_2$CH$_2$CH$_2$— | pyrrolidin-1-yl | butyl |
| —CH$_2$CH$_2$CH$_2$CH$_2$CH$_2$— | pyrrolidin-1-yl | 2-methoxyethyl |
| —CH$_2$CH$_2$CH$_2$CH$_2$CH$_2$— | pyrrolidin-1-yl | ethoxymethyl |
| —CH$_2$CH$_2$CH$_2$CH$_2$CH$_2$— | morpholin-4-yl | ethyl |
| —CH$_2$CH$_2$CH$_2$CH$_2$CH$_2$— | morpholin-4-yl | propyl |
| —CH$_2$CH$_2$CH$_2$CH$_2$CH$_2$— | morpholin-4-yl | butyl |
| —CH$_2$CH$_2$CH$_2$CH$_2$CH$_2$— | morpholin-4-yl | 2-methoxyethyl |
| —CH$_2$CH$_2$CH$_2$CH$_2$CH$_2$— | morpholin-4-yl | ethoxymethyl |
| —CH$_2$CH$_2$CH$_2$CH$_2$CH$_2$— | piperidin-1-yl | ethyl |
| —CH$_2$CH$_2$CH$_2$CH$_2$CH$_2$— | piperidin-1-yl | propyl |
| —CH$_2$CH$_2$CH$_2$CH$_2$CH$_2$— | piperidin-1-yl | butyl |
| —CH$_2$CH$_2$CH$_2$CH$_2$CH$_2$— | piperidin-1-yl | 2-methoxyethyl |
| —CH$_2$CH$_2$CH$_2$CH$_2$CH$_2$— | piperidin-1-yl | ethoxymethyl |
| —CH$_2$CH$_2$CH$_2$CH$_2$CH$_2$— | azepan-1-yl | ethyl |
| —CH$_2$CH$_2$CH$_2$CH$_2$CH$_2$— | azepan-1-yl | propyl |
| —CH$_2$CH$_2$CH$_2$CH$_2$CH$_2$— | azepan-1-yl | butyl |
| —CH$_2$CH$_2$CH$_2$CH$_2$CH$_2$— | azepan-1-yl | 2-methoxyethyl |
| —CH$_2$CH$_2$CH$_2$CH$_2$CH$_2$— | azepan-1-yl | ethoxymethyl |
| —CH$_2$CH$_2$CH$_2$CH$_2$CH$_2$— | 4-ethylpiperazin-1-yl | ethyl |
| —CH$_2$CH$_2$CH$_2$CH$_2$CH$_2$— | 4-ethylpiperazin-1-yl | propyl |
| —CH$_2$CH$_2$CH$_2$CH$_2$CH$_2$— | 4-ethylpiperazin-1-yl | butyl |
| —CH$_2$CH$_2$CH$_2$CH$_2$CH$_2$— | 4-ethylpiperazin-1-yl | 2-methoxyethyl |
| —CH$_2$CH$_2$CH$_2$CH$_2$CH$_2$— | 4-ethylpiperazin-1-yl | ethoxymethyl |
| —CH$_2$CH$_2$CH$_2$CH$_2$CH$_2$— | 4-acetylpiperazin-1-yl | ethyl |
| —CH$_2$CH$_2$CH$_2$CH$_2$CH$_2$— | 4-acetylpiperazin-1-yl | propyl |
| —CH$_2$CH$_2$CH$_2$CH$_2$CH$_2$— | 4-acetylpiperazin-1-yl | butyl |
| —CH$_2$CH$_2$CH$_2$CH$_2$CH$_2$— | 4-acetylpiperazin-1-yl | 2-methoxyethyl |
| —CH$_2$CH$_2$CH$_2$CH$_2$CH$_2$— | 4-acetylpiperazin-1-yl | ethoxymethyl |
| —CH$_2$CH$_2$CH$_2$CH$_2$CH$_2$— | 4-(2-hydroxyethyl)piperazin-1-yl | ethyl |
| —CH$_2$CH$_2$CH$_2$CH$_2$CH$_2$— | 4-(2-hydroxyethyl)piperazin-1-yl | propyl |
| —CH$_2$CH$_2$CH$_2$CH$_2$CH$_2$— | 4-(2-hydroxethyl)piperazin-1-yl | butyl |
| —CH$_2$CH$_2$CH$_2$CH$_2$CH$_2$— | 4-(2-hydroxyethyl)piperazin-1-yl | 2-methoxyethyl |
| —CH$_2$CH$_2$CH$_2$CH$_2$CH$_2$— | 4-(2-hydroxyethyl)piperazin-1-yl | ethoxymethyl |
| —CH$_2$CH$_2$CH$_2$CH$_2$CH$_2$— | 3,4-dihydroisoquinolin-2(1H)-yl | ethyl |
| —CH$_2$CH$_2$CH$_2$CH$_2$CH$_2$— | 3,4-dihydroisoquinolin-2(1H)-yl | propyl |
| —CH$_2$CH$_2$CH$_2$CH$_2$CH$_2$— | 3,4-dihydroisoquinolin-2(1H)-yl | butyl |
| —CH$_2$CH$_2$CH$_2$CH$_2$CH$_2$— | 3,4-dihydroisoquinolin-2(1H)-yl | 2-methoxyethyl |
| —CH$_2$CH$_2$CH$_2$CH$_2$CH$_2$— | 3,4-dihydroisoquinolin-2(1H)-yl | ethoxymethyl |
| —CH$_2$CH$_2$CH$_2$CH$_2$CH$_2$— | 4-methyl-1,4-diazepan-1-yl | ethyl |
| —CH$_2$CH$_2$CH$_2$CH$_2$CH$_2$— | 4-methyl-1,4-diazepan-1-yl | propyl |
| —CH$_2$CH$_2$CH$_2$CH$_2$CH$_2$— | 4-methyl-1,4-diazepan-1-yl | butyl |
| —CH$_2$CH$_2$CH$_2$CH$_2$CH$_2$— | 4-methyl-1,4-diazepan-1-yl | 2-methoxyethyl |
| —CH$_2$CH$_2$CH$_2$CH$_2$CH$_2$— | 4-methyl-1,4-diazepan-1-yl | ethoxymethyl |
| —CH$_2$CH$_2$CH$_2$CH$_2$CH$_2$— | 4-pyrimidin-2-ylpiperazin-1-yl | ethyl |
| —CH$_2$CH$_2$CH$_2$CH$_2$CH$_2$— | 4-pyrimidin-2-ylpiperazin-1-yl | propyl |
| —CH$_2$CH$_2$CH$_2$CH$_2$CH$_2$— | 4-pyrimidin-2-ylpiperazin-1-yl | butyl |
| —CH$_2$CH$_2$CH$_2$CH$_2$CH$_2$— | 4-pyrimidin-2-ylpiperazin-1-yl | 2-methoxyethyl |
| —CH$_2$CH$_2$CH$_2$CH$_2$CH$_2$— | 4-pyrimidin-2-ylpiperazin-1-yl | ethoxymethyl |
| —CH$_2$CH$_2$CH$_2$CH$_2$CH$_2$CH$_2$— | (methylsulfonyl)amino | ethyl |
| —CH$_2$CH$_2$CH$_2$CH$_2$CH$_2$CH$_2$— | (methylsulfonyl)amino | propyl |
| —CH$_2$CH$_2$CH$_2$CH$_2$CH$_2$CH$_2$— | (methylsulfonyl)amino | butyl |
| —CH$_2$CH$_2$CH$_2$CH$_2$CH$_2$CH$_2$— | (methylsulfonyl)amino | 2-methoxyethyl |
| —CH$_2$CH$_2$CH$_2$CH$_2$CH$_2$CH$_2$— | (methylsulfonyl)amino | ethoxymethyl |
| —CH$_2$CH$_2$CH$_2$CH$_2$CH$_2$CH$_2$— | pyrrolidin-1-yl | ethyl |
| —CH$_2$CH$_2$CH$_2$CH$_2$CH$_2$CH$_2$— | pyrrolidin-1-yl | propyl |
| —CH$_2$CH$_2$CH$_2$CH$_2$CH$_2$CH$_2$— | pyrrolidin-1-yl | butyl |
| —CH$_2$CH$_2$CH$_2$CH$_2$CH$_2$CH$_2$— | pyrrolidin-1-yl | 2-methoxyethyl |
| —CH$_2$CH$_2$CH$_2$CH$_2$CH$_2$CH$_2$— | pyrrolidin-1-yl | ethoxymethyl |
| —CH$_2$CH$_2$CH$_2$CH$_2$CH$_2$CH$_2$— | morpholin-4-yl | ethyl |
| —CH$_2$CH$_2$CH$_2$CH$_2$CH$_2$CH$_2$— | morpholin-4-yl | propyl |
| —CH$_2$CH$_2$CH$_2$CH$_2$CH$_2$CH$_2$— | morpholin-4-yl | butyl |
| —CH$_2$CH$_2$CH$_2$CH$_2$CH$_2$CH$_2$— | morpholin-4-yl | 2-methoxyethyl |
| —CH$_2$CH$_2$CH$_2$CH$_2$CH$_2$CH$_2$— | morpholin-4-yl | ethoxymethyl |
| —CH$_2$CH$_2$CH$_2$CH$_2$CH$_2$CH$_2$— | piperidin-1-yl | ethyl |
| —CH$_2$CH$_2$CH$_2$CH$_2$CH$_2$CH$_2$— | piperidin-1-yl | propyl |
| —CH$_2$CH$_2$CH$_2$CH$_2$CH$_2$CH$_2$— | piperidin-1-yl | butyl |
| —CH$_2$CH$_2$CH$_2$CH$_2$CH$_2$CH$_2$— | piperidin-1-yl | 2-methoxyethyl |
| —CH$_2$CH$_2$CH$_2$CH$_2$CH$_2$CH$_2$— | piperidin-1-yl | ethoxymethyl |
| —CH$_2$CH$_2$CH$_2$CH$_2$CH$_2$CH$_2$— | azepan-1-yl | ethyl |

| Z | R$_{3d}$ | R$_2$ |
|---|---|---|
| —CH$_2$CH$_2$CH$_2$CH$_2$CH$_2$CH$_2$— | azepan-1-yl | propyl |
| —CH$_2$CH$_2$CH$_2$CH$_2$CH$_2$CH$_2$— | azepan-1-yl | butyl |
| —CH$_2$CH$_2$CH$_2$CH$_2$CH$_2$CH$_2$— | azepan-1-yl | 2-methoxyethyl |
| —CH$_2$CH$_2$CH$_2$CH$_2$CH$_2$CH$_2$— | azepan-1-yl | ethoxymethyl |
| —CH$_2$CH$_2$CH$_2$CH$_2$CH$_2$CH$_2$— | 4-ethylpiperazin-1-yl | ethyl |
| —CH$_2$CH$_2$CH$_2$CH$_2$CH$_2$CH$_2$— | 4-ethylpiperazin-1-yl | propyl |
| —CH$_2$CH$_2$CH$_2$CH$_2$CH$_2$CH$_2$— | 4-ethylpiperazin-1-yl | butyl |
| —CH$_2$CH$_2$CH$_2$CH$_2$CH$_2$CH$_2$— | 4-ethylpiperazin-1-yl | 2-methoxyethyl |
| —CH$_2$CH$_2$CH$_2$CH$_2$CH$_2$CH$_2$— | 4-ethylpiperazin-1-yl | ethoxymethyl |
| —CH$_2$CH$_2$CH$_2$CH$_2$CH$_2$CH$_2$— | 4-acetylpiperazin-1-yl | ethyl |
| —CH$_2$CH$_2$CH$_2$CH$_2$CH$_2$CH$_2$— | 4-acetylpiperazin-1-yl | propyl |
| —CH$_2$CH$_2$CH$_2$CH$_2$CH$_2$CH$_2$— | 4-acetylpiperazin-1-yl | butyl |
| —CH$_2$CH$_2$CH$_2$CH$_2$CH$_2$CH$_2$— | 4-acetylpiperazin-1-yl | 2-methoxyethyl |
| —CH$_2$CH$_2$CH$_2$CH$_2$CH$_2$CH$_2$— | 4-acetylpiperazin-1-yl | ethoxymethyl |
| —CH$_2$CH$_2$CH$_2$CH$_2$CH$_2$CH$_2$— | 4-(2-hydroxyethyl)piperazin-1-yl | ethyl |
| —CH$_2$CH$_2$CH$_2$CH$_2$CH$_2$CH$_2$— | 4-(2-hydroxyethyl)piperazin-1-yl | propyl |
| —CH$_2$CH$_2$CH$_2$CH$_2$CH$_2$CH$_2$— | 4-(2-hydroxethyl)piperazin-1-yl | butyl |
| —CH$_2$CH$_2$CH$_2$CH$_2$CH$_2$CH$_2$— | 4-(2-hydroxyethyl)piperazin-1-yl | 2-methoxyethyl |
| —CH$_2$CH$_2$CH$_2$CH$_2$CH$_2$CH$_2$— | 4-(2-hydroxyethyl)piperazin-1-yl | ethoxymethyl |
| —CH$_2$CH$_2$CH$_2$CH$_2$CH$_2$CH$_2$— | 3,4-dihydroisoquinolin-2(1H)-yl | ethyl |
| —CH$_2$CH$_2$CH$_2$CH$_2$CH$_2$CH$_2$— | 3,4-dihydroisoquinolin-2(1H)-yl | propyl |
| —CH$_2$CH$_2$CH$_2$CH$_2$CH$_2$CH$_2$— | 3,4-dihydroisoquinolin-2(1H)-yl | butyl |
| —CH$_2$CH$_2$CH$_2$CH$_2$CH$_2$CH$_2$— | 3,4-dihydroisoquinolin-2(1H)-yl | 2-methoxyethyl |
| —CH$_2$CH$_2$CH$_2$CH$_2$CH$_2$CH$_2$— | 3,4-dihydroisoquinolin-2(1H)-yl | ethoxymethyl |
| —CH$_2$CH$_2$CH$_2$CH$_2$CH$_2$CH$_2$— | 4-methyl-1,4-diazepan-1-yl | ethyl |
| —CH$_2$CH$_2$CH$_2$CH$_2$CH$_2$CH$_2$— | 4-methyl-1,4-diazepan-1-yl | propyl |
| —CH$_2$CH$_2$CH$_2$CH$_2$CH$_2$CH$_2$— | 4-methyl-1,4-diazepan-1-yl | butyl |
| —CH$_2$CH$_2$CH$_2$CH$_2$CH$_2$CH$_2$— | 4-methyl-1,4-diazepan-1-yl | 2-methoxyethyl |
| —CH$_2$CH$_2$CH$_2$CH$_2$CH$_2$CH$_2$— | 4-methyl-1,4-diazepan-1-yl | ethoxymethyl |
| —CH$_2$CH$_2$CH$_2$CH$_2$CH$_2$CH$_2$— | 4-pyrimidin-2-ylpiperazin-1-yl | ethyl |
| —CH$_2$CH$_2$CH$_2$CH$_2$CH$_2$CH$_2$— | 4-pyrimidin-2-ylpiperazin-1-yl | propyl |
| —CH$_2$CH$_2$CH$_2$CH$_2$CH$_2$CH$_2$— | 4-pyrimidin-2-ylpiperazin-1-yl | butyl |
| —CH$_2$CH$_2$CH$_2$CH$_2$CH$_2$CH$_2$— | 4-pyrimidin-2-ylpiperazin-1-yl | 2-methoxyethyl |
| —CH$_2$CH$_2$CH$_2$CH$_2$CH$_2$CH$_2$— | 4-pyrimidin-2-ylpiperazin-1-yl | ethoxymethyl |
| —CH$_2$CH$_2$OCH$_2$CH$_2$— | (methylsulfonyl)amino | ethyl |
| —CH$_2$CH$_2$OCH$_2$CH$_2$— | (methylsulfonyl)amino | propyl |
| —CH$_2$CH$_2$OCH$_2$CH$_2$— | (methylsulfonyl)amino | butyl |
| —CH$_2$CH$_2$OCH$_2$CH$_2$— | (methylsulfonyl)amino | 2-methoxyethyl |
| —CH$_2$CH$_2$OCH$_2$CH$_2$— | (methylsulfonyl)amino | ethoxymethyl |
| —CH$_2$CH$_2$OCH$_2$CH$_2$— | pyrrolidin-1-yl | ethyl |
| —CH$_2$CH$_2$OCH$_2$CH$_2$— | pyrrolidin-1-yl | propyl |
| —CH$_2$CH$_2$OCH$_2$CH$_2$— | pyrrolidin-1-yl | butyl |
| —CH$_2$CH$_2$OCH$_2$CH$_2$— | pyrrolidin-1-yl | 2-methoxyethyl |
| —CH$_2$CH$_2$OCH$_2$CH$_2$— | pyrrolidin-1-yl | ethoxymethyl |
| —CH$_2$CH$_2$OCH$_2$CH$_2$— | morpholin-4-yl | ethyl |
| —CH$_2$CH$_2$OCH$_2$CH$_2$— | morpholin-4-yl | propyl |
| —CH$_2$CH$_2$OCH$_2$CH$_2$— | morpholin-4-yl | butyl |
| —CH$_2$CH$_2$OCH$_2$CH$_2$— | morpholin-4-yl | 2-methoxyethyl |
| —CH$_2$CH$_2$OCH$_2$CH$_2$— | morpholin-4-yl | ethoxymethyl |
| —CH$_2$CH$_2$OCH$_2$CH$_2$— | piperidin-1-yl | ethyl |
| —CH$_2$CH$_2$OCH$_2$CH$_2$— | piperidin-1-yl | propyl |
| —CH$_2$CH$_2$OCH$_2$CH$_2$— | piperidin-1-yl | butyl |
| —CH$_2$CH$_2$OCH$_2$CH$_2$— | piperidin-1-yl | 2-methoxyethyl |
| —CH$_2$CH$_2$OCH$_2$CH$_2$— | piperidin-1-yl | ethoxymethyl |
| —CH$_2$CH$_2$OCH$_2$CH$_2$— | azepan-1-yl | ethyl |
| —CH$_2$CH$_2$OCH$_2$CH$_2$— | azepan-1-yl | propyl |
| —CH$_2$CH$_2$OCH$_2$CH$_2$— | azepan-1-yl | butyl |
| —CH$_2$CH$_2$OCH$_2$CH$_2$— | azepan-1-yl | 2-methoxyethyl |
| —CH$_2$CH$_2$OCH$_2$CH$_2$— | azepan-1-yl | ethoxymethyl |
| —CH$_2$CH$_2$OCH$_2$CH$_2$— | 4-ethylpiperazin-1-yl | ethyl |
| —CH$_2$CH$_2$OCH$_2$CH$_2$— | 4-ethylpiperazin-1-yl | propyl |
| —CH$_2$CH$_2$OCH$_2$CH$_2$— | 4-ethylpiperazin-1-yl | butyl |
| —CH$_2$CH$_2$OCH$_2$CH$_2$— | 4-ethylpiperazin-1-yl | 2-methoxyethyl |
| —CH$_2$CH$_2$OCH$_2$CH$_2$— | 4-ethylpiperazin-1-yl | ethoxymethyl |
| —CH$_2$CH$_2$OCH$_2$CH$_2$— | 4-acetylpiperazin-1-yl | ethyl |
| —CH$_2$CH$_2$OCH$_2$CH$_2$— | 4-acetylpiperazin-1-yl | propyl |
| —CH$_2$CH$_2$OCH$_2$CH$_2$— | 4-acetylpiperazin-1-yl | butyl |
| —CH$_2$CH$_2$OCH$_2$CH$_2$— | 4-acetylpiperazin-1-yl | 2-methoxyethyl |
| —CH$_2$CH$_2$OCH$_2$CH$_2$— | 4-acetylpiperazin-1-yl | ethoxymethyl |
| —CH$_2$CH$_2$OCH$_2$CH$_2$— | 4-(2-hydroxyethyl)piperazin-1-yl | ethyl |
| —CH$_2$CH$_2$OCH$_2$CH$_2$— | 4-(2-hydroxyethyl)piperazin-1-yl | propyl |
| —CH$_2$CH$_2$OCH$_2$CH$_2$— | 4-(2-hydroxethyl)piperazin-1-yl | butyl |
| —CH$_2$CH$_2$OCH$_2$CH$_2$— | 4-(2-hydroxyethyl)piperazin-1-yl | 2-methoxyethyl |
| —CH$_2$CH$_2$OCH$_2$CH$_2$— | 4-(2-hydroxyethyl)piperazin-1-yl | ethoxymethyl |
| —CH$_2$CH$_2$OCH$_2$CH$_2$— | 3,4-dihydroisoquinolin-2(1H)-yl | ethyl |
| —CH$_2$CH$_2$OCH$_2$CH$_2$— | 3,4-dihydroisoquinolin-2(1H)-yl | propyl |
| —CH$_2$CH$_2$OCH$_2$CH$_2$— | 3,4-dihydroisoquinolin-2(1H)-yl | butyl |

| Z | R$_{3d}$ | R$_2$ |
|---|---|---|
| —CH$_2$CH$_2$OCH$_2$CH$_2$— | 3,4-dihydroisoquinolin-2(1H)-yl | 2-methoxyethyl |
| —CH$_2$CH$_2$OCH$_2$CH$_2$— | 3,4-dihydroisoquinolin-2(1H)-yl | ethoxymethyl |
| —CH$_2$CH$_2$OCH$_2$CH$_2$— | 4-methyl-1,4-diazepan-1-yl | ethyl |
| —CH$_2$CH$_2$OCH$_2$CH$_2$— | 4-methyl-1,4-diazepan-1-yl | propyl |
| —CH$_2$CH$_2$OCH$_2$CH$_2$— | 4-methyl-1,4-diazepan-1-yl | butyl |
| —CH$_2$CH$_2$OCH$_2$CH$_2$— | 4-methyl-1,4-diazepan-1-yl | 2-methoxyethyl |
| —CH$_2$CH$_2$OCH$_2$CH$_2$— | 4-methyl-1,4-diazepan-1-yl | ethoxymethyl |
| —CH$_2$CH$_2$OCH$_2$CH$_2$— | 4-pyrimidin-2-ylpiperazin-1-yl | ethyl |
| —CH$_2$CH$_2$OCH$_2$CH$_2$— | 4-pyrimidin-2-ylpiperazin-1-yl | propyl |
| —CH$_2$CH$_2$OCH$_2$CH$_2$— | 4-pyrimidin-2-ylpiperazin-1-yl | butyl |
| —CH$_2$CH$_2$OCH$_2$CH$_2$— | 4-pyrimidin-2-ylpiperazin-1-yl | 2-methoxyethyl |
| —CH$_2$CH$_2$OCH$_2$CH$_2$— | 4-pyrimidin-2-ylpiperazin-1-yl | ethoxymethyl |

Certain exemplary compounds, including some of those described above in the Examples, have the following Formula (IIe) and the following Z, R$_{3e}$, and R$_2$, substituents, wherein each line of the table is matched with Formula IIe to represent a specific embodiment of the invention.

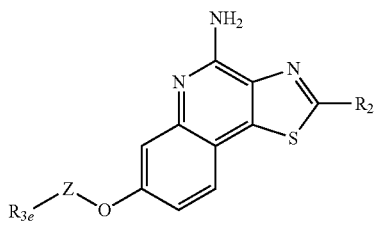

IIe

| Z | R$_{3e}$ | R$_2$ |
|---|---|---|
| —CH$_2$CH$_2$— | (phenylaminocarbonyl)amino | ethyl |
| —CH$_2$CH$_2$— | (phenylaminocarbonyl)amino | propyl |
| —CH$_2$CH$_2$— | (phenylaminocarbonyl)amino | butyl |
| —CH$_2$CH$_2$— | (phenylaminocarbonyl)amino | 2-methoxyethyl |
| —CH$_2$CH$_2$— | (phenylaminocarbonyl)amino | ethoxymethyl |
| —CH$_2$CH$_2$— | (phenylaminocarbonothioyl)amino | ethyl |
| —CH$_2$CH$_2$— | (phenylaminocarbonothioyl)amino | propyl |
| —CH$_2$CH$_2$— | (phenylaminocarbonothioyl)amino | butyl |
| —CH$_2$CH$_2$— | (phenylaminocarbonothioyl)amino | 2-methoxyethyl |
| —CH$_2$CH$_2$— | (phenylaminocarbonothioyl)amino | ethoxymethyl |
| —CH$_2$CH$_2$— | {[(3-methoxyphenyl)amino]-carbonyl}amino | ethyl |
| —CH$_2$CH$_2$— | {[(3-methoxyphenyl)amino]-carbonyl}amino | propyl |
| —CH$_2$CH$_2$— | {[(3-methoxyphenyl)amino]-carbonyl}amino | butyl |
| —CH$_2$CH$_2$— | {[(3-methoxyphenyl)amino]-carbonyl}amino | 2-methoxyethyl |
| —CH$_2$CH$_2$— | {[(3-methoxyphenyl)amino]-carbonyl}amino | ethoxymethyl |
| —CH$_2$CH$_2$— | methyl(1-methylpiperdin-4-yl)amino | ethyl |
| —CH$_2$CH$_2$— | methyl(1-methylpiperdin-4-yl)amino | propyl |
| —CH$_2$CH$_2$— | methyl(1-methylpiperdin-4-yl)amino | butyl |
| —CH$_2$CH$_2$— | methyl(1-methylpiperdin-4-yl)amino | 2-methoxyethyl |
| —CH$_2$CH$_2$— | methyl(1-methylpiperdin-4-yl)amino | ethoxymethyl |
| —CH$_2$CH$_2$— | 4-pyrrolidin-1-ylpiperidin-1-yl | ethyl |
| —CH$_2$CH$_2$— | 4-pyrrolidin-1-ylpiperidin-1-yl | propyl |
| —CH$_2$CH$_2$— | 4-pyrrolidin-1-ylpiperidin-1-yl | butyl |
| —CH$_2$CH$_2$— | 4-pyrrolidin-1-ylpiperidin-1-yl | 2-methoxyethyl |
| —CH$_2$CH$_2$— | 4-pyrrolidin-1-ylpiperidin-1-yl | ethoxymethyl |
| —CH$_2$CH$_2$— | 1,4'-bipiperidin-1'-yl | ethyl |

-continued

| Z | R$_{3e}$ | R$_2$ |
|---|---|---|
| —CH$_2$CH$_2$— | 1,4'-bipiperidin-1'-yl | propyl |
| —CH$_2$CH$_2$— | 1,4'-bipiperidin-1'-yl | butyl |
| —CH$_2$CH$_2$— | 1,4'-bipiperidin-1'-yl | 2-methoxyethyl |
| —CH$_2$CH$_2$— | 1,4'-bipiperidin-1'-yl | ethoxymethyl |
| —CH$_2$CH$_2$CH$_2$— | (phenylaminocarbonyl)amino | ethyl |
| —CH$_2$CH$_2$CH$_2$— | (phenylaminocarbonyl)amino | propyl |
| —CH$_2$CH$_2$CH$_2$— | (phenylaminocarbonyl)amino | butyl |
| —CH$_2$CH$_2$CH$_2$— | (phenylaminocarbonyl)amino | 2-methoxyethyl |
| —CH$_2$CH$_2$CH$_2$— | (phenylaminocarbonyl)amino | ethoxymethyl |
| —CH$_2$CH$_2$CH$_2$— | (phenylaminocarbonothioyl)amino | ethyl |
| —CH$_2$CH$_2$CH$_2$— | (phenylaminocarbonothioyl)amino | propyl |
| —CH$_2$CH$_2$CH$_2$— | (phenylaminocarbonothioyl)amino | butyl |
| —CH$_2$CH$_2$CH$_2$— | (phenylaminocarbonothioyl)amino | 2-methoxyethyl |
| —CH$_2$CH$_2$CH$_2$— | (phenylaminocarbonothioyl)amino | ethoxymethyl |
| —CH$_2$CH$_2$CH$_2$— | {[(3-methoxyphenyl)amino]-carbonyl}amino | ethyl |
| —CH$_2$CH$_2$CH$_2$— | {[(3-methoxyphenyl)amino]-carbonyl}amino | propyl |
| —CH$_2$CH$_2$CH$_2$— | {[(3-methoxyphenyl)amino]-carbonyl}amino | butyl |
| —CH$_2$CH$_2$CH$_2$— | {[(3-methoxyphenyl)amino]-carbonyl}amino | 2-methoxyethyl |
| —CH$_2$CH$_2$CH$_2$— | {[(3-methoxyphenyl)amino]-carbonyl}amino | ethoxymethyl |
| —CH$_2$CH$_2$CH$_2$— | methyl(1-methylpiperdin-4-yl)amino | ethyl |
| —CH$_2$CH$_2$CH$_2$— | methyl(1-methylpiperdin-4-yl)amino | propyl |
| —CH$_2$CH$_2$CH$_2$— | methyl(1-methylpiperdin-4-yl)amino | butyl |
| —CH$_2$CH$_2$CH$_2$— | methyl(1-methylpiperdin-4-yl)amino | 2-methoxyethyl |
| —CH$_2$CH$_2$CH$_2$— | methyl(1-methylpiperdin-4-yl)amino | ethoxymethyl |
| —CH$_2$CH$_2$CH$_2$— | 4-pyrrolidin-1-ylpiperidin-1-yl | ethyl |
| —CH$_2$CH$_2$CH$_2$— | 4-pyrrolidin-1-ylpiperidin-1-yl | propyl |
| —CH$_2$CH$_2$CH$_2$— | 4-pyrrolidin-1-ylpiperidin-1-yl | butyl |
| —CH$_2$CH$_2$CH$_2$— | 4-pyrrolidin-1-ylpiperidin-1-yl | 2-methoxyethyl |
| —CH$_2$CH$_2$CH$_2$— | 4-pyrrolidin-1-ylpiperidin-1-yl | ethoxymethyl |
| —CH$_2$CH$_2$CH$_2$— | 1,4'-bipiperidin-1'-yl | ethyl |
| —CH$_2$CH$_2$CH$_2$— | 1,4'-bipiperidin-1'-yl | propyl |
| —CH$_2$CH$_2$CH$_2$— | 1,4'-bipiperidin-1'-yl | butyl |
| —CH$_2$CH$_2$CH$_2$— | 1,4'-bipiperidin-1'-yl | 2-methoxyethyl |
| —CH$_2$CH$_2$CH$_2$— | 1,4'-bipiperidin-1'-yl | ethoxymethyl |
| —CH$_2$CH$_2$CH$_2$CH$_2$— | (phenylaminocarbonyl)amino | ethyl |
| —CH$_2$CH$_2$CH$_2$CH$_2$— | (phenylaminocarbonyl)amino | propyl |
| —CH$_2$CH$_2$CH$_2$CH$_2$— | (phenylaminocarbonyl)amino | butyl |
| —CH$_2$CH$_2$CH$_2$CH$_2$— | (phenylaminocarbonyl)amino | 2-methoxyethyl |
| —CH$_2$CH$_2$CH$_2$CH$_2$— | (phenylaminocarbonyl)amino | ethoxymethyl |
| —CH$_2$CH$_2$CH$_2$CH$_2$— | (phenylaminocarbonothioyl)amino | ethyl |
| —CH$_2$CH$_2$CH$_2$CH$_2$— | (phenylaminocarbonothioyl)amino | propyl |
| —CH$_2$CH$_2$CH$_2$CH$_2$— | (phenylaminocarbonothioyl)amino | butyl |
| —CH$_2$CH$_2$CH$_2$CH$_2$— | (phenylaminocarbonothioyl)amino | 2-methoxyethyl |
| —CH$_2$CH$_2$CH$_2$CH$_2$— | (phenylaminocarbonothioyl)amino | ethoxymethyl |
| —CH$_2$CH$_2$CH$_2$CH$_2$— | {[(3-methoxyphenyl)amino]-carbonyl}amino | ethyl |
| —CH$_2$CH$_2$CH$_2$CH$_2$— | {[(3-methoxyphenyl)amino]-carbonyl}amino | propyl |
| —CH$_2$CH$_2$CH$_2$CH$_2$— | {[(3-methoxyphenyl)amino]-carbonyl}amino | butyl |
| —CH$_2$CH$_2$CH$_2$CH$_2$— | {[(3-methoxyphenyl)amino]-carbonyl}amino | 2-methoxyethyl |
| —CH$_2$CH$_2$CH$_2$CH$_2$— | {[(3-methoxyphenyl)amino]-carbonyl}amino | ethoxymethyl |
| —CH$_2$CH$_2$CH$_2$CH$_2$— | methyl(1-methylpiperdin-4-yl)amino | ethyl |
| —CH$_2$CH$_2$CH$_2$CH$_2$— | methyl(1-methylpiperdin-4-yl)amino | propyl |
| —CH$_2$CH$_2$CH$_2$CH$_2$— | methyl(1-methylpiperdin-4-yl)amino | butyl |
| —CH$_2$CH$_2$CH$_2$CH$_2$— | methyl(1-methylpiperdin-4-yl)amino | 2-methoxyethyl |
| —CH$_2$CH$_2$CH$_2$CH$_2$— | methyl(1-methylpiperdin-4-yl)amino | ethoxymethyl |
| —CH$_2$CH$_2$CH$_2$CH$_2$— | 4-pyrrolidin-1-ylpiperidin-1-yl | ethyl |
| —CH$_2$CH$_2$CH$_2$CH$_2$— | 4-pyrrolidin-1-ylpiperidin-1-yl | propyl |
| —CH$_2$CH$_2$CH$_2$CH$_2$— | 4-pyrrolidin-1-ylpiperidin-1-yl | butyl |

| Z | R$_{3e}$ | R$_2$ |
|---|---|---|
| —CH$_2$CH$_2$CH$_2$CH$_2$— | 4-pyrrolidin-1-ylpiperidin-1-yl | 2-methoxyethyl |
| —CH$_2$CH$_2$CH$_2$CH$_2$— | 4-pyrrolidin-1-ylpiperidin-1-yl | ethoxymethyl |
| —CH$_2$CH$_2$CH$_2$CH$_2$— | 1,4'-bipiperidin-1'-yl | ethyl |
| —CH$_2$CH$_2$CH$_2$CH$_2$— | 1,4'-bipiperidin-1'-yl | propyl |
| —CH$_2$CH$_2$CH$_2$CH$_2$— | 1,4'-bipiperidin-1'-yl | butyl |
| —CH$_2$CH$_2$CH$_2$CH$_2$— | 1,4'-bipiperidin-1'-yl | 2-methoxyethyl |
| —CH$_2$CH$_2$CH$_2$CH$_2$— | 1,4'-bipiperidin-1'-yl | ethoxymethyl |
| —CH$_2$CH$_2$CH$_2$CH$_2$CH$_2$— | (phenylaminocarbonyl)amino | ethyl |
| —CH$_2$CH$_2$CH$_2$CH$_2$CH$_2$— | (phenylaminocarbonyl)amino | propyl |
| —CH$_2$CH$_2$CH$_2$CH$_2$CH$_2$— | (phenylaminocarbonyl)amino | butyl |
| —CH$_2$CH$_2$CH$_2$CH$_2$CH$_2$— | (phenylaminocarbonyl)amino | 2-methoxyethyl |
| —CH$_2$CH$_2$CH$_2$CH$_2$CH$_2$— | (phenylaminocarbonyl)amino | ethoxymethyl |
| —CH$_2$CH$_2$CH$_2$CH$_2$CH$_2$— | (phenylaminocarbonothioyl)amino | ethyl |
| —CH$_2$CH$_2$CH$_2$CH$_2$CH$_2$— | (phenylaminocarbonothioyl)amino | propyl |
| —CH$_2$CH$_2$CH$_2$CH$_2$CH$_2$— | (phenylaminocarbonothioyl)amino | butyl |
| —CH$_2$CH$_2$CH$_2$CH$_2$CH$_2$— | (phenylaminocarbonothioyl)amino | 2-methoxyethyl |
| —CH$_2$CH$_2$CH$_2$CH$_2$CH$_2$— | (phenylaminocarbonothioyl)amino | ethoxymethyl |
| —CH$_2$CH$_2$CH$_2$CH$_2$CH$_2$— | {[(3-methoxyphenyl)amino]-carbonyl}amino | ethyl |
| —CH$_2$CH$_2$CH$_2$CH$_2$CH$_2$— | {[(3-methoxyphenyl)amino]-carbonyl}amino | propyl |
| —CH$_2$CH$_2$CH$_2$CH$_2$CH$_2$— | {[(3-methoxyphenyl)amino]-carbonyl}amino | butyl |
| —CH$_2$CH$_2$CH$_2$CH$_2$CH$_2$— | {[(3-methoxyphenyl)amino]-carbonyl}amino | 2-methoxyethyl |
| —CH$_2$CH$_2$CH$_2$CH$_2$CH$_2$— | {[(3-methoxyphenyl)amino]-carbonyl}amino | ethoxymethyl |
| —CH$_2$CH$_2$CH$_2$CH$_2$CH$_2$— | methyl(1-methylpiperdin-4-yl)amino | ethyl |
| —CH$_2$CH$_2$CH$_2$CH$_2$CH$_2$— | methyl(1-methylpiperdin-4-yl)amino | propyl |
| —CH$_2$CH$_2$CH$_2$CH$_2$CH$_2$— | methyl(1-methylpiperdin-4-yl)amino | butyl |
| —CH$_2$CH$_2$CH$_2$CH$_2$CH$_2$— | methyl(1-methylpiperdin-4-yl)amino | 2-methoxyethyl |
| —CH$_2$CH$_2$CH$_2$CH$_2$CH$_2$— | methyl(1-methylpiperdin-4-yl)amino | ethoxymethyl |
| —CH$_2$CH$_2$CH$_2$CH$_2$CH$_2$— | 4-pyrrolidin-1-ylpiperidin-1-yl | ethyl |
| —CH$_2$CH$_2$CH$_2$CH$_2$CH$_2$— | 4-pyrrolidin-1-ylpiperidin-1-yl | propyl |
| —CH$_2$CH$_2$CH$_2$CH$_2$CH$_2$— | 4-pyrrolidin-1-ylpiperidin-1-yl | butyl |
| —CH$_2$CH$_2$CH$_2$CH$_2$CH$_2$— | 4-pyrrolidin-1-ylpiperidin-1-yl | 2-methoxyethyl |
| —CH$_2$CH$_2$CH$_2$CH$_2$CH$_2$— | 4-pyrrolidin-1-ylpiperidin-1-yl | ethoxymethyl |
| —CH$_2$CH$_2$CH$_2$CH$_2$CH$_2$— | 1,4'-bipiperidin-1'-yl | ethyl |
| —CH$_2$CH$_2$CH$_2$CH$_2$CH$_2$— | 1,4'-bipiperidin-1'-yl | propyl |
| —CH$_2$CH$_2$CH$_2$CH$_2$CH$_2$— | 1,4'-bipiperidin-1'-yl | butyl |
| —CH$_2$CH$_2$CH$_2$CH$_2$CH$_2$— | 1,4'-bipiperidin-1'-yl | 2-methoxyethyl |
| —CH$_2$CH$_2$CH$_2$CH$_2$CH$_2$— | 1,4'-bipiperidin-1'-yl | ethoxymethyl |
| —CH$_2$CH$_2$CH$_2$CH$_2$CH$_2$CH$_2$— | (phenylaminocarbonyl)amino | ethyl |
| —CH$_2$CH$_2$CH$_2$CH$_2$CH$_2$CH$_2$— | (phenylaminocarbonyl)amino | propyl |
| —CH$_2$CH$_2$CH$_2$CH$_2$CH$_2$CH$_2$— | (phenylaminocarbonyl)amino | butyl |
| —CH$_2$CH$_2$CH$_2$CH$_2$CH$_2$CH$_2$— | (phenylaminocarbonyl)amino | 2-methoxyethyl |
| —CH$_2$CH$_2$CH$_2$CH$_2$CH$_2$CH$_2$— | (phenylaminocarbonyl)amino | ethoxymethyl |
| —CH$_2$CH$_2$CH$_2$CH$_2$CH$_2$CH$_2$— | (phenylaminocarbonothioyl)amino | ethyl |
| —CH$_2$CH$_2$CH$_2$CH$_2$CH$_2$CH$_2$— | (phenylaminocarbonothioyl)amino | propyl |
| —CH$_2$CH$_2$CH$_2$CH$_2$CH$_2$CH$_2$— | (phenylaminocarbonothioyl)amino | butyl |
| —CH$_2$CH$_2$CH$_2$CH$_2$CH$_2$CH$_2$— | (phenylaminocarbonothioyl)amino | 2-methoxyethyl |
| —CH$_2$CH$_2$CH$_2$CH$_2$CH$_2$CH$_2$— | (phenylaminocarbonothioyl)amino | ethoxymethyl |
| —CH$_2$CH$_2$CH$_2$CH$_2$CH$_2$CH$_2$— | {[(3-methoxyphenyl)amino]-carbonyl}amino | ethyl |
| —CH$_2$CH$_2$CH$_2$CH$_2$CH$_2$CH$_2$— | {[(3-methoxyphenyl)amino]-carbonyl}amino | propyl |
| —CH$_2$CH$_2$CH$_2$CH$_2$CH$_2$CH$_2$— | {[(3-methoxyphenyl)amino]-carbonyl}amino | butyl |
| —CH$_2$CH$_2$CH$_2$CH$_2$CH$_2$CH$_2$— | {[(3-methoxyphenyl)amino]-carbonyl}amino | 2-methoxyethyl |
| —CH$_2$CH$_2$CH$_2$CH$_2$CH$_2$CH$_2$— | {[(3-methoxyphenyl)amino]-carbonyl}amino | ethoxymethyl |
| —CH$_2$CH$_2$CH$_2$CH$_2$CH$_2$CH$_2$— | methyl(1-methylpiperdin-4-yl)amino | ethyl |
| —CH$_2$CH$_2$CH$_2$CH$_2$CH$_2$CH$_2$— | methyl(1-methylpiperdin-4-yl)amino | propyl |
| —CH$_2$CH$_2$CH$_2$CH$_2$CH$_2$CH$_2$— | methyl(1-methylpiperdin-4-yl)amino | butyl |
| —CH$_2$CH$_2$CH$_2$CH$_2$CH$_2$CH$_2$— | methyl(1-methylpiperdin-4-yl)amino | 2-methoxyethyl |
| —CH$_2$CH$_2$CH$_2$CH$_2$CH$_2$CH$_2$— | methyl(1-methylpiperdin-4-yl)amino | ethoxymethyl |

-continued

| Z | R$_{3e}$ | R$_2$ |
|---|---|---|
| —CH$_2$CH$_2$CH$_2$CH$_2$CH$_2$CH$_2$— | 4-pyrrolidin-1-ylpiperidin-1-yl | ethyl |
| —CH$_2$CH$_2$CH$_2$CH$_2$CH$_2$CH$_2$— | 4-pyrrolidin-1-ylpiperidin-1-yl | propyl |
| —CH$_2$CH$_2$CH$_2$CH$_2$CH$_2$CH$_2$— | 4-pyrrolidin-1-ylpiperidin-1-yl | butyl |
| —CH$_2$CH$_2$CH$_2$CH$_2$CH$_2$CH$_2$— | 4-pyrrolidin-1-ylpiperidin-1-yl | 2-methoxyethyl |
| —CH$_2$CH$_2$CH$_2$CH$_2$CH$_2$CH$_2$— | 4-pyrrolidin-1-ylpiperidin-1-yl | ethoxymethyl |
| —CH$_2$CH$_2$CH$_2$CH$_2$CH$_2$CH$_2$— | 1,4'-bipiperidin-1'-yl | ethyl |
| —CH$_2$CH$_2$CH$_2$CH$_2$CH$_2$CH$_2$— | 1,4'-bipiperidin-1'-yl | propyl |
| —CH$_2$CH$_2$CH$_2$CH$_2$CH$_2$CH$_2$— | 1,4'-bipiperidin-1'-yl | butyl |
| —CH$_2$CH$_2$CH$_2$CH$_2$CH$_2$CH$_2$— | 1,4'-bipiperidin-1'-yl | 2-methoxyethyl |
| —CH$_2$CH$_2$CH$_2$CH$_2$CH$_2$CH$_2$— | 1,4'-bipiperidin-1'-yl | ethoxymethyl |
| —CH$_2$CH$_2$OCH$_2$CH$_2$— | (phenylaminocarbonyl)amino | ethyl |
| —CH$_2$CH$_2$OCH$_2$CH$_2$— | (phenylaminocarbonyl)amino | propyl |
| —CH$_2$CH$_2$OCH$_2$CH$_2$— | (phenylaminocarbonyl)amino | butyl |
| —CH$_2$CH$_2$OCH$_2$CH$_2$— | (phenylaminocarbonyl)amino | 2-methoxyethyl |
| —CH$_2$CH$_2$OCH$_2$CH$_2$— | (phenylaminocarbonyl)amino | ethoxymethyl |
| —CH$_2$CH$_2$OCH$_2$CH$_2$— | (phenylaminocarbonothioyl)amino | ethyl |
| —CH$_2$CH$_2$OCH$_2$CH$_2$— | (phenylaminocarbonothioyl)amino | propyl |
| —CH$_2$CH$_2$OCH$_2$CH$_2$— | (phenylaminocarbonothioyl)amino | butyl |
| —CH$_2$CH$_2$OCH$_2$CH$_2$— | (phenylaminocarbonothioyl)amino | 2-methoxyethyl |
| —CH$_2$CH$_2$OCH$_2$CH$_2$— | (phenylaminocarbonothioyl)amino | ethoxymethyl |
| —CH$_2$CH$_2$OCH$_2$CH$_2$— | {[(3-methoxyphenyl)amino]-carbonyl}amino | ethyl |
| —CH$_2$CH$_2$OCH$_2$CH$_2$— | {[(3-methoxyphenyl)amino]-carbonyl}amino | propyl |
| —CH$_2$CH$_2$OCH$_2$CH$_2$— | {[(3-methoxyphenyl)amino]-carbonyl}amino | butyl |
| —CH$_2$CH$_2$OCH$_2$CH$_2$— | {[(3-methoxyphenyl)amino]-carbonyl}amino | 2-methoxyethyl |
| —CH$_2$CH$_2$OCH$_2$CH$_2$— | {[(3-methoxyphenyl)amino]-carbonyl}amino | ethoxymethyl |
| —CH$_2$CH$_2$OCH$_2$CH$_2$— | methyl(1-methylpiperdin-4-yl)amino | ethyl |
| —CH$_2$CH$_2$OCH$_2$CH$_2$— | methyl(1-methylpiperdin-4-yl)amino | propyl |
| —CH$_2$CH$_2$OCH$_2$CH$_2$— | methyl(1-methylpiperdin-4-yl)amino | butyl |
| —CH$_2$CH$_2$OCH$_2$CH$_2$— | methyl(1-methylpiperdin-4-yl)amino | 2-methoxyethyl |
| —CH$_2$CH$_2$OCH$_2$CH$_2$— | methyl(1-methylpiperdin-4-yl)amino | ethoxymethyl |
| —CH$_2$CH$_2$OCH$_2$CH$_2$— | 4-pyrrolidin-1-ylpiperidin-1-yl | ethyl |
| —CH$_2$CH$_2$OCH$_2$CH$_2$— | 4-pyrrolidin-1-ylpiperidin-1-yl | propyl |
| —CH$_2$CH$_2$OCH$_2$CH$_2$— | 4-pyrrolidin-1-ylpiperidin-1-yl | butyl |
| —CH$_2$CH$_2$OCH$_2$CH$_2$— | 4-pyrrolidin-1-ylpiperidin-1-yl | 2-methoxyethyl |
| —CH$_2$CH$_2$OCH$_2$CH$_2$— | 4-pyrrolidin-1-ylpiperidin-1-yl | ethoxymethyl |
| —CH$_2$CH$_2$OCH$_2$CH$_2$— | 1,4'-bipiperidin-1'-yl | ethyl |
| —CH$_2$CH$_2$OCH$_2$CH$_2$— | 1,4'-bipiperidin-1'-yl | propyl |
| —CH$_2$CH$_2$OCH$_2$CH$_2$— | 1,4'-bipiperidin-1'-yl | butyl |
| —CH$_2$CH$_2$OCH$_2$CH$_2$— | 1,4'-bipiperidin-1'-yl | 2-methoxyethyl |
| —CH$_2$CH$_2$OCH$_2$CH$_2$— | 1,4'-bipiperidin-1'-yl | ethoxymethyl |

Compounds of the invention have been found to modulate cytokine biosynthesis by inducing the production of interferon α and/or tumor necrosis factor α in human cells when tested using one of the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testermang et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at 4×10$^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is 2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8, 9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at 4×10$^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is 2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A compound of Formula II:

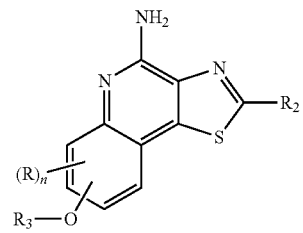

wherein:
$R_3$ is selected from the group consisting of:
—Z—O—$R_4$,
—Z—[N($R_8$)-Q]-X—O—$R_4$,
—Z—[N($R_8$)-Q]-X—[V—N($R_8$)]—X—O—$R_4$;
R is selected from the group consisting of alkyl, alkoxy, hydroxy, halogen, and trifluoromethyl;
n is 0 or 1;
$R_2$ is selected from the group consisting of hydrogen, alkyl, alkoxyalkylenyl, and hydroxyalkylenyl;
Z is selected from the group consisting of alkylene, alkenylene, and alkynylene, wherein alkylene, alkenylene, and alkynylene can be optionally interrupted with one or more —O— groups;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
$R_4$ is a [1,3]thiazolo[4,5-c]quinoline optionally substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;
$R_6$ is selected from the group consisting of =O and =S;
$R_8$ is selected from the group consisting of hydrogen, alkyl, hydroxyalkylenyl, alkoxyalkylenyl, arylalkylenyl, and heteroarylalkylenyl;

$R_9$ is selected from the group consisting of hydrogen and alkyl;

V is selected from the group consisting of —C($R_6$)—, —N($R_8$)—C($R_6$)—, and —S(O)$_2$—;

W is selected from the group consisting of a bond, —C(O)—, and —S(O)$_2$—; or a pharmaceutically acceptable salt thereof.

2. The compound or salt of claim 1 wherein $R_4$ is a [1,3]thiazolo[4,5-c]quinolone substituted by an amino group.

3. The compound or salt of claim 1 wherein n is 0.

4. The compound or salt of claim 1 wherein $R_2$ is selected from the group consisting of methyl, ethyl, n-propyl, n-butyl, ethoxymethyl, methoxymethyl, 2-methoxyethyl, hydroxymethyl, and 2-hydroxyethyl.

5. The compound or salt of any of claim 1 wherein W is a bond.

6. The compound or salt of claim 1 wherein Q is selected from the group consisting of —C($R_6$)—, —S(O)$_2$—, —C($R_6$)—N($R_8$)—W— and W is a bond.

7. The compound or salt of claim 1 wherein Q is —C($R_6$)—N($R_8$)—W— and W is a bond.

8. The compound or salt of claim 1 wherein X is alkylene optionally interrupted by one or more —O— groups.

9. The compound or salt of claim 1 wherein $R_8$ is hydrogen.

10. The compound or salt of claim 1 wherein Z is alkylene optionally interrupted with one or more —O— groups.

11. The compound or salt of claim 1 wherein Z is selected from the group consisting of $C_{1-6}$ alkylene and —CH$_2$CH$_2$—O—CH$_2$CH$_2$—.

12. The compound or salt of claim 1 wherein —O—$R_3$ is at the 7-position or at the 8-position.

13. The compound or salt of claim 1 wherein $R_3$ is —Z—[N($R_8$)-Q]-X—O—$R_4$; Z is alkylene optionally interrupted with one or more —O— groups; X is alkylene optionally interrupted by one or more —O— groups; Q is —C($R_6$)—N($R_8$)—W—; W is a bond; $R_6$ is =O; and $R_8$ is hydrogen.

14. The compound or salt of claim 2 wherein n is 0; $R_2$ is selected from the group consisting of methyl, ethyl, n-propyl, n-butyl, ethoxymethyl, methoxymethyl, and 2-methoxyethyl; Z is alkylene optionally interrupted with one or more —O— groups; X is alkylene optionally interrupted by one or more —O— groups; Q is —C($R_6$)—N($R_8$)—W— and W is a bond.

15. A pharmaceutical composition comprising a therapeutically effective amount of a compound or salt of claim 1 and a pharmaceutically acceptable carrier.

16. A method of inducing cytokine biosynthesis in an animal comprising administering an effective amount of a compound or salt of claim 1 to the animal, wherein the cytokine is selected from interferon alpha and tumor necrosis factor alpha.

17. A method of treating a viral disease in an animal in need thereof comprising administering a therapeutically effective amount of a compound or salt of claim 1, wherein the viral disease is selected from herpesvirus and papovavirus.

18. A method of treating a neoplastic disease in an animal in need thereof comprising administering a therapeutically effective amount of a compound or salt of claim 1, wherein the neoplastic disease is selected from basal cell carcinoma and actinic keratosis.

19. A compound of the formula:

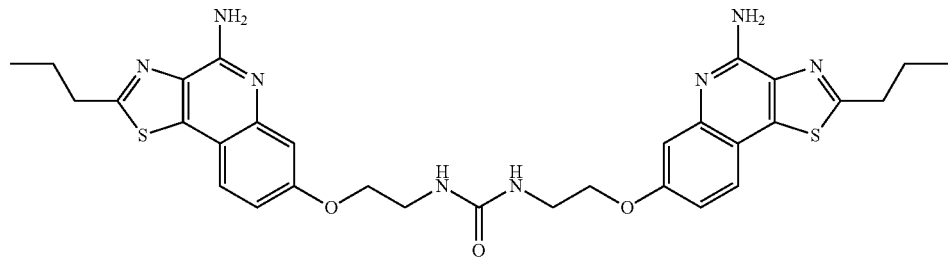 [SMILES: CCCc1nc2c(N)nc3cc(OCCNC(=O)NCCOc4ccc5c(c4)nc(N)c4nc(CCC)sc45)ccc3c2s1]

or a pharmaceutically acceptable salt thereof.

20. A compound of the formula:

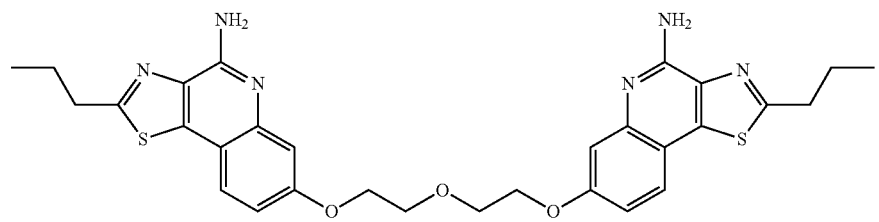 [SMILES: CCCc1nc2c(N)nc3cc(OCCOCCOc4ccc5c(c4)nc(N)c4nc(CCC)sc45)ccc3c2s1]

or a pharmaceutically acceptable salt thereof.

21. A compound of the formula:
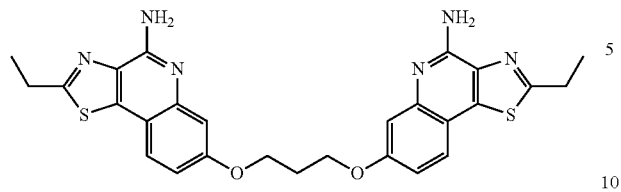
or a pharmaceutically acceptable salt thereof.
* * * * *

UNITED STATES PATENT AND TRADEMARK OFFICE
CERTIFICATE OF CORRECTION

PATENT NO. : 9,546,184 B2
APPLICATION NO. : 14/732815
DATED : January 17, 2017
INVENTOR(S) : Ryan B. Prince et al.

Page 1 of 3

It is certified that error appears in the above-identified patent and that said Letters Patent is hereby corrected as shown below:

On the Title Page

Item (63) "Continuation of application No. 11/884,052, filed on Aug. 13, 2008, now abandoned." should read -- Continuation of application No. 11/884,052, filed Aug. 13, 2008, now abandoned, which is a national stage filing under 35 USC 371 of PCT/US2006/004391, filed Feb. 8, 2006, which claims priority to US Provisional Application No. 60/651,585, filed Feb. 9, 2005 and US Provisional Application No. 60/733,036, filed Nov. 3, 2005. --.

In the Specification

Column 1
Line 11, delete "Aug. 9, 2007," and insert -- Feb. 8, 2006, --, therefor.

Column 4
Line 40, below "-C($R_6$)-O-," insert -- -O-C($R_6$)-, --.
Line 46, below "-O-N($R_8$)-Q-," insert -- -O-N=C($R_4$)-, --.
Line 47, above "-CH(-N(-O-$R_8$)-Q-$R_4$)-," insert -- -C(=N-O-$R_8$)-, --.

Column 6
Line 62, below "-Z-Y-$R_4$," insert -- -Z-Y-X-Y-$R_4$, --.

Column 7
Line 6, above "-X-Y'-$R_4$, and" insert -- -X-$R_4$, --.

Column 11
Line 12, above "-O-N=C($R_4$)-," insert -- -O-N($R_8$)-Q-, --.

Column 22
Line 46, delete "hydroxyallcyl," and insert -- hydroxyalkyl, --, therefor.

Signed and Sealed this
Twenty-second Day of May, 2018

Andrei Iancu
*Director of the United States Patent and Trademark Office*

Column 24
Line 45 (approx.), below "-R$_4$," insert -- -X-R$_4$, --.

Column 28
Line 44, delete "bicylic" and insert -- bicyclic --, therefor.

Column 40
Line 67, delete "potertial" and insert -- potential --, therefor.

Column 43
Line 29 (approx.), delete "IIalide-R$_3$." and insert -- Halide-R$_3$. --, therefor.

Column 44
Line 25 (approx.), delete "IIalide-Z" and insert -- Halide-Z --, therefor.

Column 48
Line 60 (approx.), delete "Biorg." and insert -- Bioorg. --, therefor.

Column 55
Line 4 (approx.), delete "dicylcohexylmethane" and insert -- dicyclohexylmethane --, therefor.
Line 6-7, delete "pyrdinedicarbonyl" and insert -- pyridinedicarbonyl --, therefor.

Column 57
Line 66, delete "piperdinecarboxylate" and insert -- piperidinecarboxylate --, therefor.

Column 61
Line 48, delete "dervied" and insert -- derived --, therefor.

Column 64
Line 23-24, delete "hemophilus" and insert -- haemophilus --, therefor.

Columns 103-104
Under Example 99, delete "1-(2-Pyrimdyl)" and insert -- 1-(2-Pyridyl) --, therefor.

Column 118
Line 56, delete "Dimethylearbamoyl" and insert -- Dimethylcarbamoyl --, therefor.

Column 128
Line 39 (approx.), delete "2," and insert -- Z, --, therefor.

Column 147
Line 6-7 (approx.), delete "electrochemoluminescent" and insert -- electrochemiluminescent --, therefor.

In the Claims

Column 149
Line 17, Claim 5, delete "of any of" and insert -- of --, therefor.